(12) United States Patent
Lewis

(10) Patent No.: US 7,723,109 B2
(45) Date of Patent: *May 25, 2010

(54) EXPRESSION OF SPIDER SILK PROTEINS

(75) Inventor: Randolph V. Lewis, Laramie, WY (US)

(73) Assignee: University of Wyoming, Laramie, WY (US)

( * ) Notice: Subject to any disclaimer, the term of this patent is extended or adjusted under 35 U.S.C. 154(b) by 89 days.

This patent is subject to a terminal disclaimer.

(21) Appl. No.: 11/926,871

(22) Filed: Oct. 29, 2007

(65) Prior Publication Data

US 2008/0109923 A1 May 8, 2008

Related U.S. Application Data

(63) Continuation of application No. 10/479,638, filed as application No. PCT/US02/18256 on Jun. 6, 2002, now Pat. No. 7,288,391.

(60) Provisional application No. 60/296,184, filed on Jun. 6, 2001.

(51) Int. Cl.
| | |
|---|---|
| C12N 5/00 | (2006.01) |
| C12P 21/06 | (2006.01) |
| C07H 17/00 | (2006.01) |
| C07K 14/00 | (2006.01) |

(52) U.S. Cl. .................. 435/410; 435/325; 435/243; 435/320.1; 530/300; 530/350; 536/23.1

(58) Field of Classification Search .................. None
See application file for complete search history.

(56) References Cited

U.S. PATENT DOCUMENTS

| | | | |
|---|---|---|---|
| 5,245,012 A | 9/1993 | Lombari et al. | |
| 6,608,242 B1 | 8/2003 | Yang | |
| 7,288,391 B2 * | 10/2007 | Roth et al. | .............. 435/69.1 |

OTHER PUBLICATIONS

Gatesy et al. 2001; Extreme diversity, conservation, and convergence of spider silk fibroin sequences. Science 291:2603-2605.*
Guerette et al. 1996; Silk properties determined by gland-specific expression of a spider fibroin gene family. Science 272:112-115.
Scheller, J. et al. "Production of spider silk proteins in tobacco and potato"; Nature Biotechnology, 19: 573-577 (2001).
Austin, S., et al., "Production and field performance of trasngenic alfalfa (*Medicago sativa* L.) expressing alpha-amylase and manganese-dependent lignin peroxidase", Euphytica, 85:381-393 (1995).
Bell, A.L., et al., "Changes in Fine Structure During Silk Protein Production in the Ampullate Gland of the Spider *Araneus sericatus*", J. of Cell Biol, 42:284-295, (1969).
Brown, D.C.W., et al., "Role of genetic background in somatic embryogenesis in Medicago", Plant Cell Tissue Organ Culture 4: 111-122 (1985).
Gil, J., et al., "In Vivo Regulation of Protein Synthesis by Phosphorylation of the .alpha. Subunit of Wheat Eukaryotic Initiation Factor 2", Biochemistry 39: 7521-7530, (2000).

Chang, L-Y, et al., "Specific in vitro phosphorylation of plant eIF2.alpha. by eukaryotic eIF2.alpha. kinases", Plant Molecular Biology, vol. 41: 363-370, (1999).
Gil, J., et al., "In Vivo Regulation of the dsRNA-Dependent Protein Kinase PKR by the Cellular Glycoprotein P67", Biochemistry, 39: 16016-16025, (2000).
Hinman, M.B., et al., "Isolation of a Clone Encoding a Second Dragline Silk Fibroin *Nephila clavipes* Dragline Silk is a Two-Protein Fiber", J. of Biol. Chem., vol. 267:19320-19324 (1992).
Huang, S., et al., "Overexpression of 20-Oxidase Confers a Gibberellin—Overproduction Phenotype in Arabidopsis", Plant Physiol. 118: 773-781, (1998).
Iizuka, E., "The physico-chemical properties of silk fibers and the fiber spinning process", Experientia, 39: 449-454, (1983).
Lucas, F., "Spiders and their silks", Discovery 25:20-26 (1964).
Stauffer, S.L., et al., "Comparison of Physical Properties of Three Silks From *Nephila clavipes* and *Araneus gemmoides*", J. of Arachnology, 22:5-11 (1994).
Thiel, B.R., et al., "Physical and Chemical Microstructure of Spider Dragline: A Study by Analytical Transmission Electron Microscopy", Biopolymers, vol. 34:1089-1097 (1994).
Vollrath, F., "Spider Webs and Silks", Scientific American Mar. 1992 70-76.
Willcox, P.J., et al., "Evidence of a Cholesteric Liquid Crystalline Phase in Natural Silk Spinning Processes", Macromolecules, 29: 5106-5110 (1996).
Work, R.W., "Dimensions, Birefringences, and Force-Elongation Behavior of Major and Minor Ampullate Silk Fibers from Orb-Web-Spinning Spiders—The Effects of Wetting on These Properties", Textile Research Journal, Oct. 1977 p. 650-662.
Xu, M., et al., "Structure of a protein superfiber: Spider dragline silk", Proc. Natl. Acad. Sci. U.S.A., 87: 7120-7124, (1990).
Scheller, J., et al., "Purification of spider silk-elastin from transgenic plants and application for human chondrocyte proliferation", Transgenic Research, 13: 51-57 (2004).
Menassa, R., et al., "Spider dragline silk proteins in transgenic tobacco leaves: accumulation and field production", Plant Biotechnology Journal 2: 431-438 (2004).
Parkhe, A.D., et al., "Structural Studies of Spider Silk Proteins in the Fiber", Journal of Molecular Recognition, 10: 1-6 (1997).
Horsch, R.B., et al., "A Simple and General Method for Transferring Genes into Plants", Science, 227: 1229-1231 (1985).
Gosline, J.M., et al., "Spider silk as rubber", Nature, 309:551-551 (1984).
Abstract, "Plants made to silk", Trends in Genetics 17:442-443, News and Comments, Aug. 2001.
Fischer, E., "About Spider Silk", Hoppe-Seyler's Zeitschrift fur physiologische Chemie, 53:126-139 (1907).
Kovoor,P.J., "Etude Histochimique et Cytologique des Glands Sericigenes de Quelques Argiopidae", Annales des Sciences Naturelles, 12:1-40 (1972).
Priuzian, E.S., et al., "Construction of Synthetic Genes for Analogs of Spider Silk Spidroin 1 and Their Expression in Tobacco Plants", Mol. Biol. (Mosk) 37(4):654-662 (2003).

(Continued)

*Primary Examiner*—Karen Cochrane Carlson
(74) *Attorney, Agent, or Firm*—Dann, Dorfman, Herrell & Skillman; Kathleen D. Rigaut

(57) ABSTRACT

The present invention relates to the fields of molecular biology and plant biology. Specifically, the invention is directed to the methods for expressing spider silk proteins in plants and the synthesis and purification of spider silk proteins therefrom.

17 Claims, 28 Drawing Sheets

OTHER PUBLICATIONS

Micallef, M.C., et al., "Improvement of Transgenic Alfalfa by Backcrossing", In Vitro Cell Dev. Biol.—Plant 31:187-192, (Oct. 1995).

Gosline, J.M., et al., "The structure and properties of spider silk", Evdeavour, 10(1):37-43 (1986).

* cited by examiner

Fig. 3A

Nephila clavipes dragline silk fibroin (spidroin 2) mRNA,
3' end (1981 bp). GenBank Accession Number M92913.
(SEQ ID NO: 1)

```
   1 cctggaggat atggaccagg acaacaaggc ccaggaggat atggccctgg acaacaagga
  61 ccatctggac ctggcagtgc cgctgcagca gcagcagccg ccgcagcagg acctggagga
 121 tatggccctg acaacaagg acccggagga tatggaccag gacaacaagg acccggaaga
 181 tatggaccag gacaacaagg accatctgga cctggcagtg ccgctgcagc cgcagcagga
 241 tctggacaac aaggcccagg aggatatgga ccacgtcaac aaggtccagg aggttatgga
 301 caaggacaac aaggaccatc tggaccaggc agtgcagccg cagcctcagc cgcagcctca
 361 gcagaatctg gacaacaagg cccaggaggt tatggaccag gtcaacaagg cccaggaggt
 421 tatggaccag gtcaacaagg tcctggagga tatggaccag gacaacaagg accatctgga
 481 ccaggtagtg ccgctgcagc agccgccgcc gcatcaggac ctggacaaca aggaccagga
 541 ggatatggac caggtcaaca aggtcctgga ggatatggac caggacaaca aggaccatct
 601 ggaccaggta gtgccgctgc agccgccgcc gccgcatcag gacctggaca acaaggacca
 661 ggaggatatg gaccaggtca acaaggtcca ggaggttatg gaccaggaca acaaggacta
 721 tctggaccag gcagtgcagc tgcagcagcc gcagcaggac tggacaaca aggacccgga
 781 ggatatggac caggacaaca aggaccatct ggacccggta gtgccgctgc agcagcagcc
 841 gccgcagcag gacctggagg atatggccct ggacaacaag acccggagg atatggacca
 901 ggacaacaag gaccatctgg agcaggcagt gcagcagcag cagccgcagc aggacctgga
 961 caacaaggat taggaggtta tggaccagga caacaaggtc aggaggata tggaccagga
1021 caacaaggtc aggaggata tggaccaggt agtgcatctg cagcagcagc cgcagcagga
1081 cctggacaac aaggaccagg aggatatgga cctggacaac aaggaccatc tggaccaggc
1141 agtgcatctg cagcagcagc cgcagccgca gcaggaccag gaggatatgg accaggacaa
1201 caaggtccag gaggatatgc accaggacaa caaggaccat ctggaccagg cagtgcatct
1261 gcagcagcag ccgcagccgc agcaggacca ggaggatatg gaccaggaca acaaggtcca
1321 ggaggatatg caccaggaca acaaggacca tctggaccag gcagtgcagc agcagcagca
1381 gctgctgcag caggacctgg tggatatgga ccagcgcaac agggaccatc tggtcctgga
1441 atcgcagctt cagctgcttc agcaggacct ggaggttatg accagcaca acaaggacca
1501 gctggatatg ggcctggaag cgcagtagca gcctctgccg gtgcaggatc tgcaggttat
1561 gggccaggtt ctcaagcttc cgctgcagct ctcgtctgg cttctccaga ttcaggcgct
1621 agagttgcat cagctgtttc taacttggta ccagtggcc caactagctc tgctgcctta
1681 tcaagtgtta tcagtaacgc tgtgtctcaa attggcgcaa gtaatcctgg tctctctggt
1741 tgcgatgtcc tcattcaagc tctcttggaa atcgtttctg cttgtgtaac catcctttct
1801 tcatccagca ttggtcaagt taattatgga gcggcttctc agttcgccca agttgtcggc
1861 caatctgttt tgagtgcatt ttaattgaaa aatttattaa aatatgcatg gattttctag
1921 cctgggcaac taattgctcg tactatgtaa ttttttttta aataaattct ttgcaacttc
1981 t
```

Fig. 3B

Amino acid sequence of Nephila clavipes dragline silk fibroin (SEQ ID NO: 12).

PGGYGPGQQGPGGYGPGQQGPSGPGSAAAAAAAAAAGPGGYGPG

QQGPGGYGPGQQGPGRYGPGQQGPSGPGSAAAAAAGSGQQGPGGYGPRQQGPGGYGQG

QQGPSGPGSAAAASAAASAESGQQGPGGYGPGQQGPGGYGPGQQGPGGYGPGQQGPSG

PGSAAAAAAAASGPGQQGPGGYGPGQQGPGGYGPGQQGPSGPGSAAAAAAAASGPGQQ

GPGGYGPGQQGPGGYGPGQQGLSGPGSAAAAAAAGPGQQGPGGYGPGQQGPSGPGSAA

AAAAAAAGPGGYGPGQQGPGGYGPGQQGPSGAGSAAAAAAAGPGQQGLGGYGPGQQGP

GGYGPGQQGPGGYGPGSASAAAAAAGPGQQGPGGYGPGQQGPSGPGSASAAAAAAAG

PGGYGPGQQGPGGYAPGQQGPSGPGSASAAAAAAAGPGGYGPGQQGPGGYAPGQQGP

SGPGSAAAAAAAAGPGGYGPAQQGPSGPGIAASAASAGPGGYGPAQQGPAGYGPGSA

VAASAGAGSAGYGPGSQASAAASRLASPDSGARVASAVSNLVSSGPTSSAALSSVISN

AVSQIGASNPGLSGCDVLIQALLEIVSACVTILSSSSIGQVNYGAASQFAQVVGQSVL

Figure 4

SEQ ID NO: 2 cccgggtggctatggtcctggacagcaaggtcctggcggttacggtcctggccaacagggtccctctgg
tccaggcagtgcagctgccgcagccgccgcagcgggtccgga Amino acid sequence (SEQ ID NO: 13) encoded by SEQ ID NO: 2

PGGYGPGQQGPGGYGPGQQGPSGPGSAAAAAAAAG

Figure 5

SEQ ID NO: 3

```
gatcccccgggtggctatggtcctggacagcaaggtcctggcggttacggtcctggccaacagggtccc
tctggtccaggcagtgcagctgccgcagccgccgcagcgggtccgggtggctatggtcctggacagcaa
ggtcctggcggttacggtcctggccaacagggtccctctggtccaggcagtgcagctgccgcagccgcc
gcagcgggtccgggtggctatggtcctggacagcaaggtcctggcggttacggtcctggccaacagggt
ccctctggtccaggcagtgcagctgccgcagccgccgcagcgggtccgggtggctatggtcctggaca
gcaaggtcctggcggttacggtcctggccaacagggtccctctggtccaggcagtgcagctgccgcagc
cgccgcagcgggtccggacccgggtggctatggtcctggacagcaaggtcctggcggttacggtcctgg
ccaacagggtccctctggtccaggcagtgcagctgccgcagccgccgcagcgggtccggacccgggtgg
ctatggtcctggacagcaaggtcctggcggttacggtcctggccaacagggtccctctggtccaggcag
tgcagctgccgcagccgccgcagcgggtccggacccgggtggctatggtcctggacagcaaggtcctgg
cggttacggtcctggccaacagggtccctctggtccaggcagtgcagctgccgcagccgccgcagcggg
tccggacccgggtggctatggtcctggacagcaaggtcctggcggttacggtcctggccaacagggtcc
ctctggtccaggcagtgcagctgccgcagccgccgcagcgggtccggacccgggtggctatggtcctgg
acagcaaggtcctggcggttacggtcctggccaacagggtccctctggtccaggcagtgcagctgccgc
agccgccgcagcgggtccggacccgggtggctatggtcctggacagcaaggtcctggcggttacggtcc
tggccaacagggtccctctggtccaggcagtgcagctgccgcagccgccgcagcgggtccggacccggg
tggctatggtcctggacagcaaggtcctggcggttacggtcctggccaacagggtccctctggtccagg
cagtgcagctgccgcagccgccgcagcgggtccggacccgggtggctatggtcctggacagcaaggtcc
tggcggttacggtcctggccaacagggtccctctggtccaggcagtgcagctgccgcagccgccgcagc
gggtccggacccgggtggctatggtcctggacagcaaggtcctggcggttacggtcctggccaacaggg
tccctctggtccaggcagtgcagctgccgcagccgccgcagcgggtccggacccgggtggctatggtcc
tggacagcaaggtcctggcggttacggtcctggccaacagggtccctctggtccaggcagtgcagctgc
cgcagccgccgcagcgggtccggacccgggtggctatggtcctggacagcaaggtcctggcggttacgg
tcctggccaacagggtccctctggtccaggcagtgcagctgccgcagccgccgcagcgggtccggaccg
ggtggctatggtcctggacagcaaggtcctggcggttacggtcctggccaacagggtccctctggtcca
ggcagtgcagctgccgcagccgccgcagcgggtccggatcaagcttatcgataccgtcgggatc
```

Amino acid sequence (SEQ ID NO: 14) encoded by SEQ ID NO: 3.

```
DPPGGYGPGQQGPGGYGPGQQGPSGPGSAAAAAAAAGPGGYGPGQQGPGGYGPGQQGPSGPGSAAAAAA
AAGPGGYGPGQQGPGGYGPGQQGPSGPGSAAAAAAAAGPGWLWSWTARSWRLRSWPTGSLWSRQCSCRS
RRSGSGPGWLWSWTARSWRLRSWPTGSLWSRQCSCRSRRSGSGPGWLWSWTARSWRLRSWPTGSLWSRQ
CSCRSRRSGSGPGWLWSWTARSWRLRSWPTGSLWSRQCSCRSRRSGSGPGWLWSWTARSWRLRSWPTGS
LWSRQCSCRSRRSGSGPGWLWSWTARSWRLRSWPTGSLWSRQCSCRSRRSGSGPGWLWSWTARSWRLRS
WPTGSLWSRQCSCRSRRSGSGPGWLWSWTARSWRLRSWPTGSLWSRQCSCRSRRSGSGPGWLWSWTARS
WRLRSWPTGSLWSRQCSCRSRRSGSGPGWLWSWTARSWRLRSWPTGSLWSRQCSCRSRRSGSGPGWLWS
WTARSWRLRSWPTGSLWSRQCSCRSRRSGSGPGWLWSWTARSWRLRSWPTGSLWSRQCSCRSRRSGSGP
GGYGPGQQGPGGYGPGQQGPSGPGSAAAAAAAAGPDQAYRYRRD
```

Figure 9

Argiope trifasciata aciniform fibroin 1 mRNA, partial cds.
DNA sequence of 3' region (709 bp; SEQ ID NO: 4)

ggcatcaatgtagatagcggcagtgtacaaagtgacattagttccagtagcagcttcctctc
aacaagctcgtcttcggccagttactctcaggcatcagcttcttcgagcagcggtgccggat
acacaggaccttctggaccttccactggaccgtctggctaccctgggcctttgagtggcgga
gcgtcgttcggctctggccaatcttctttcggtcaaacttcagccttttccgcatctggtgc
tggacaatcggctggagtatctgttatatcttctcttaattcacccgttggattgaggtctc
cttctgctgcttctagacttagtcaattaacatcatccataacgaatgcagttggtgccaat
ggtgttgatgctaattctcttgcccgtagtcttcaatctagtttctcggcactcagaagctc
cggcatgtcttcaagcgatgctaaaattgaagtattgttggaaaccattgttggtctgcttc
agcttttgagcaacactcaagtccgaggagtaaacccggcaacggcttcttcagtagcaaat
tctgctgcgagatcttttgaattagttttggcttaagagatattgattgttagacctggaga
taaatgtaacttttctgatatgcaatttgcatacgaaatttcttattaaataaaagcatttt
gaaacattaaaaaaaaaaaaaaaaaa Amino acid sequence of Argiope trifasciata aciniform fibroin 1
(SEQ ID NO: 15)

GINVDSGSVQSDISSSSSFLSTSSSSASYSQASASSSSGAGYTGPSGPSTGPSGYPGPLSGG
ASFGSGQSSFGQTSAFSASGAGQSAGVSVISSLNSPVGLRSPSAASRLSQLTSSITNAVGAN
GVDANSLARSLQSSFSALRSSGMSSSDAKIEVLLETIVGLLQLLSNTQVRGVNPATASSVAN
SAARSFELVLA*

Figure 10

Phidippus audax fibroin 1 mRNA, partial cds.
DNA sequence (1711 bp; SE Q ID NO: 5)

```
ggagctggagctggcgctggctatggtgcaggtgctggttcaggagctggtgcaggctctgg
tgcaggagctggagcaggagctggagcaggagctggagcaggctatggagcaggagcaggtt
caggagctggtgctggcgcaggttacggacgaggtgcaggagcaggagcgggagctggagca
ggttacggccaaggtgctggagcgggagctggtgccggcgcaggctatggcgctggagctgg
atctggagctggagccggctatggtacaggtgctggttcaggagctggttcaggagctggtt
caggagctggatcaggagctggagcaggagctggagcaggtgcaggttatggagcaggagca
ggttcaggagctggtgctggcgcaggctacggacgaggtgcaggagcaggagcgggagctgg
agcaggttacggccaaggtgctggagcaggagctggtgccggtgcaggtgctggttcaggag
ctggtgcaggttctggtgcaggagctggtgctggtgcaggttacggacaaggtgcaggagca
ggagctggtgccggtgcagggtatggcgctggagcaggttctggagctggagctggcgctgg
ctacggtgcaggtgctggttcaggagctggtgcaggttctggtgcaggagctggtgctggag
caggttacggtcaaggtgctggagctggagctggcgccggctatggtgcaggtgctggttct
ggagctggtgcaggctctggtgcaggagctggatcaggagctggagctggttcaggctatgg
cgcaggagctggttcaggagctggcgctggcgcaggttatggacaaggtgccggagcaggtg
ctggtgcaggtgcaggctatggtgcaggagcaggttctggagctggaactggtgcaggctat
ggtgctggtgcaggtgcaggatatggtgctggtgcaggtgcaggagctggttcaggagcagg
tgccggggcaggttatggtgctggtgctggtgcaggcgctggagcaggctatggtgctggag
ctggttccggascaggtgcaggarcaggttatggtgctggtgcaggtgcaggttcaggtgta
ggagcaggtgctggagctggtgctggagcaggatatggagctggagcaggtgcaggagcagg
ctatggtgctggtgcaggtgcaggtgctggtgctggtgcaggagcaggatatggcgctggag
caggtgcaggtgcttctgtaagttccactgtatctaacactgcttccagaatgtcttcagag
aatacatcacgtcgtgtttcttcagccatttcaagcattgtcggctctggtggagttaacat
gaattctctttcaaacgtaatctctaatgtatcatcgagcgttgctgcatctaatcctggac
tgtctggatgtgaagttcttgttcaaaccctgttggaagtagtatctgcattggttcacatt
ttgagctatgcaagtgtgggtagtgttgatgccagcgctgctggtcagtcagcccagactgt
agctacagccatgagtagtgtaatggggttgaattactttgacctttcaatattttttgaagac
tttatgttgttacttttgaattacgtaatgtctgaaaaataagataaataaatagaagtat
atatgcnaaaaaaaaaaaaaaaaaaaaaaaaaaaaa
```

Amino acid sequence of Phidippus andax fibroin 1 (SEQ ID NO: 16)

```
AGAGAGYGAGAGSGAGAGSGAGAGAGAGAGAGYGAGAGSGAGAGAGYGRGAGAGAGAG
YGQGAGAGAGAGYGAGAGSGAGAGYGTGAGSGAGSGAGSGAGSGAGAGAGAGYGAGAG
SGAGAGAGYGRGAGAGAGAGYGQGAGAGAGAGAGSGAGAGSGAGAGAGAGYGQGAGAG
AGAGYGAGAGSGAGAGAGYGAGAGSGAGAGSGAGAGAGYGQGAGAGAGAGYGAGAGSG
AGAGSGAGAGSGAGAGSSYGAGAGSGAGAGAGYGQGAGAGAGAGYGAGAGSGAGTGAGYG
AGAGAGYGAGAGAGAGSGAGAGAGYGAGAGAGAGYGAGAGSGXGAGXGYGAGAGAGSGVG
AGAGAGAGAGYGAGAGAGAGYGAGAGAGAGAGAGYGAGAGAGASVSSTVSNTASRMSSEN
TSRRVSSAISSIVGSGGVNMNSLSNVISNVSSSVAASNPGLSGCEVLVQTLLEVVSALVHIL
SYASVGSVDASAAGQSAQTVATAMSSVMG*
```

Figure 11

Zorocrates sp. fibroin 1 mRNA, partial cds. DNA sequence (845 bp; SEQ ID NO: 6)

ggtgcagcagccgcagcctcagcagcagcagcaggcggacgaggaagccaaggaggttacgg
agatgacggtggtgcagcagcagcagcagcagcagcagcggcggcagccgcggcaggaagtg
gtggaaccggaggaggacaaggggggcgcggagatggaggtgcggcagcagcagcagcagca
gccgcagaggccgcagcaggtggaaaaggaagacaaggaagttacggagatgacggtggtgc
agcagtagcagcagcagctgcagcggcagcagcggcaggaagaggtggttccggaagaggac
aaggacttcgtagagataaaggaagttacggagttgacggtggtgcagaagcagcagcatcc
gcagcggccacagcaggcagacaaggaagacaaggaagttacggagatgacggtggtgcagc
agcagcagcagcagcggcttctgcttcacggttagcctcctcttctgctgtttctcgag
tctcatctgctgtttctgcgctgttgtcaaatggcttttctgatgtaaattccctctccaac
gtgatttctggactttctgcttctgtatcttcttccacacctgagctgactggttgcgaagt
tctcgtggaagtccttttggaagtagtatcagctttggttcatattttgaactttgctgaca
ttggaaacgttaatattagtgcttcaggtgattccacatcccttgtaggccgaactgtttta
gaagcctttggctgaaatattactctattccttttttttttttgaatattgtttcagctttt
aactgtgacataaaaatgttatataaggaataaatata Amino acid sequence of Zorocrates sp. fibroin 1 (SEQ ID NO: 17)

GAAAAASAAAAGGRGSQGGYGDDGGAAAAAAAAAAAAAAGSGGTGGGQGGRGDGGAAAAAAA
AAEAAAGGKGRQGSYGDDGGAAVAAAAAAAAAAGRGGSGRGQGLRRDKGSYGVDGGAEAAAS
AAATAGRQGRQGSYGDDGGAAAAAAAASASRLASSSAVSRVSSAVSALLSNGFSDVNSLSN
VISGLSASVSSSTPELTGCEVLVEVLLEVVSALVHILNFADI
GNVNISASGDSTSLVGRTVLEAFG*

Fig. 12A

Kukulcania hibernalis cDNA-1

Sequence Range: 1 to 2282

```
             10              20              30              40
              *               *               *               *
GCT GGT TCC TCA GGC GAT GGT GCG TCA GCA GCG GCT TCT GCT GCA GCT
 A   G   S   S   G   D   G   A   S   A   A   A   S   A   A   A>

50              60              70              80              90
  *               *               *               *               *
GCT GCT GGA GCA GGT TCT GGA AGA CGA GGA CCA GGA GGC GCT AGA TCT
 A   A   G   A   G   S   G   R   R   G   P   G   G   A   R   S>

100             110             120             130             140
     *               *               *               *               *
CGC GGA GGA GCT GGT GCT GGT GCT GGT GCC GGA TCT GGA GTA GGA GGC
 R   G   G   A   G   A   G   A   G   A   G   S   G   V   G   G>

150             160             170             180             190
        *               *               *               *               *
TAT GGT TCT GGA TCA GGT GCT GGT GCT GGC GCG GGT GCT GGG GCA GGC
 Y   G   S   G   S   G   A   G   A   G   A   G   A   G   A   G>

200             210             220             230         240
           *               *               *               *           *
GCA GGT GGT GAA GGA GGT TTT GGT GAA GGC CAG GGC TAT GGA GCA GGT
 A   G   G   E   G   G   F   G   E   G   Q   G   Y   G   A   G>

250             260             270             280
              *               *               *               *
GCT GGA GCA GGA TAT GGC GCT GGC CGT GCA GGC GGT AGA GGC CGT GGT
 A   G   A   G   Y   G   A   G   R   A   G   G   R   G   R   G>

290             300             310             320             330
 *               *               *               *               *
GGA CGT GGT GGA GAA GCT TTC TCT GCT TCT TCA GCT TCT AGT GCA GTT
 G   R   G   G   E   A   F   S   A   S   S   A   S   S   A   V>

340             350             360             370             380
    *               *               *               *               *
GTT TTT GAA TCG GCA GGT GCT GGT GCA GGT GCA GGT TTT GGT GTT GGA
 V   F   E   S   A   G   A   G   A   G   A   G   F   G   V   G>

390             400             410             420             430
       *               *               *               *               *
GCT GGT GCC GGT GCT GGA GCA GGA GCA GGT TTT GGT TCT GGA GCT GGT
 A   G   A   G   A   G   A   G   A   G   F   G   S   G   A   G>
```

Fig. 12B

```
        440            450            460            470            480
         *              *              *              *              *
GCG GGA TCA GGT GCT GGA GCA GGA TAT GGC GCT GGC CGT GCA GGC GGT
 A   G   S   G   A   G   A   G   Y   G   A   G   R   A   G   G>

490            500            510            520
         *              *              *              *
AGA GGC CGT GGT GGA CGT GGT GGA GAA GCT TTC TCT GCT TCT TCA GCT
 R   G   R   G   G   R   G   G   E   A   F   S   A   S   S   A>

530            540            550            560            570
  *              *              *              *              *
TCT AGT GCA GTT GTT TTT GAA TCG GCA GGT CCA GGC GAA GAA GCT GGT
 S   S   A   V   V   F   E   S   A   G   P   G   E   E   A   G>

580            590            600            610            620
     *              *              *              *              *
TCC TCA GGC GAT GGT GCG TCA GCA GCG GCT TCT GCT GCA GCG GCT GCT
 S   S   G   D   G   A   S   A   A   A   S   A   A   A   A   A>

630            640            650            660            670
         *              *              *              *              *
GGA GCA GGT TCT GGA AGA CGA GGA CCA GGA GGC GCT AGA TCT CGC GGA
 G   A   G   S   G   R   R   G   P   G   G   A   R   S   R   G>

680            690            700            710            720
         *              *              *              *              *
GGA GCT GGT GCT GGT GCT GGT GCC GGA TCC GGA GTA GGA GGC TAT GGT
 G   A   G   A   G   A   G   A   G   S   G   V   G   G   Y   G>

730            740            750            760
             *              *              *              *
TCT GGA TCA GGT GCT GGT GCT GGC GCG GGT GCT GGG GCA GGC GCA GGT
 S   G   S   G   A   G   A   G   A   G   A   G   A   G   A   G>

770            780            790            800            810
  *              *              *              *              *
GGT GAA GGA GGT TTT GGT GAA GGC CAG GGC TAT GGA GCA GGT GCT GGG
 G   E   G   G   F   G   E   G   Q   G   Y   G   A   G   A   G>

820            830            840            850            860
     *              *              *              *              *
GCA GGC TTT GGC TCT GGC GCA GGT GCT GGA GCT GGA GCA GGT TCG GGT
 A   G   F   G   S   G   A   G   A   G   A   G   A   G   S   G>

870            880            890            900            910
         *              *              *              *              *
GCA GGT GCA GGA GAA GGC GTT GGT TCT GGC GCA GGT GCT GGT GCA GGT
 A   G   A   G   E   G   V   G   S   G   A   G   A   G   A   G>

920            930            940            950            960
         *              *              *              *              *
GCA GGT TTT GGT GTT GGA GCT GGT GCC GGT GCT GGA GCA GGA GCA GGT
 A   G   F   G   V   G   A   G   A   G   A   G   A   G   A   G>

970            980            990           1000
             *              *              *              *
TTT GGT TCT GGA GCT GGT GCG GGA TCA GGT GCT GGA GCA GGA TAT GGC
 F   G   S   G   A   G   A   G   S   G   A   G   A   G   Y   G>

```
              *                   *                   *                   *                   *
          GCT GGC CGT GCA GGC GGT AGA GGC CGT GGT GGA CGT GGT GGA GAA GCT
           A   G   R   A   G   G   R   G   R   G   G   R   G   G   E   A>

1060        1070        1080        1090        1100
           *           *           *           *           *
          TTC TCT GCT TCT TCA GCT TCT AGT GCA GTT GTT TTT GAA TCG GCA GGT
           F   S   A   S   S   A   S   S   A   V   V   F   E   S   A   G>

1110        1120        1130        1140        1150
           *           *           *           *           *
          CCA GGC GAG GAA GCT GGT TCC TCA GGC GGT GGT GCG TCA GCA GCG GCT
           P   G   E   E   A   G   S   S   G   G   G   A   S   A   A   A>

1160        1170        1180        1190        1200
           *           *           *           *           *
          TCT GCT GCA GCG GCT GCT GGA GCA GGT TCT GGA AGA CGA GGA CCA GGA
           S   A   A   A   A   A   G   A   G   S   G   R   R   G   P   G>

1210        1220        1230        1240
                *           *           *           *
          GGC GCT AGA TCT CGC GGA GGA GCT GGT GCT GGT GCT GGT GCC GGA TCC
           G   A   R   S   R   G   G   A   G   A   G   A   G   A   G   S>

1250        1260        1270        1280        1290
       *           *           *           *           *
      GGA GTA GGA GGC TAT GGT TCT GGA TCA GGT GCT GGA GCT GGC GCG GGT
       G   V   G   G   Y   G   S   G   S   G   A   G   A   G   A   G>

1300        1310        1320        1330        1340
           *           *           *           *           *
          GCT GGG GCA GGC GCA GGT GGT GAA GGA GGT TTT GGT GAA GGC CAG GGC
           A   G   A   G   A   G   G   E   G   G   F   G   E   G   Q   G>

1350        1360        1370        1380        1390
                *           *           *           *           *
          TAT GGA GCA GGT GCT GGG GCA GGC TTT GGC TCT GGC GCA GGT GCT GGA
           Y   G   A   G   A   G   A   G   F   G   S   G   A   G   A   G>

1400        1410        1420        1430        1440
                *           *           *           *           *
          GCT GGA GCA GGT TCG GGT GCA GGT GCA GGA GAA GGC GTT GGT TCT GGC
           A   G   A   G   S   G   A   G   A   G   E   G   V   G   S   G>

1450        1460        1470        1480
                     *           *           *           *
          GCA GGT GCT GGT GCA GGT GCA GGT TTT GGT GTT GGA GCT GGT GCC GGT
           A   G   A   G   A   G   A   G   F   G   V   G   A   G   A   G>

1490        1500        1510        1520        1530
       *           *           *           *           *
      GCT GGA GCA GGA GCA GGT TTT GGT TCT GGA GCT GGT GCG GGA TCA GGT
       A   G   A   G   A   G   F   G   S   G   A   G   A   G   S   G>

1540        1550        1560        1570        1580
           *           *           *           *           *
          GCT GGA GCA GGA TAT GGC GCT GGC CGT GCA GGC GGT AGA GGC CGT GGT
           A   G   A   G   Y   G   A   G   R   A   G   G   R   G   R   G>

1590        1600        1610        1620        1630
           *           *           *           *           *
          GGA CGT GGT GGA GAA GCT TTC TCT GCT TCT TCA GCT TCT AGT GCA GTT
           G   R   G   G   E   A   F   S   A   S   S   A   S   S   A   V>
```

Fig. 12D

```
      1640           1650           1660           1670           1680
       *              *              *              *              *
GTT TTT GAA TCG GCA GGT CCA GGC GAG GAA GCT GGT TCC TCA GGC GGT
 V   F   E   S   A   G   P   G   E   E   A   G   S   S   G   G>

1690           1700           1710           1720
            *              *              *              *
GGT GCG TCA GCA GCG GCT TCT GCT GCA GCG GCT GCT GGA GCA GGT TCT
 G   A   S   A   A   A   S   A   A   A   A   A   G   A   G   S>

1730           1740           1750           1760           1770
 *              *              *              *              *
GGA AGA CGA GGA CCA GGA GGC GCT AGA TCT CGC GGA GGA GCT GGT GCT
 G   R   R   G   P   G   G   A   R   S   R   G   G   A   G   A>

1780           1790           1800           1810           1820
     *              *              *              *              *
GGT GCT GGT GCC GGA TCC GGA GTA GGA GGC TAT GGT TCT GGA TCA GGT
 G   A   G   A   G   S   G   V   G   G   Y   G   S   G   S   G>

1830           1840           1850           1860           1870
         *              *              *              *              *
GCT GGT GCT GGC GCG GGT GCT GGG GCA GGC GCA GGT GGT GAA GGA GGT
 A   G   A   G   A   G   A   G   A   G   A   G   G   E   G   G>

1880           1890           1900           1910           1920
             *              *              *              *              *
TTT GGT GAA GGC CAG GGC TAT GGA GCA GGT GCT GGA GCC GGA GCA GGT
 F   G   E   G   Q   G   Y   G   A   G   A   G   A   G   A   G>

1930           1940           1950           1960
                 *              *              *              *
GCT GGG GCA GGC TTT GGC TCT GGC GCA GGT GCT GGA GCT GGA GCA GGT
 A   G   A   G   F   G   S   G   A   G   A   G   A   G   A   G>

1970           1980           1990           2000           2010
 *              *              *              *              *
TCG GGT GCA GGT GCA GGA GAA GGC GTT GGT TCT GGC GCA GGT GCT GGT
 S   G   A   G   A   G   E   G   V   G   S   G   A   G   A   G>

2020           2030           2040           2050           2060
     *              *              *              *              *
GCA GGT GCA GGT TTT GGT GTT GGA GCT GGT GCC GGT GCT GGA GCA GGA
 A   G   A   G   F   G   V   G   A   G   A   G   A   G   A   G>

2070           2080           2090           2100           2110
         *              *              *              *              *
GCA GGT TTT GGT TCT GGA GCT GGT GCG GGA TCA GGT GCT GGA GCA GGA
 A   G   F   G   S   G   A   G   A   G   S   G   A   G   A   G>

2120           2130           2140           2150           2160
             *              *              *              *              *
TAT GGC GCT GGC CGT GCA GGC GGT AGA GGC CGT GGT GGA CGT GGT GGA
 Y   G   A   G   R   A   G   G   R   G   R   G   G   R   G   G>

2170           2180           2190           2200
                 *              *              *              *
GAA GCT TTC TCT GCT TCT TCA GCT TCT AGT GCA GTT GTT TTT GAA TCG
```

Fig. 12E

```
      E    A    F    S    A    S    S    A    S    S    A    V    V    F    E    S>
    2210           2220           2230           2240           2250
      *              *              *              *              *
     GCA  GGT  CCA  GGC  GAG  GAA  GCT  GGT  TCC  TCA  GGC  GAT  GGT  GCG  TCA  GCA
      A    G    P    G    E    E    A    G    S    S    G    D    G    A    S    A>

2260           2270           2280
      *              *              *
     GCG  GCT  TCT  GCT  GCA  GCG  TCT  GCT  GG        (SEQ ID NO: 7)
      A    A    S    A    A    A    S    A    G>       (SEQ ID NO: 18)
```

Fig. 13A

*Kukulcania* cDNA-2

Sequence Range: ~ 2.5 kb

```
              10           20           30           40
               *            *            *            *
GGA TCT GGC TCA GGT TCT GGA TCT GGC TCA GGT TCT GGT TCT GGT ACA
 G   S   G   S   G   S   G   S   G   S   G   S   G   S   G   T>

50           60           70           80           90
    *            *            *            *            *
GGT TCT GGA TCT GGT GCA GGC TCT GGA TCA GGG GCA GGC TCT GGA TCA
 G   S   G   S   G   A   G   S   G   S   G   A   G   S   G   S>

100          110          120          130          140
     *            *            *            *            *
GGA GCA GGC TCT GGA TCA GGA GCA GGC TCT GGA TCA GGA GCA GGC TCT
 G   A   G   S   G   S   G   A   G   S   G   S   G   A   G   S>

150          160          170          180          190
     *            *            *            *            *
GGT GCA GGC TCA GGT GCT GGG TCA GGA TCA GGT AAT GGT TAC GGA GGA
 G   A   G   S   G   A   G   S   G   S   G   N   G   Y   G   G>

200          210          220          230          240
         *            *            *            *            *
GGA TTT GGA ATA GGT TAC GGT AAC CAA CAA GGA TAT GGA GCA GGT TTC
 G   F   G   I   G   Y   G   N   Q   Q   G   Y   G   A   G   F>

250          260          270          280
           *            *            *            *
GGA CAA GGA TCT GGG GCA GGT TCT GGA TCG GGC TCA GGT TCT GGT TCT
 G   Q   G   S   G   A   G   S   G   S   G   S   G   S   G   S>

290          300          310          320          330
  *            *            *            *            *
GGT GCA GGT TCT GGA TCT GGC TCA GGT TCT GGT TCT GGA TCT GGC GCA
 G   A   G   S   G   S   G   S   G   S   G   S   G   S   G   A>

340          350          360          370          380
      *            *            *            *            *
GGT TCT GGA TCA GGC TCT GGA TCT GGT TCA GGT GCA GGT TCC GGA TCA
 G   S   G   S   G   S   G   S   G   S   G   A   G   S   G   S>

390          400          410          420          430
        *            *            *            *            *
GGT TCT GGA TCG GGC TCA GGT TCT GGA TCG GGC TCA GGT TCT GGT TCT
 G   S   G   S   G   S   G   S   G   S   G   S   G   S   G   S>
```

Fig. 13B

```
            440             450             460             470             480
             *               *               *               *               *
GGT GCC AGT TCT GGA TCT GGC GCA GGT TCT GGT TTT GGC CCA GGT TCT
 G   A   S   S   G   S   G   A   G   S   G   F   G   P   G   S>

490             500             510             520
             *               *               *               *
GGA TCA AGT TCA AGC CCA AGT TCT GGG GCA AGC TCA GGG GCT GGT TCC
 G   S   S   S   S   P   S   S   G   A   S   S   G   A   G   S>

530             540             550
  *               *               *
AGA TCA GGT AAG GGT TTT GGA GGG AGA --- --- --- --- --- --- ---
 R   S   G   K   G   F   G   G   R 1850            1860            1870            1880
             *               *               *               *
GGA TAT GGA GCA GGG TTC GGA CAA GGA TCT GGG GCA GGT TCT GGA TCG
 G   Y   G   A   G   F   G   Q   G   S   G   A   G   S   G   S>

1890            1900            1910            1920            1930
 *               *               *               *               *
GCT TCA GGT TCT GGT TCT GGT GCA GGT TCT GGA TCT GGC TCA GGT TCT
 A   S   G   S   G   S   G   A   G   S   G   S   G   S   G   S>

1940            1950            1960            1970            1980
  *               *               *               *               *
GGT TCT GGA TCT GGC GCA GGT TCT GGA TCA GGC TCT GGA TCT GGT TCA
 G   S   G   S   G   A   G   S   G   S   G   S   G   S   G   S>

1990            2000            2010            2020            2030
        *               *               *               *               *
GGT GCA GGT TCC GGA TCA GGT TCT GGA TCG GGC TCA GGT TCT GGA TCG
 G   A   G   S   G   S   G   S   G   S   G   S   G   S   G   S>

2040            2050            2060            2070            2080
             *               *               *               *               *
GGC TCA GGT TTT GGT TCT GGT GCA GGT TCT GGA TCT GGC GCA GGT TCT
 G   S   G   F   G   S   G   A   G   S   G   S   G   A   G   S>

2090            2100            2110            2120
             *               *               *               *
GGT TCT GGC GCA GGT TCT GGA TCA GGT TCA GGC GCA GGT TCT GGT GCA
 G   S   G   A   G   S   G   S   G   S   G   A   G   S   G   A>

2130            2140            2150            2160            2170
 *               *               *               *               *
GGC TCA GGT GCT GGT TCA GGA TCA GGT AAT GGT TAT GGA GGA GGA TAT
 G   S   G   A   G   S   G   S   G   N   G   Y   G   G   G   Y>

2180            2190            2200            2210            2220
        *               *               *               *               *
GGA ATA GGT TCT AGT TAC CAA GGA TAT GGA ACA GGT TTC GGG CAA GGA
 G   I   G   S   S   Y   Q   G   Y   G   T   G   F   G   Q   G>

2230            2240            2250            2260            2270
             *               *               *               *               *
GCT GGC GCA GGT TCT GGA TCT GGT TCA GGT GCA GGT TCG GGA TCA GGT
 A   G   A   G   S   G   S   G   S   G   A   G   S   G   S   G>
```

Fig. 13C

```
       2280              2290              2300              2310              2320
         *                 *                 *                 *                 *
    TCT GGA TCG GGC TCA GGC TCT GGA TCT GGC TCA GGT TCT GGA TCT GGC
     S   G   S   G   S   G   S   G   S   G   S   G   S   G   S   G>

2330              2340              2350              2360
                *                 *                 *                 *
    TCA GGT TCT GGC TCT GGT GCA GGT TCT GGA TCT GGC GCA GGC TTT GGA
     S   G   S   G   S   G   A   G   S   G   S   G   A   G   F   G>

2370              2380              2390              2400              2410
     *                 *                 *                 *                 *
    TCA GGA GCA GGC TCT GGT GCA GGT TCG GGT GCA GGC TCA GGT GCT GGG
     S   G   A   G   S   G   A   G   S   G   A   G   S   G   A   G>

2420              2430              2440              2450              2460
         *                 *                 *                 *                 *
    TCA GGA TCT GGT AAT GGT TAT GGA GGA GGT TAT GGA ATA GGT TAC GGT
     S   G   S   G   N   G   Y   G   G   G   Y   G   I   G   Y   G>

2470              2480
         *                 *
    TAC CAA CAA GGA TAT GGA GC      (SEQ ID NO: 8)
     Y   Q   Q   G   Y   G   A>     (SEQ ID NO: 19)
```

Figure 14

Kukulcania cDNA-3

Sequence Range: 1 to 314

```
              10            20            30            40
               *             *             *             *
      GGA GCT GGT GTC GGA GTT GGT GCT AGT GTC GGA GTT GGT GCT GGT GTC
       G   A   G   V   G   V   G   A   S   V   G   V   G   A   G   V>

50            60            70            80            90
           *             *             *             *             *
      GGA GTT GGT GTT GGT GTC GCC GCC GGT GCT GGT GCC GCC GCC GGC GCT
       G   V   G   V   G   V   A   A   G   A   G   A   A   A   G   A>

100           110           120           130           140
           *             *             *             *             *
      GGC GCC GGT GCT GGG GCT GGT GGC GGT GCC GGA GCT GGA GCT GGT GCC
       G   A   G   A   G   A   G   G   G   A   G   A   G   A   G   A>

150           160           170           180           190
           *             *             *             *             *
      GGA GCT GGT GCT GGT GCT GGA GCT GGT GCT GGC GCT GGT GCT GGA GCT
       G   A   G   A   G   A   G   A   G   A   G   A   G   A   G   A>

200           210           220           230           240
           *             *             *             *             *
      GGA GTC GGA GTT GGT ATC GGA ATC GGT GCT GGA GCT GGT GCT GGT GCT
       G   V   G   V   G   I   G   I   G   A   G   A   G   A   G   A>

250           260           270           280
           *             *             *             *
      GGA GCT GGT GCT GGA GCT GGT GCT GGA GCT GGT GCT GGT GCC GAA GCT
       G   A   G   A   G   A   G   A   G   A   G   A   G   A   E   A>

290           300           310
       *             *             *
      GGT GTC GGA GTT GGT GTC GGA GTT GG       (SEQ ID NO: 9)
       G   V   G   V   G   V   G   V   G>     (SEQ ID NO: 20)
```

Fig. 15A

Argiope trifasciata MiSp 1

Sequence Range: 1 to 1682

```
              10              20              30              40
              *               *               *               *
ATC GGA TAT GGA CGT GGT GCT GGT GCA GGA GCA GGC GCT GCA GCA GCG
 I   G   Y   G   R   G   A   G   A   G   A   G   A   A   A   A>

50              60              70              80              90
  *               *               *               *               *
GCT GGT GCT GGA GCC GGA GCT GGA GCA GCA GGT GGA TAT GGG GGA GGA
 A   G   A   G   A   G   A   G   A   A   G   G   Y   G   G   G>

100             110             120             130             140
     *               *               *               *               *
TAC GGA ATT GGA GCT GGA GCC GGT GCA AGT GCC GGA GCT GGT GCC GGT
 Y   G   I   G   A   G   A   G   A   S   A   G   A   G   A   G>

150             160             170             180             190
        *               *               *               *               *
GGA GCA GGC GGA TAT GGA CGT GGT GCT GGT GCA GGA GCA GGA GCT GCA
 G   A   G   G   Y   G   R   G   A   G   A   G   A   G   A   A>

200             210             220             230             240
           *               *               *               *               *
GCA GCA GCT GGT GCT GGA GCT GGA GCA GCA GGT GGA TAT GGT GGA GGA
 A   A   A   G   A   G   A   G   A   A   G   G   Y   G   G   G>

250             260             270             280
              *               *               *               *
TAC GGA GGT GGA GCT GGA GAC GGT GCT GGA GCA GGA GCC GGT GCT GGA
 Y   G   G   G   A   G   D   G   A   G   A   G   A   G   A   G>

290             300             310             320             330
 *               *               *               *               *
GCA GGA GCT GGT GCC GGT AGT GCA GGC GGA TAT GGA CGT GGT GCA GGT
 A   G   A   G   A   G   S   A   G   G   Y   G   R   G   A   G>

340             350             360             370             380
    *               *               *               *               *
GCA GGA GCA GGC GCT GCA GCA GCG GCT GGT GCT GGA GCC GGA GCT GGA
 A   G   A   G   A   A   A   A   A   G   A   G   A   G   A   G>

390             400             410             420             430
          *               *               *               *               *
GCA GCA GGT GGA TAT GGT GGA GGA TAC GGA ATT GGA GCT GGA GCC GGT
 A   A   G   G   Y   G   G   G   Y   G   I   G   A   G   A   G>
```

Fig. 15B

```
        440             450             460             470             480
         *               *               *               *               *
GCA AGT GCC GGA GCT GGT GCC GGT GGA GCA GGC GGA TAT GGA CGT GGT
 A   S   A   G   A   G   A   G   G   A   G   G   Y   G   R   G>

490             500             510             520
             *               *               *               *
GCT GGT GCA GGA GCA GGA GCA GGC GCT GCA GCA GCA GCT GGT GCT GGT
 A   G   A   G   A   G   A   G   A   A   A   A   G   A   G>

530             540             550             560             570
  *               *               *               *               *
GCC GGA GCT GGA GCA GCA GGG GGA TAT GGT GGA GGA TAC GGA GCT GGA
 A   G   A   G   A   A   G   G   Y   G   G   G   Y   G   A   G>

580             590             600             610             620
     *               *               *               *               *
GCT GGA ACC GGT GCT GGA GCA GGA GCT GGT GCC GGT GTA GCA GGC GGA
 A   G   T   G   A   G   A   G   A   G   A   G   V   A   G   G>

630             640             650             660             670
         *               *               *               *               *
TAT CGA CGT GGT TCT GGT GCA GGA GCA GGC GCT GCA GCA GCG GCT GGT
 Y   R   R   G   S   G   A   G   A   G   A   A   A   A   G>

680             690             700             710             720
             *               *               *               *               *
GCT GGA GCC GGA GCT GGA GCA GCA GGT GGA TAT GGT GGA GGA TAC GGA
 A   G   A   G   A   G   A   A   G   G   Y   G   G   G   Y   G>

730             740             750             760
                 *               *               *               *
ATT GGA GCT GGA GCC GGT GCA GGT TCA GGA GCT GGA GCC GGT GCA GGA
 I   G   A   G   A   G   A   G   S   G   A   G   A   G   A   G>

770             780             790             800             810
  *               *               *               *               *
GCA GGA GCT GGT GCC GGT GGA GCA GGC GGA TAT GGA CGT GGT GCA GGT
 A   G   A   G   A   G   G   A   G   G   Y   G   R   G   A   G>

820             830             840             850             860
     *               *               *               *               *
GCA GGA GCA GGC GCT GCA GCA GCG GCT GGT GCT GGT GCA GGT GCC GGT
 A   G   A   G   A   A   A   A   G   A   G   A   G   A   G>

870             880             890             900             910
         *               *               *               *               *
GGA GCA GGC GGC TAT GGA CGT GGT GCT GGT GCA GGA GCA GGC GCT GCA
 G   A   G   G   Y   G   R   G   A   G   A   G   A   G   A   A>

920             930             940             950             960
             *               *               *               *               *
GCT GCG GCT GGA ACC GGT GCT GGA GCA GCA GGT GGA TAT GGT GGA GGA
 A   A   A   G   T   G   A   G   A   A   G   G   Y   G   G   G>

970             980             990            1000
                 *               *               *               *
TAC GGA GGT GGA GCT GGA GCG GGT GTA GGT GCA GGA GCA GGA GCC GGT
 Y   G   G   G   A   G   A   G   V   G   A   G   A   G   A   G>
```

Fig. 15C

```
        1010              1020              1030              1040              1050
          *                 *                 *                 *                 *
GGA GCA GGC GGA TAT GGA CGT GGT GCA GGA GCA GGA GCA GGC GCT GCA
 G   A   G   G   Y   G   R   G   A   G   A   G   A   G   A   A>

1060              1070              1080              1090              1100
          *                 *                 *                 *                 *
GCA GCG GCT AGT GCT GGT GCC GGA GCA GGA GGA TAT GGT GGA GGA TAC
 A   A   A   S   A   G   A   G   A   G   G   Y   G   G   G   Y>

1110              1120              1130              1140              1150
          *                 *                 *                 *                 *
GGA GTC GCA GGT GGA AGT AGT ATT TCA TAC GGC GCA ACA AGT AGT TCA
 G   V   A   G   G   S   S   I   S   Y   G   A   T   S   S   S>

1160              1170              1180              1190              1200
          *                 *                 *                 *                 *
GCA ACG TCA TCG AGC ACA GCA TCT TCT AGT AGA TCT GGC ATA GTT ACA
 A   T   S   S   S   T   A   S   S   S   R   S   G   I   V   T>

1210              1220              1230              1240
          *                 *                 *                 *
TCT GGT GGA TAT GGA GCA GGT GCT GCC GCA GGG GCT GGA GCA GGT GCC
 S   G   G   Y   G   A   G   A   A   A   G   A   G   A   G   A>

1250             1260              1270              1280              1290
   *                *                 *                 *                 *
GCT GCC GGA GCT GGT TCA TAT AGT GGT TCG ATT AGT CGC TTG TCT AGC
 A   A   G   A   G   S   Y   S   G   S   I   S   R   L   S   S>

1300             1310              1320              1330              1340
   *                *                 *                 *                 *
GCT GAA GCC GTG AAC AGA GTT TCT TCT AAC ATA GGA GCT GTC GCA TCT
 A   E   A   V   N   R   V   S   S   N   I   G   A   V   A   S>

1350              1360              1370              1380              1390
          *                 *                 *                 *                 *
GGA GGT GCA TCC GCC CTT CCT GGC GTA ATT TCA AAC ATT TTC TCT GGA
 G   G   A   S   A   L   P   G   V   I   S   N   I   F   S   G>

1400              1410              1420              1430              1440
          *                 *                 *                 *                 *
GTG AGT TCT TCG GCT GGC TCC TAT GAA GAA GCG GTT ATC CAA TCT CTT
 V   S   S   S   A   G   S   Y   E   E   A   V   I   Q   S   L>

1450              1460              1470              1480
                *                 *                 *                 *
TTG GAA GTT CTT TCT GTT CTG CTT CAT ATA TTG AGC AAT TCT TCC ATC
 L   E   V   L   S   V   L   L   H   I   L   S   N   S   S   I>

1490             1500              1510              1520              1530
   *                *                 *                 *                 *
GGC TAT GTT GGG GCG GAA GGA TTA GGA GAT TCA TTG GCA GTT GTA CAG
 G   Y   V   G   A   E   G   L   G   D   S   L   A   V   V   Q>

1540              1550              1560              1570              1580
          *                 *                 *                 *                 *
CAA GCC GTA GGA CCT GTT GTC GGT TAA CTC AAA TGA TGA TCT TGA GCC
 Q   A   V   G   P   V   V   G   *  (SEQ ID NO: 21)
```

Fig. 15D

```
      1590          1600          1610          1620          1630
         *             *             *             *             *
GTG TAA AAC ATA AAC TTA ATA GTT TAT CTT CTG TAT TTT TAT TGT TAT 1640          1650          1660          1670          1680
         *             *             *             *             *
TTC TAA TTA AGA GAA ATA AAT TTC GCA TGT TTT GAA AAA AAA AAA AAA

AA      (SEQ ID NO: 10)
```

Fig. 16A

*Argiope* MiSp 2

Sequence Range: 1 to 681

```
            10              20              30              40
             *               *               *               *
    TCT GGA TAT GGA GCT GGA GCA GGT GGA TCT GGT GCT GGA GCA GGT TCA
     S   G   Y   G   A   G   A   G   G   S   G   A   G   A   G   S>

50              60              70              80              90
     *               *               *               *               *
    GTG GCT GGA TCT GCA TAC GGA AGA GGA TTT GCG TTA GCT GCG GCA GCA
     V   A   G   S   G   Y   G   R   G   F   A   L   A   A   A   A>

100             110             120             130             140
        *               *               *               *               *
    GGA TCT GGT GCT GGA GCA GCG TCT CGA GCT GGA TAT GGA GCT GGA GCA
     G   S   G   A   G   A   A   S   R   A   G   Y   G   A   G   A>

150             160             170             180             190
        *               *               *               *               *
    GGA TCT GGT GCT GGA GCA GGT TCA GGT GCA GGA GCA GGA TCA GGT TCT
     G   S   G   A   G   A   G   S   G   A   G   A   G   S   G   S>

200             210             220             230         240
             *               *               *               *           *
    GGA GCT GGA TAT GGA GTA GGA GCA GGA TCT GGT GCT GGA GCA GGT TCA
     G   A   G   Y   G   V   G   A   G   S   G   A   G   A   G   S>

250             260             270             280
            *               *               *               *
    GGT GCA GGA GCT GGA TAT GGA GCT GGA GCA GGA TCT GGT GCT GGA GCA
     G   A   G   A   G   Y   G   A   G   A   G   S   G   A   G   A>

290             300             310             320             330
     *               *               *               *               *
    GGT TCA GGT GCT GGA GCA GGT TCA GGA GCT GGA TCT GGA TAC GGA AGA
     G   S   G   A   G   A   G   S   G   A   G   S   G   Y   G   R>

340             350             360             370             380
        *               *               *               *               *
    GGA TTT GGA GCT GGA GCC GGA TCT GGT GCT GGA GCA GGT TCT GGA GCT
     G   F   G   A   G   A   G   S   G   A   G   A   G   S   G   A>

390             400             410             420             430
        *               *               *               *               *
    GGA TAT GGA GCT GGA GCA GGA TCT GGT GCT GGA GCA GGT TCA GGT GCA
     G   Y   G   A   G   A   G   S   G   A   G   A   G   S   G   A>

```
              *                   *                   *                   *                   *
    GGA GCA GGA TCA GGT TCT GGA GCT GGA TAT GGA GTA GGA GCA GGA TCT
     G   A   G   S   G   S   G   A   G   Y   G   V   G   A   G   S>

490                 500                 510                 520
               *                   *                   *                   *
    GGT GCT GGA GCA GGT TCA GGT GCT GGA GCC GGA TCA GGG TCA GGA GCA
     G   A   G   A   G   S   G   A   G   A   G   S   G   S   G   A>

530                 540                 550                 560                 570
     *                   *                   *                   *                   *
    GGA TAC GGA AGA GGA TTT GGA GCT GGA GCC GGA TCT GGT GCT GGA GCA
     G   Y   G   R   G   F   G   A   G   A   G   S   G   A   G   A>

580                 590                 600                 610                 620
          *                   *                   *                   *                   *
    GGT TCA GGT GTA GGA GCC GGA TCA GGT TCT GGA GCT GGA TAT GGA AGA
     G   S   G   V   G   A   G   S   G   S   G   A   G   Y   G   R>

630                 640                 650                 660                 670
               *                   *                   *                   *                   *
    AGA TTT GGA GCT GGT GCT GGA TAT GGC GCA GGA TCA GGT GCT GGA GCT
     R   F   G   A   G   A   G   Y   G   A   G   S   G   A   G   A>

680
               *
    GGA TCT GGA          (SEQ ID NO: 11)
     G   S   G>          (SEQ ID NO: 22)
```

Figure 17

200 amino acid consensus repeat (SEQ ID NO: 23)

SSVVQRAAQSLASTLGVDGNNLARFAVQAVSRLPAGSDTSAYAQAFSSALFNAGVLNASNID
TLGSRVLSALLNGVSSAAQGLGINVDSGSVQSDISSSSSFLSTSSSSASYSQASASSTSGAG
YTGPSGPSTGPSGYPGPLGGGAPFGQSGFGGSAGPQGGFGATGGASAGLISRVANALANTST
LRTVLRTGVSQQIA

EXPRESSION OF SPIDER SILK PROTEINS

This application is a continuation application of U.S. application Ser. No. 10/479,638, filed May 5, 2004, now U.S. Pat. No. 7,288,391, issued Oct. 30, 2007, which is a §371 filing of PCT/US02/18256, filed Jun. 6, 2002, which in turn claims priority to U.S. Provisional Application No. 60/296,184, filed Jun. 6, 2001. Each of the foregoing applications is incorporated herein by reference as though set forth in full.

Pursuant to 35 U.S.C. §202(c) it is acknowledged that the U.S. Government has certain rights in the invention described herein, which was made in part with funds from the Army Research Office, Grant Number DAAG55-98-1-0262 and the National Science Foundation, Grant Number MCB-9806999.

FIELD OF THE INVENTION

The present invention relates to the fields of molecular biology and plant biology. Specifically, the invention is directed to the methods for expressing spider silk proteins in plants and the synthesis and purification of spider silk proteins therefrom.

BACKGROUND OF THE INVENTION

Several publications and patent documents are referenced in this application in order to more fully describe the state of the art to which this invention pertains. The disclosure of each of these publications and documents is incorporated by reference herein.

Plants may be viewed as model systems for the large-scale production of exogenous proteins intended for therapeutic and industrial applications. Many plants are relatively easy and inexpensive to grow and are routinely produced in large quantities. Such large quantities, or crops, are harvested and processed by standard procedures utilized by the agronomic industry. The effective use of plants as bioreactors or protein factories depends on the ability to achieve high levels of expression of exogenous protein, which is stable throughout the life cycle of the transgenic plant and whose expression is maintained in subsequent generations. Silencing of an introduced transgene may occur in transformed plants and, thus, contributes to the commercial risk involved and hampers the general economic exploitation of plants as protein factories. A number of efficient strategies have been developed to avoid transgene silencing, including careful design of the transgene construct and thorough analysis of transformants at the molecular level. Recent research has focused on additional aspects related to the generation of transgenic plants intended for protein production and their influence on the stability of heterologous gene expression (De Wilde et al. 2000. Plant Mol Biol 43:347-59).

Of note, clinical trials are proceeding on the first biopharmaceuticals derived from transgenic plants. One transgenic plant-derived biopharmaceutical, hirudin, has been commercially produced in Canada. Product purification may, however, present a potential obstacle in the process because it is expensive. Various methods have been developed to overcome this problem, including oleosin-fusion technology, which allows extraction with oil bodies. In some cases, delivery of a biopharmaceutical product by direct ingestion of the modified plant may potentially remove the need for product purification. Such biopharmaceuticals may be stored and distributed as, for example, seeds, tubers, fruits, or ground plant material. The stability of exogenous proteins expressed in plants provides an additional benefit of such systems. (Giddings et al. 2000. Nat Biotechnol 18:1151-5).

The presence of silk protein producing abdominal glands is a unique feature of spiders. Spiders are also unique in the use of these silks throughout their life span and their nearly total dependence on silk for evolutionary success (14, 19). There were periods of fairly intense study of spider silk prior to World War II and in the late 1950s. Progress was relatively meager, however, particularly when compared to that related to silkworm silk. Beginning in the 1970s, interest in spider silk was revived with several papers describing physical, mechanical and chemical properties of spider silks. The composition of spider silks has been known to be predominantly protein since the 1907 studies of Fischer (5). In fact, except for the sticky spiral thread, no significant amount of any other compound but protein has been detected.

Typical spider webs are constructed from several different silks, each of which is produced in a different gland. Due to their large size and ease of study, major ampullate glands have received the most attention. Thus, most of what is known about the synthesis of silk proteins is based on studies of major ampullate glands. Morphological and histochemical studies of the other glands, however, have confirmed the conclusions drawn from research performed using major ampullate glands. Synthesis of the silk protein(s) takes place in specialized columnar epithelial cells (2). There appear to be at least two different types of cells producing protein (14), which correlates with findings that revealed the presence of two proteins in the silk from these glands. Newly synthesized protein droplets within the cell are secreted into the lumen of the gland, which serves as a reservoir of soluble silk protein.

The protein in the lumen of the gland is believed to be in a liquid crystal state (21), a structure which prevents fiber formation prior to passage through a narrow duct leading to a spinnernet. Maintenance of the liquid crystal state is likely due to physical properties related to protein structure and concentration, which serve to prevent aggregation into large protein arrays. It has been shown that silk in the lumen is not birefringent whereas silk becomes increasingly birefringent as it passes down through the duct (22). Thus, the ordered array of protein observed in the final fiber occurs during its passage through the duct. This appears to be due to the mechanical and frictional forces aligning the protein molecules and altering the secondary structure to the final fiber form. Iizuka (13) has proposed a similar mechanism for silkworm silk formation. The ability to draw silk fibers directly from the lumen of the major, minor and cylindrical glands (Hinman, M. personal comm.) implies that the physical force of drawing the solution is sufficient for fiber formation and provides experimental evidence for this mechanism. Once the fiber has reached the spinneret, a muscular valve at the exit of the spinneret is utilized to control the flow rate of the fiber and, to a small degree the fiber diameter. The silk exits the spider through the spinnerets, of which there are three pairs, anterior, median and posterior.

One of the features attracting researchers to study spider silks is their unusual mechanical properties. Orb-web weaving spiders use the minimum amount of silk in their webs to catch prey. The web has to stop a rapidly flying insect nearly instantly in a manner that allows the prey to become entangled and trapped. To achieve this end, the web must absorb the energy of momentum of the moving insect without breaking. Moreover, the web must also possess mechanical properties that serve to retain the insect. Gosline et al. (8) have reviewed several aspects of this property and concluded that spider silk and the web are nearly optimally designed for each other.

The present inventors have tested major and minor ampullate and egg case silks from both *Nephila clavipes* and *Ara-*

*neus gemmoides* using standard mechanical testing methods (18). The silks were found to exceed the published data for tensile strength by a substantial margin. This was due to the use of the minimum diameter at ten points along the tested fiber for the calculation instead of the average diameter calculated from the density, length and weight. This minimum diameter is about 50% of the average diameter and since silks are likely to break at the narrowest point, these values may be more characteristic of the true properties of these silk fibers. Further examination of spider silk fibers (19) using scanning electron microscopy has confirmed the large variation in diameter of the fibers.

As with any polymer, especially those comprised of protein, there are numerous factors including temperature, hydration state, and rate of extension that can affect tensile strength and elasticity. Despite these caveats, it is clear that dragline silk is a unique biomaterial. Dragline silk can absorb more energy prior to breaking than nearly any commonly used material. It is nearly as strong as several of the current synthetic fibers but can outperform them in many applications where total energy absorption is required.

In 1990, the first spider silk protein from major ampullate silk was cloned in the form of a MaSp 1 cDNA from *N. clavipes* (23). The led to the appreciation that a second major ampullate silk protein existed which comprised a proline-containing peptide which was absent from the cDNA sequence coding for MaSp 1. This led to the cloning and sequencing of the cDNA for the second major ampullate silk protein, MaSp 2 (10).

The sizes of the mRNA and genes for MaSp1 and MaSp2 have been determined by analysis of Northern blots, restriction digestion patterns, and Southern blots of genomic DNA. The mRNA sizes for MaSp 1 and 2 are approximately 12.5 and 10.5 kb, respectively. The genomic DNA studies all indicate the absence of large introns in the coding regions and the lack of any detectable introns in the main portion of the gene.

SUMMARY OF THE INVENTION

Compositions and methods for producing large amounts of spider silk proteins are highly desirable give the superior quality of spider silk fibers.

Thus, in accordance with the present invention, methods for producing large quantities of novel spider silk proteins in plants, and transgenic plants comprising the same are provided.

In one embodiment, an exemplary method for expressing at least one spider silk protein in a higher plant comprises providing at least one expression vector containing a nucleic acid molecule encoding a spider silk protein, the nucleic acid sequence being operably linked to an exogenous promoter and at least one selectable marker gene which confers resistance to a selection agent. Plant cells are then contacted with the expression vector under conditions whereby the vector enters the plant cell, expresses the nucleic acid molecule, thereby producing the encoded spider silk protein. The plant cells are then incubated in the presence of a selection agent and those plant cells which survive in the presence of said agent are selected. The method optionally comprises regenerating a plant from the plant cell, a plant so isolated producing at least one spider silk protein.

Several nucleic acid sequences for producing natural and synthetic spider silk proteins are disclosed herein. Exemplary nucleic sequences for use in the methods of the invention include those set forth in SEQ ID NOS: 4, 5, 6, 7, 8, 9, 10, 11. The proteins encoded by these nucleic acids are also within the scope of the present invention and include SEQ ID NOS: 15, 16, 17, 18, 19, 20, 21, and 22. Additionally, nucleic acids encoding amino acid sequences of SEQ ID NOS: 23, 29-42, 43-43 and 49-54 and the amino acid sequences themselves are also encompassed by the present invention.

As mentioned above, the spider silk encoding nucleic acids are operably linked to a promoter element. Such promoters may be either constitutive or inducible.

The methods of the invention may be used to advantage to express spider silk proteins in plant cells such as those from *Arabidopsis*, tobacco, tubers, sunflower, canola, alfalfa, soybean maize, sorghum, wheat, cotton, small grains, and rice. Transgenic plants comprising the spider silk proteins disclosed herein are also within the scope of the invention.

DETAILED DESCRIPTION OF THE DRAWINGS

FIGS. 3A-3B show a nucleic acid sequence (GenBank Accession Number M92913; SEQ ID NO: 1) which encodes an amino acid sequence of natural MaSp2 (SEQ ID NO: 7).

FIG. 4 shows a nucleic acid sequence (SEQ ID NO: 2) which encodes amino acid sequence of a synthetic monomeric repeat of MaSp2 (SEQ ID NO: 8).

FIG. 5 shows a nucleic acid sequence (SEQ ID NO: 3) which encodes an amino acid sequence of a synthetic spider silk protein (SS1) comprising sixteen monomeric repeats of MaSp2 (SEQ ID NO: 9).

FIG. 9 shows a nucleic acid sequence (SEQ ID NO: 4) which encodes an amino acid sequence of *Argiope trifasciata* aciniform fibroin 1 (SEQ ID NO: 15).

FIG. 10 shows a nucleic acid sequence (SEQ ID NO: 5) which encodes an amino acid sequence of *Phidippus audax* fibroin 1 (SEQ ID NO: 16).

FIG. 11 shows a nucleic acid sequence (SEQ ID NO: 6) which encodes an amino acid sequence of *Zoracrates* sp. fibroin 1 (SEQ ID NO: 17).

FIGS. 12A-12E show a nucleic acid sequence (SEQ ID NO: 7) which encodes an amino acid sequence of a *Kukulcania* MaSp (SEQ ID NO: 18).

FIGS. 13A-13C show a nucleic acid sequence (SEQ ID NO: 8) which encodes an amino acid sequence of a *Kukulcania* MaSp (SEQ ID NO: 19).

FIG. 14 shows a nucleic acid sequence (SEQ ID NO: 9) which encodes an amino acid sequence of a *Kukulcania* MaSp (SEQ ID NO: 20).

FIGS. 15A-15D show a nucleic acid sequence (SEQ ID NO: 10) which encodes an amino acid sequence of an *Argiope* MiSp (SEQ ID NO: 21).

FIGS. 16A-16B show a nucleic acid sequence (SEQ ID NO: 11) which encodes an amino acid sequence of an *Argiope* MiSp (SEQ ID NO: 22).

FIG. 17 shows a consensus sequence repeat of the *A. trifasciata* aciniform fibroin 1 protein (SEQ ID NO: 23) comprised of approximately 200 amino acids.

DETAILED DESCRIPTION OF THE INVENTION

Figure 1:
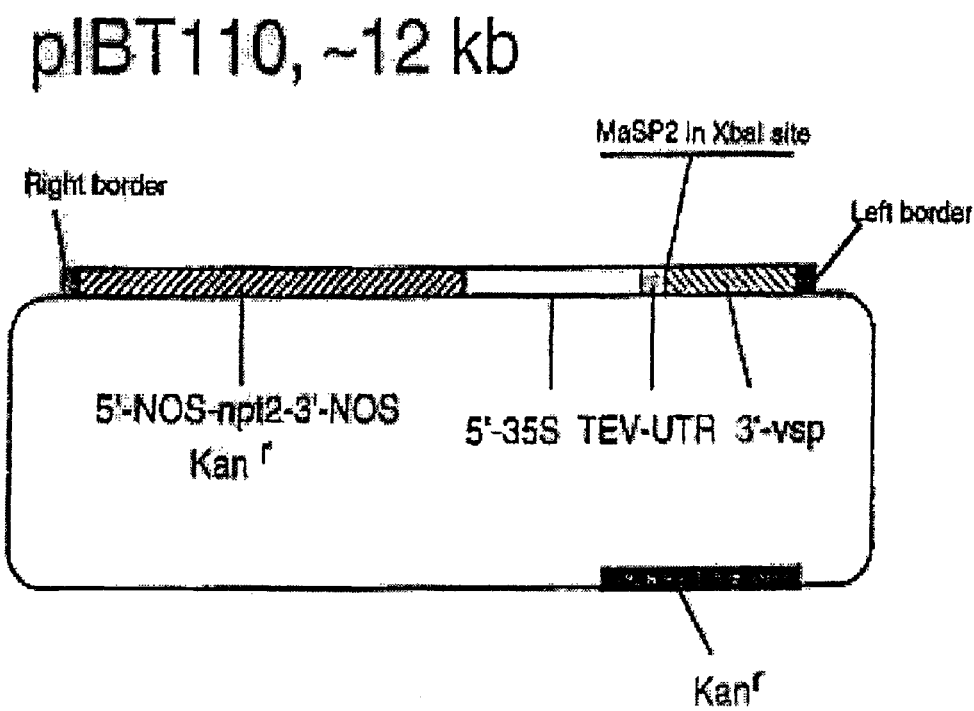
FIG. 1 shows a schematic of pBT110-SS1.

The physical characteristics of spider silk proteins confer unparalleled mechanical properties to these fibroins and, thus, render spider silk proteins ideally suited to a variety of applications. It is, therefore, desirable to generate large quantities of spider silk proteins to provide a resource for the development and execution of such applications. The expression of large quantities of spider silk proteins is, however, a technically challenging proposition. The present inventors have discovered that plants provide a model expression system for the synthesis of spider silk proteins in quantity. Accordingly, methods are provided herein for the expression of spider silk proteins in plants.

In a preferred embodiment of the invention, methods are provided for the transformation of plants with expression constructs encoding a spider silk protein.

In a particularly preferred embodiment of the invention, expression constructs are provided which comprise nucleic acid sequences encoding spider silk proteins. Such nucleic acid sequences may encode natural spider silk proteins or synthetic spider silk proteins. Nucleic acid sequences encoding synthetic spider silk proteins may be engineered to provide a spider silk protein having desirable properties optimized for a particular application.

In another aspect of the present invention, different expression constructs are provided. Such expression constructs are designed for expression of exogenous molecules in plant cells. One of skill in the art would appreciate that the choice of an expression construct may be based on a variety of different factors, including, but not limited to, the type of plant used, the mode of transformation, and the exogenous protein expressed. In yet another aspect of the invention, methods are provided for the transformation of a variety of different plants, including, but not limited to, *Arabidopsis thaliana*, alfalfa, tobacco, tubers, sunflower, canola, soybean, maize, sorghum, wheat, cotton, small grains, and rice.

In one embodiment of the present invention, methods are provided for harvesting transgenic plants expressing spider silk proteins. Also provided are methods for the isolation of spider silk proteins from cellular extracts of plant cells. Methods for the expression and isolation of spider silk proteins from plants have been previously disclosed in Scheller et al. (2001, Nature Biotechnology 19:573) and PCT Publication Number WO 01/94393 A2, the entire contents of which are incorporated herein by reference.

Additional spider silk proteins and methods for isolating the same have been previously identified, see for example U.S. Pat. Nos. 5,245,012; 5,728,810; 5,733,771; 5,756,677; 5,989,894; 5,994,099; 6,268,169 and 6,280,747, the entire disclosures of which are incorporated herein by reference.

I. Definitions

The following definitions are provided to facilitate an understanding of the present invention:

With reference to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989):

$$T_m = 81.5° C. + 16.6 \text{ Log } [Na+] + 0.41(\% G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide. Preferred oligonucleotides comprise 15-50 consecutive bases of SEQ ID NOs: 4-11.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

Amino acid residues described herein are preferred to be in the "L" isomeric form. However, residues in the "D" isomeric form may be substituted for any L-amino acid residue, provided the desired properties of the polypeptide are retained. All amino-acid residue sequences represented herein conform to the conventional left-to-right amino-terminus to carboxy-terminus orientation.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations. Pharmaceutically acceptable preparations may be used in the production of fibers and synthetic polymers, for example, that may be incorporated into a variety of medical implements, including, but not limited to, sutures, wound coverings, and implants.

A "pharmaceutically acceptable carrier" refers to a solution in which a spider silk protein or a nucleic acid sequence encoding a spider silk protein may be maintained without altering the functional properties of the spider silk molecule therein. For administration to a mammal, for example, a spider silk protein or a nucleic acid sequence encoding a spider silk protein may be suspended in any pharmaceutically acceptable carrier, for example, HEPES buffered saline at a pH of about 7.8.

Other pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

"Mature protein" or "mature polypeptide" shall mean a polypeptide possessing the sequence of the polypeptide after any processing events that normally occur to the polypeptide during the course of its genesis, such as proteolytic processing from a polyprotein precursor. In designating the sequence or boundaries of a mature protein, the first amino acid of the mature protein sequence is designated as amino acid residue 1. As used herein, any amino acid residues associated with a mature protein not naturally found associated with that protein that precedes amino acid 1 are designated amino acid −1, −2, −3 and so on. For recombinant expression systems, a methionine initiator codon is often utilized for purposes of efficient translation. This methionine residue in the resulting polypeptide, as used herein, would be positioned at −1 relative to the mature protein sequence.

A low molecular weight "peptide analog" shall mean a natural or mutant (mutated) analog of a protein, comprising a linear or discontinuous series of fragments of that protein and which may have one or more amino acids replaced with other amino acids and which has altered, enhanced or diminished biological activity when compared with the parent or nonmutated protein.

The term "biological activity" is a function or set of functions performed by a molecule in a biological context (i.e., in an organism or an in vitro surrogate or facsimile model). For spider silk proteins, biological activity is characterized by physical properties (e.g., tensile strength and elasticity) as described herein.

The term "substantially pure" refers to a preparation comprising at least 50-60% by weight the compound of interest (e.g., nucleic acid, oligonucleotide, polypeptide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, mass spectrometry and the like).

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "vector" is a replicon, such as a plasmid, cosmid, bacmid, phage or virus, to which another genetic sequence or element (either DNA or RNA) may be attached so as to bring about the replication of the attached sequence or element. An "expression vector" is a specialized vector that contains a gene with the necessary regulatory regions needed for expression in a host cell. Such vectors may be obtained from various commercial sources, including Clontech Laboratories, Inc. (Palo Alto, Calif.), Stratagene (La Jolla, Calif.), Invitrogen (Carlsbad, Calif.), New England Biolabs (Beverly, Mass.) and Promega (Madison, Wis.). Exemplary vectors which may be used in the present invention include, but are not limited to, pIBT110, pBI121, and pGreen.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

An exogenous coding region is typically flanked by operably linked regulatory regions that regulate expression of the exogenous coding region in a transformed plant cell. A typical regulatory region operably linked to the exogenous coding region includes a promoter, i.e., a nucleic acid fragment that can cause transcription of the exogenous coding region, positioned 5' to the exogenous coding region. The invention is not limited by the use of any particular promoter and a wide variety are known in the art. Plant-specific promoters are preferred. These include, but are not limited to, constitutive promoters, inducible promoters, and tissue-specific promoters.

A promoter may be, but need not be, heterologous with respect to the host. Promoters may be obtained from Ti- or Ri-plasmids, from plant cells, plant viruses or other hosts wherein the promoters are functional in plants. Such promoters include, for example, the octopine synthetase promoter, the nopaline synthase promoter, and the manopine synthetase promoter, promoters of bacterial origin which are functional in plants. Viral promoters include the cauliflower mosaic virus full length (CaMV35S) and region VI promoters, etc. Endogenous plant promoters include the ribulose-1,6-biphosphate (RUBP) carboxylase small subunit (ssu) promoter, the beta-conglycinin promoter, the phaseolin promoter, the ADH promoter, GPAL2 promoter, GPAL3 promoter, heat-shock promoters, and tissue specific promoters, e.g., promoters associated with fruit ripening. In one embodiment of the present invention, the promoter is a constitutive CaMV35S promoter.

As described above, expression vectors may comprise an inducible promoter operably linked to a spider silk encoding nucleic acid sequence. "Inducible" promoters may direct expression of a polynucleotide to which they are operably linked in a tissue or developmental stage specific manner or may respond to environmental conditions. In one aspect of the invention, expression vectors comprising a tightly-regulated inducible promoter operably linked to a nucleic acid encoding a spider silk protein may be used. Such expression vectors may further comprise a selectable marker gene (e.g. a gene encoding a protein which confers antibiotic resistance) operably linked to either a constitutive promoter or a tightly-regulated inducible promoter. Depending on the application, it may be beneficial to express the spider silk encoding nucleic acid sequence from a pathogen-inducible promoter. Such promoters include those derived from pathogenesis-related proteins (PR proteins), which are induced following infection by a pathogen, e.g. PR proteins, SAR proteins, beta-1,3 glucanase, chitinase, etc. See, for example, Redolfi et al., *Neth J Plant Pathol* 89: 245 (1983); Uknes et al., *Plant Cell* 4: 645 (1992); Van Loon, *Plant Mol Virol* 4: 111 (1985).

In an aspect of the present invention, it may be advantageous to utilize promoters which are expressed locally at or near the site of pathogen infection. See, for example, Marineau et al., *Plant Mol Biol* 9: 335 (1987); Matton et al., *Mol Plant-Microbe Interact* 2: 325 (1989); Somsisch et al., *Mol and Gen Genetics* 2: 93 (1988). Yang, *Proc Natl Acad Sci* 93: 14972 (1996). See also, Chen et al., *Plant J* 10: 955 (1996); Zhang and Sing, *Proc Natl Acad Sci USA* 91: 2507 (1994); Warner et al., *Plant J* 3: 191 (1993); Siebertz et al., *Plant Cell* 1: 961 (1989); and the references cited therein. The inducible promoter of the maize PRms gene, whose expression is induced by the pathogen *Fusarium moniliforme*, may be of particular utility for a number of applications (see, for example, Cordero et al., *Physiol and Mol Plant Path* 41: 189 (1992).

Additionally, because pathogens enter plants through wounds, which may result from insect damage, a wound-inducible promoter may be used in the expression vectors of the invention. Such wound inducible promoters include, but are not limited to, potato proteinase inhibitor (pin II) gene (Ryan, *Annu Rev Phytopath* 28: 425; Duan et al., *Nature Biotech* 14: 494; wun1 and wun2, U.S. Pat. No. 5,428,148; win1 and win2 (Stanford et al., *Mol Gen Genet* 215: 200; systemin (McGurl et al., *Science* 225: 1570; WIPI (Rohmeier et al., *Plant Mol Biol* 22: 783; Eckelkamp et al., *FEBS Let* 323: 73; MPI gene (Corderok et al., 6(2) *Plant J* 141 and references contained therein.

The transcriptional activity of inducible promoters may also be regulated by various environmental conditions, including, but not limited to, temperature, anaerobic stress, and light. Examples of inducible promoters include the Adh1 promoter which is induced by hypoxia or cold stress, the Hsp70 promoter which is induced by heat stress, and the PPDK promoter which is induced by light. Examples of developmentally regulated promoters include promoters which initiate transcription only, or preferentially, in certain tissues, such as leaves, roots, fruit, seeds, or flowers. An exemplary promoter is the anther specific promoter 5126 (U.S. Pat. Nos. 5,689,049 and 5,689,051).

Construction of vectors comprising promoters in frame with nucleic acids is known in the art, and may be accomplished according to i.e. Sambrook et al., *Molecular Cloning. A Laboratory Manual* (Cold Spring Harbor Laboratory Press, 1989) and Ausubel et al., *Current Protocols in Molecular Biology* (Greene Publishing Associates, Inc., 1993).

Another typical regulatory region operably linked to an exogenous coding region includes a terminator (i.e., a nucleic acid fragment that can cause the termination of transcription of an exogenous coding region) positioned 3' to the exogenous coding region. The invention is not limited by the use of any particular terminator, and a wide variety are known in the art. Plant-specific terminators are preferred. These include, but are not limited to, a nopaline synthase terminator derived from the *Agrobacterium tumefaciens* Ti plasmid (Nos-ter).

Expression vectors which comprise nucleic acid sequences encoding spider silk proteins are within the scope of the present invention. Also included in the present invention are recombinant plant cells, recombinant seeds, recombinant plant embryos, and recombinant plants comprising the expression vectors encoding spider silk proteins described herein.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

A "clone" or "clonal cell population" is a population of cells derived from a single cell or common ancestor by mitosis.

A "cell line" is a clone of a primary cell or cell population that is capable of stable growth in vitro for many generations.

An "immune response" signifies any reaction produced in response to an antigen, such as a viral antigen, in a host having a functioning immune system. Immune responses may be either humoral in nature, that is, involve production of immunoglobulins or antibodies, or cellular in nature, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems. Such immune responses may be important in protecting the host from disease and may be used prophylactically and therapeutically.

An "immune response" in plants refers to the ability of a plant to respond to infection by microbial pathogens, for example, through the activation of a variety of defense responses. At the sites of infection, a hypersensitive response (HR) is often initiated. The hallmark of this response is the formation of necrotic lesions, a process that is likely due to programmed host cell death. In addition, associated with the HR is the restriction of pathogen growth and spread. Frequently, defense responses are also activated in tissue distal to the sites of infection according to a phenomenon known as systemic acquired resistance (SAR). Development of SAR results in an enhanced and long-lasting resistance to secondary challenge by the same or even unrelated pathogens. Associated with both HR and SAR is the expression of pathogenesis-related (PR) genes, several of whose products have been shown to have antimicrobial activity (for review, see U.S. Pat. Nos. 6,136,552; 5,989,846; 5,977,442; and 5,939,601).

In accordance with the present invention, expression of spider silk proteins in plants cells does not induce an appreciable cellular immune response as evidenced by the normal phenotype exhibited by such transgenic plants. Moreover, spider silk proteins are not known to elicit an immune response when introduced as a component of a transplant into an animal. The apparent absence of immunogenicity for spider silk proteins is a feature which may be used to advantage in applications in which the plant-derived spider silk proteins of the present invention are used as components in medical devices, implants, and the like.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

With respect to antibodies, the term "immunologically specific" refers to antibodies that bind to one or more epitopes of a protein or compound of interest, but which do not substantially recognize and bind other molecules in a sample containing a mixed population of antigenic biological molecules.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

A "derivative" of a spider silk protein or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the essential activity of original the spider silk protein.

As mentioned above, a spider silk polypeptide or protein of utility in the methods of the invention may be any analogue, fragment, derivative or mutant which is derived from a spider silk protein and which retains at least one property or other characteristic of a spider silk protein. Different "variants" of spider silk proteins exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to a spider silk protein, (c) variants in which one or more amino acids include a substituent group, and (d) variants in which a spider silk protein or fragment thereof is fused with another peptide or polypeptide such as a fusion partner, a protein tag or other chemical moiety, that may confer useful properties to a spider silk protein, such as, for example, an epitope for an antibody, a polyhistidine sequence, a biotin moiety and the like. Other spider silk proteins of the invention include variants in which amino acid residues from one species are substituted for the corresponding residue in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art.

The term "functional" as used herein implies that the nucleic or amino acid sequence is functional for the recited assay or purpose.

A "unit repeat" constitutes a repetitive short sequence. Thus, the primary structure of the spider silk proteins is considered to consist mostly of a series of small variations of a unit repeat. The unit repeats in the naturally occurring proteins are often distinct from each other. That is, there is little or no exact duplication of the unit repeats along the length of the protein. Synthetic spider silks, however, may be made wherein the primary structure of the protein comprises a number of exact repetitions of a single unit repeat. SEQ ID NO: 3 (FIG. 5), for example, encodes a synthetic spider silk protein comprising 16 repeats of the MaSp2 monomeric unit SEQ ID NO: 2 (FIG. 4). Additional synthetic spider silks may be synthesized which comprise a number of repetitions of one unit repeat together with a number of repetitions of a second unit repeat. See Example IV. Such a structure would be similar to a typical block copolymer. Unit repeats of several different sequences may also be combined to provide a synthetic spider silk protein having properties suited to a particular application.

The term "direct repeat" as used herein is a repeat in tandem (head-to-tail arrangement) with a similar repeat.

The term "native or natural spider silk protein" refers to those proteins that are present in the silks produced by spiders. These proteins may be derived from the silk itself by dissolution or from the specific silk gland in the abdomen of the spider before the silk is spun. The term may also be applied to a spider silk protein produced using a variety of expression systems, which comprises substantially the same amino acid sequence as that produced by a spider The term "synthetic spider silk protein" refers to a spider silk protein which has been produced by an expression system and whose sequence may be based on a natural spider silk protein sequence or an artificially produced nucleic acid sequence which encodes key amino acid motifs of spider silk proteins.

II. Preparation of Spider Silk-Encoding Nucleic Acid Molecules, Spider Silk Proteins, and Antibodies Thereto

A. Nucleic Acid Molecules

Nucleic acid molecules encoding the polypeptides of the invention may be prepared by two general methods: (1) synthesis from appropriate nucleotide triphosphates, or (2) isolation from biological sources. Both methods utilize protocols well known in the art. The availability of nucleotide sequence information, such as the DNA sequences encoding a natural or synthetic spider silk protein, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be used directly or purified according to methods known in the art, such as high performance liquid chromatography (HPLC).

In accordance with the present invention, nucleic acids having the appropriate level of sequence homology with sequences encoding a spider silk protein may be identified by using hybridization and washing conditions of appropriate stringency. Such methods are useful for a variety of purposes, including the screening of libraries comprising mutated spider silk-encoding nucleic acid sequences for desired properties. For example, hybridizations may be performed, according to the method of Sambrook et al., *Molecular Cloning*, Cold Spring Harbor Laboratory (1989), using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

The nucleic acid molecules described herein include cDNA, genomic DNA, RNA, and fragments thereof which may be single- or double-stranded. Thus, oligonucleotides are provided having sequences capable of hybridizing with at least one sequence of a nucleic acid sequence, such as selected segments of sequences encoding a spider silk protein. Also contemplated in the scope of the present invention are methods of use for oligonucleotide probes which specifically hybridize with DNA from sequences encoding a spider silk protein under high stringency conditions. Primers capable of specifically amplifying sequences encoding a spider silk protein are also provided. As mentioned previously, such oligonucleotides are useful as primers for detecting, isolating and amplifying sequences encoding a spider silk protein.

The invention also encompasses the use of nucleic acid molecules encoding synthetic spider silk proteins. Such synthetic spider silk proteins may be engineered to possess particular physical and mechanical properties that render them appropriate for different applications. A synthetic spider silk protein may be constructed by assembling spider silk protein unit repeats into a contiguous polypeptide chain as set forth in Example IV and Table II. Also provided herein is guidance regarding the types and numbers of unit repeats which may be combined and the order in which they may be assembled. Exemplary synthetic spider silk proteins comprising MaSp2, Flag, and MaSp1 analogs are also provided. See Example IV. For some applications, it may be desirable to operably link a synthetic spider silk protein to a tag moiety as described herein.

B. Proteins

The availability of nucleic acid molecules encoding spider silk proteins enables production of large quantities of spider silk protein in a suitable prokaryotic or eukaryotic system. For example, part or all of at least one DNA molecule encoding a natural or synthetic spider silk protein, such as the nucleic acid sequence of SEQ ID NO: 1, may be inserted into a plasmid vector adapted for expression in a bacterial cell, such as *E. coli*. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences. Such methods may be used to evaluate constructs for expression of spider silk proteins in, for example, a bacterial system which affords a rapid and reliable screening technique.

The spider silk proteins produced by gene expression in a recombinant prokaryotic or eukaryotic system may be purified according to methods known in the art. In a preferred embodiment, a commercially available expression/secretion system may be used, whereby the recombinant protein is expressed and thereafter secreted from the host cell, to be easily purified from the surrounding medium. If expression/secretion vectors are not used, an alternative approach involves purifying the recombinant protein from cell lysates (remains of cells following disruption of cellular integrity) derived from prokaryotic or eukaryotic cells in which a protein was expressed. Methods for generation of such cell lysates are known to those of skill in the art. Recombinant protein may be purified by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

Alternatively, standard purification strategies designed to differentially isolate silk protein from plant homogenates may be used to advantage. Purification of a plant-expressed spider silk protein may be facilitated by its extreme stability under conditions that denature typical proteins, such as, for example, high heat and low pH. Accordingly, general protein purification strategies may be adapted to optimize silk purification from plants. Above-ground portions of transgenic plants may be harvested and allowed to air dry as per normal production practices. The "hay" may be homogenized in an appropriate buffer followed by various treatments designed to differentially eliminate contaminants. Silk protein recovery may be optimized following treatments in which plant extracts are subject to any one or a combination of the following: 1) boiling in the presence or absence of detergent; 2) differential centrifugation; 3) progressively decreasing the pH; and 4) precipitation with varying concentrations of urea or ammonium sulfate. One of ordinary skill in the art may vary the above treatments to optimize the yield and efficiency of purification of spider silk proteins from plants.

The level of silk protein may be determined by immunoblotting and the purity and concentration assessed definitively by amino acid analysis. Purified silk protein may be analyzed for mechanical properties as previously described (18) to ensure that the recombinant protein possesses the desired properties.

The spider silk proteins of the invention, prepared by the aforementioned methods, may be analyzed according to standard procedures. For example, such proteins may be subjected to amino acid sequence analysis, according to known methods.

A protein produced according to the present invention may be chemically modified after synthesis of the polypeptide. The presence of several carboxylic acid side chains (Asp or Glu) in the spacer regions facilitates the attachment of a variety of different chemical groups to silk proteins including amino acids having such side chains. The simplest and easiest procedure is to use a water-soluble carbodiimide to attach the modifying group via a primary amine. If the group to be attached has no primary amine, a variety of linking agents can be attached via their own primary amines and the modifying group attached via an available chemistry. Jennes, L. and Stumpf, W. E. Neuroendocrine Peptide Methodology, Chapter 42. P. Michael Conn, editor. Academic Press, 1989.

Desirable chemical modifications include, but are not limited to, derivatization with peptides that bind to cells, e.g. fibroblasts, derivatization with antibiotics and derivatization with cross-linking agents so that cross-linked fibers can be made. The selection of derivatizing agents for a particular purpose is within the skill of the ordinary practitioner of the art.

Exemplary Methods for Generation of Spider Silk Proteins

In view of the unique properties of spider silk proteins, special considerations should be applied to the generation of synthetic spider silk proteins. The repetitive nature of amino acid sequences encoding these proteins may render synthesis of a full length spider silk protein, or fragments thereof, technically challenging. To facilitate production of full length silk protein molecules, the following protocol is provided.

The polypeptides of the present invention can be made by direct synthesis or by expression from cloned DNA. Means for expressing cloned DNA are set forth above and are generally known in the art. The following considerations are recommended for the design of expression vectors used to express DNA encoding spider silk proteins.

First, since spider silk proteins are highly repetitive in structure, cloned DNA should be propagated and expressed in host cell strains that can maintain repetitive sequences in extrachromosomal elements (e.g. SURE™ cells, Stratagene). The prevalence of specific amino acids (e.g., alanine, glycine, proline, and glutamine) also suggests that it might be advantageous to use a host cell that over-expresses tRNA for these amino acids or in which these specific tRNAs are known to be in high abundance.

The proteins of the present intention can otherwise be expressed using vectors providing for high level transcription of a spider silk protein or, fusion proteins thereof. Fusion protein tags (e.g., His tags) facilitate affinity purification of epitope-tagged proteins. The hosts may be either bacterial or eukaryotic cells. Eukaryotic cells such as yeast, especially *Saccharomyces cerevisisae*, or insect cells might be particularly useful eukaryotic hosts. In a particularly preferred embodiment of the invention, host cells in which spider silk proteins are expressed are plant cells. Such plant cells may be maintained in vitro or in vivo in a plant transformed with an expression construct encoding a spider silk protein. Expression of an engineered minor ampullate silk protein is described in U.S. Pat. No. 5,756,677, herein incorporated by reference. Such an approach may be used to express proteins of the present invention.

Exemplary Methods for Plant Transformation

Growth Conditions of the Plant Material Pre-Infiltration

Plants which may be transformed using the methods of the present invention include, but are not limited to *Arabidopsis thaliana*, alfalfa, tobacco, tubers, sunflower, canola, soybean, maize, sorghum, wheat, cotton, small grains, and rice. Sow ~50 individual seeds onto the surface of moderately wet compost. Incubate at 4° C. for 64 hours for stratification (optional). Incubate in a greenhouse (sixteen-hour day photoperiod, 15° C. night and 20 to 25° C. day temperature with additional artificial light (105 µE m$^2$/s) and sub-irrigate until germination. Water moderately for 4 to 6 weeks. Plants should be as vigorous as possible. Optimal development may be achieved by growth during the rosette stage under conditions corresponding to relatively short days (13 h). To avoid etiolation, sufficient lighting may be provided. The optimal stage for infiltration tends to be coincident with the formation of the first siliques and the appearance of secondary floral stems.

*Agrobacterium* Culture and Preparation

Precultures may be prepared by inoculating 10 ml of Luria Broth (LB) medium containing the appropriate antibiotics with 100 µl of a fresh culture or a glycerol stock, or with a colony taken from a dish. Cultures may be maintained for approximately 1 month at 4° C. and used as an inoculum for a larger culture. Precultures may be grown at 28° C. with good aeration overnight. Two liter flasks containing 1 liter of LB medium and the appropriate antibiotics may be inoculated with 10 ml of preculture and grown at 28° C. with good aeration until an OD($600_{nm}$) of at least 0.8 is obtained. The MP5-1 strain of *Agrobacteria*, for example, requires 15 hours to reach the desired optical density (OD), but it may take longer for other strains. Bacteria may be pelleted by centrifugation at 8000 g for 8 minutes and gently resuspended in 1 liter of the initial volume of infiltration medium for vacuum infiltration and in one volume of 5% sucrose—200 µl 1 Silwet L-77 for floral dipping.

The LBA 4404 strain, which was used herein, may be prepared following a protocol essentially the same as that described above for the MP5-1 strain.

Vacuum Infiltration

Four to six week-old plants are gently removed from the soil with the roots intact. Alternatively plants may remain in the tray and infiltration may be performed on the leaves and stems only (see below). The roots may be rinsed briefly in water to eliminate any adhering soil particles. Immerse 25 to 50 plants in 300 ml of fresh bacterial suspension. The plants (in trays) may be placed in a vacuum chamber and vacuum pressure applied (~$10^4$ Pa (0.1 atm) for 20 minutes, after which the vacuum may be released slowly. Replant the infiltrated plants ($T_0$) in the trays filled with compost (watered and treated). Cover with a perforated plastic wrap or a seed tray incubator and water from below. Remove the cover 3-4 days later. Water the plants moderately until maturity (4-6 weeks) and dry the plant progressively to allow the leaves to dry while the floral stems hold up and continue to flower. Harvest the seeds from 50 plants in bulk. Let the siliques dry at 27° C. for 2 days, then thresh and clean the seeds.

Floral Dipping

The bacterial suspension may be placed in an appropriate recipient which is chosen based on the length of the floral stems. The whole plant or just the floral stems may be dipped in the suspension for 2 minutes, after which the plants may be grown in a greenhouse or growth chamber for two days under the cover of a seed tray incubator. Plants may be cultivated following standard protocols.

Screening of Transformants

In the greenhouse. Seed transformed with pIBT110, for example, may be plated on agarose plates (50 µg/ml kanamycin) to select for positive transformant seedlings. Such seedlings may be transferred to soil after approximately 1-2 weeks.

For applications in which vectors that confer herbicide resistance have been used, each bulk of seeds may be sowed in an appropriately sized tray (e.g., 55×36) containing Perlite and a top layer of fine sand, which has been previously wet with water containing a herbicide. The herbicide used will vary according to the selection marker used. In preferred embodiments, the herbicide used may be phosphinothricin (at a final concentration of ~7.5 mg/l) or glyphosate (Roundup, at a final concentration of ~18 mg/l). Perlite may be used to reduce the weight of the trays. Sand particles of a sufficiently small size may be used to inhibit sowing of seeds on the surface. Transformed plants may be supplemented with a nutrient solution at the 2-leaf stage. Germination may be synchronized by incubation at 4° C. for 64 hours, after which the trays may be transferred to a greenhouse and sub-irrigated permanently with water containing an appropriate herbicide, as described above for 4 weeks. Transformants ($T_1$) having normal green cotyledons and first leaves formed may be observed after two weeks. The growth of untransformed plantlets is inhibited following germination and generally is indicated by the absence of cotyledon expansion, the rudiments of which rapidly turn yellow.

When resistant plantlets have reached the 4-5 leaf-stage, they may be transferred into individual pots (~5.5 cm diameter) containing compost (watered and treated) and covered to facilitate rooting. Plantlets may be watered moderately, alternating tap water and a nutrient solution until the flowering stage. The frequency of watering may be progressively reduced as described above, while the $T_1$ plants finish producing flowers. Plants may be staked and individualized with perforated transparencies rolled up around the pot. When siliques have dried, the $T_2$ seeds from each $T_1$ plant may be harvested and cleaned. The in vitro segregation of the T-DNA selectable markers and Southern blotting analysis may be performed to estimate the number of loci and the number of copies of T-DNA. Generally, more than 50% of transformants with a T-DNA insertion occur at a single Mendelian locus and 70% of the T-DNA insertions occur in tandem.

In Vitro Culture

The seeds may be divided into 1.5 ml microtubes, at approximately 100 µl of seeds per tube. One ml of sterilization solution may be added to the tubes prior to closure of the tubes and mixing of the contents. The tubes may be incubated on their sides in a laminar flow cabinet for 8 minutes to disperse the seeds into the solution to facilitate sterilization. The solution may be removed with a pipette and rinsed twice with 1 ml of pure 95% ethanol. The ethanol may be removed as effectively as possible and the seeds dried in the flow cabinet overnight. No more than 500 seeds may be sowed under sterile conditions on a 10 cm Petri dish containing the selective medium, which may be closed and sealed appropriately. The dishes may be incubated at 4° C. for 64 hours, after which they are transferred to a growth chamber (16 hour day length; 20° C.). Transformants (green rooted plants) may be scored 10 days later for kanamycin selection, for example. Resistant plantlets may be planted individually in pots when sufficiently developed (4-5 leaf-stage), transferred to a growth chamber, and covered to facilitate rooting. The process may be continued as described above.

Control of *Arabidopsis* Pests

Several insect and fungal pests are known to adversely affect *Arabidopsis* plants. Below are some of the pests that may affect *Arabidopsis*, and a description of the pesticides used to combat them.

Thrips may infect flowers and reduce fertility, and can transmit virus. Spraying abamecin (9 mg/l) or formetanate (500 mg/l) (homogeneously wet the plants) may be used to control them.

Aphids may accumulate on the stems and leaves. These may be controlled with regular nicotine (150 mg/m$^2$) fumigation in the greenhouse.

Sciarid flies may lay eggs in the soil and their larvae eat the vegetative leaves. A sciarid infestation is indicated by the presence of large numbers of small black flies around the plants. Abamecin (9 mg/l) or cyromazine (300 mg/l) may be sprayed on the trays after sowing or on the plants after floral induction to control such infestations.

Gray rot is a fungal infection that may affect the plants when high levels of humidity are maintained. This may be controlled by spraying with vinchlozoline (750 mg/l).

The following materials are provided to facilitate the practice of the present invention: 22×16 cm aluminum trays (Bourgeat, 38490 Les Abrets, France), net pots diameter=5.5 cm (TEKU, D2842 Lohne/Oldb, Germany), 45×33×3.5 cm incubator for seed trays (BHR, 71370 St Germain du Plain, France), 28×38 cm carrying tray (KIB NL5140 AD Waalwijk, Netherlands), 40-well multipot trays (KIB, Netherlands), perforated plastic wrap (1000 holes/m2) subirrigation potting mix (WOGEGAL, 27700 St Pierre-des-Corps, France), 0.5 mm sieved sand, perlite, Hypnol (nicotine) plant louse treatment (CP Jardin 59570 Bavay, France) Vertimec (abamecin) sciarid flies and thrips treatment (Merck-Sharp), Dicarzol 200 (formetanate) thrips treatment (Hoechst), Trigard 75 WP (cyromazine) sciarid flies treatment (Merck-Sharp), Ronilan (vinchlozoline) gray rot treatment (BASF), Dedevap (dichlorvos) empty greenhouse disinfection (Bayer), FINAL™ (phosphinothricin) transformed plant selection (Hoechst), Roundup (glyphosate) transformed plant selection (Monsanto).

| Media *Agrobacterium* culture medium | |
|---|---|
| LB (Luria-Bertani) medium | (g/l) |
| Bacto-tryptone | 10 |
| Bacto-Yeast extract | 5 |
| NaCl | 10 |
| pH = 7 | | pH adjusted with 1M NaOH. The medium is sterilized by autoclaving at 115° C. for 20 min.

| Infiltration medium | |
|---|---|
| | (mg/l) |
| Macroelements | |
| $NH_4NO_3$ | 1650 |
| $KNO_3$ | 1900 |
| $CaCl_2, 2H_2O$ | 440 |
| $MgSO_4, 7H_2O$ | 370 |
| $KH_2PO_4$ | 170 |
| Microelements | |
| $H_3BO_3$ | 6.3 |
| $MnSO_4, 4H_2O$ | 22.3 |
| $ZnSO_4, 7H_2O$ | 8.6 |
| KI | 0.83 |
| $Na_2MoO_4, 2H_2O$ | 0.25 |
| $CuSO_4, 5H_2O$ | 0.025 |
| $CoCl_2, 6H_2O$ | 0.025 |
| BA | 0.010 |
| Sucrose | 50000 |
| pH | 5.8 |

The microelements and 6-benzylaminopurine (BA) may be made as concentrated stock solutions (at 1000× and 1 mg/l respectively) and stored at 4° C. The pH is adjusted with KOH and the medium is sterilized by autoclaving at 115° C.

Floral Dipping Medium

Combine $H_2O$+Sucrose 5%+200 μl/l Silwet L-77 (OSI Specialties S.A. 7 rue du Pré-Bouvier CH-1217 MEYRIN SWITZERLAND).

Sterilization Solution

Dissolve 1 tablet of Bayrochlore (contains sodium dichlorocyanate and releases 1.5 g of active chlorine; Bayrol GMBH, D-800 München 70) in 40 ml of distilled water and add some drops of 1% Tween. Use 5 ml in 45 ml Ethanol 95%.

| In vitro culture medium | |
|---|---|
| | (mg/l) |
| Macroelements | |
| $KNO_3$ | 506 |
| $KH_2PO_4$ | 340 |
| $MgSO_4(7H_2O)$ | 493 |
| $Ca(NO_3)2(4H_2O)$ | 472 |
| Microelements | |
| $H_3BO_3$ | 4.3 |
| $MnCl_2(4H_2O)$ | 2.8 |
| $CuSO_4(5H_2O)$ | 0.13 |
| $Na_2MoO_4(2H_2O)$ | 0.05 |
| NaCl | 0.58 |
| $ZnSO_4(7H_2O)$ | 0.29 |
| $CoCl_2(6H_2O)$ | 0.0025 |
| Morel and Wetmore vitamins | |
| Myo-inositol | 100 |
| Calcium panthothenate | 1 |
| Niacine | 1 |
| Pyridoxine | 1 |
| Thiamine Hcl | 1 |
| Biotin | 0.01 |
| MES | 700 |
| Sucrose | 10000 |
| Agar BIOMAR | 7000 |
| pH = 5.8 | |

5 ml/l of a filter sterilized ammoniacal iron citrate stock solution (1%) and for kanamycin selection 1 ml/l of a filter sterilized kanamycin stock solution (100 mg/ml) may be added after autoclaving at 115° C.

Macroelements, microelements, vitamins and MES are made up as concentrated stock solutions and stored at room temperature or at 4° C. for the microelements and the vitamins. The stock solutions are made as followed: 200×$KNO_3$ (1M), 400×$KH_2PO_4$ (1M), 500×$MgSO_4$ ($7H_2O$) (1M), 500× $Ca(NO_3)2(4H_2O)$ (1M), 1000× microelements, 500× Vitamins, 100×MES (14%). Agar is added in each bottle before autoclaving. The pH is adjusted with KOH. The medium is sterilized by autoclaving at 115° C.

Plant Materials

*Arabidopsis thaliana* (L.) Heyn., ecotype Wassilevskija (WS) may be used. [Ecotype Columbia (Co10), for example]. Nossen (No0) and Landsberg erecta may also is be used with good efficiency.

*Agrobacterium* Strains and Vectors

The *Agrobacterium* strain MP5-1 may be used in the methods of the present invention. This strain carries the binary vector pGKB5 (Bouchez et al., 1993), which was constructed for T-DNA insertional mutagenesis. This plasmid is very stable in *Agrobacterium* under non-selective conditions and confers resistance to kanamycin. It was introduced into the helper strain C58Cl (pMP90) (Bouchez et al., 1993), which contains a disarmed C58 Ti plasmid, to produce strain MP5-1. The T-DNA contains a promoterless GUS reporter gene fused to the right border, and kanamycin and Basta resistance genes as plant selection markers.

Other binary vectors and helper strains may also be used, including, but not limited to the strains LBA 4404, ABI, ASE, GV3101; vectors pBin19, pOCA18, pCGN, and pDE1001. Commonly used binary vectors confer resistance to kanamycin and selection of transformants is performed in vitro under sterile conditions.

References which may be of utility in practicing the methods of the present invention include the following: Bechtold et al. (1993) C R Acad Sci Paris, Life Sciences 316:1194-1199; Bent et al. (1994) Science 265:1856-1860; Bouchez et al. (1993) C R Acad Sci Paris, Life Sciences 316:1188-1193; Chang et al. (1990) The Plant Journal 5:551-558; Clough and Bent. (1998) The Plant Journal 16:735-743; Damm et al. (1989) Mol. Gen. Genet. 213:15-20; Feldmann and Marks. (1987) Mol Gen Genet 208:1-9; Hooykaas and Schilperoort. (1992) Plant Mol Biol. 35:205-218; Koncz and Schell. (1986) Mol Gen Genet 204:383-396; Tinland. (1996) Trends in Plant Science. 1:178-184; Valvekens et al. (1988) Proc. Natl. Acad. Sci. USA. 85:5536-5540; Zupan and Zambryski (1997) Critical Reviews in Plant Sciences. 16:279-295, the entire contents of which are incorporated herein by reference.

Chloroplast Transformation for High Level Expression of Transgenes

A gene of interest (e.g., the SS1 gene) may be inserted into a chloroplast expression vector such as those described by DeGray et al. (Plant Physiology 127: 852-862) and Lutz et al. (Plant Physiology 125, 1585-11590). Transplastomic tobacco plants transformed by a chloroplast expression vector comprising the SS1 gene may be generated according to DeGray et al. and Lutz et al. Additional methodology pertaining to chloroplast transformation of plants has been described in U.S. Pat. Nos. 5,451,513; 5,545,818; and 6,376,744, the entire contents of which are incorporated herein by reference. Target gene integration, copy number, and transcription levels may be determined by Southern and Northern analyses. Western blotting may be used to quantify levels of protein expression.

Harvesting and Purification of Spider Silk Proteins from Plants

A useful spider silk protein or fragment thereof may be (1) insoluble inside a cell in which it is expressed and (2) capable of being formed into an insoluble fiber under normal conditions by which fibers are made. Preferably, the protein is insoluble under conditions (1) and (2). Specifically, the protein or fragment may be insoluble in a solvent such as water, alcohol (methanol, ethanol, etc.), acetone and/or organic acids, etc. The spider silk protein or fragment thereof should be capable of being formed into a fiber having high tensile strength, e.g., a tensile strength of 0.5x to 2x wherein x is the tensile strength of a fiber formed from a corresponding natural silk or whole protein. A spider silk protein or fragment thereof should also be capable of being formed into a fiber possessing high elasticity, e.g., at least 15%, more preferably about 25%.

Variants of a spider silk protein may be formed into a fiber having a tensile strength and/or elasticity which is greater than that of the natural spider silk or natural protein. The elasticity may be increased up to 100%. Variants may also possess properties of protein fragments.

A fragment or variant may have substantially the same characteristics as a natural spider silk. The natural protein may be particularly insoluble when in fiber form and resistant to degradation by most enzymes.

Recombinant spider silk proteins may be recovered from cultures by lysing cells to release spider silk proteins expressed therein. Initially, cell debris can be separated by centrifugation. Clarified cell lysate comprised of debris and supernatant may be repeatedly extracted with solvents in which spider silk proteins are insoluble, but cellular debris is soluble. A differential solubilization process such as described above may be used to facilitate isolation of a purified spider silk protein precipitate. These procedures may be repeated and combined with other procedures including filtration, dialysis and/or chromatography to obtain a pure product.

Fibrillar aggregates may form from solutions by spontaneous self-assembly of spider silk proteins when the protein concentration exceeds a critical value. The aggregates may be gathered and mechanically spun into macroscopic fibers according to the method of O'Brien et al. [I. O'Brien et al., "Design, Synthesis and Fabrication of Novel Self-Assembling Fibrillar Proteins", in Silk Polymers: Materials Science and Biotechnology, pp. 104-117, Kaplan, Adams, Farmer and Viney, eds., c. 1994 by American Chemical Society, Washington, D.C.; Lazaris et al., 2002, Science 295:472-476].

Exemplary Methods for Preparation of Fibers from Spider Silk Proteins

As noted above, the spider silk proteins may be viewed as derivatized polyamides. Accordingly, methods for producing fiber from soluble spider silk proteins are similar to those used to produce typical polyamide fibers, e.g. nylons, and the like.

O'Brien et al. supra describe fiber production from adenovirus fiber proteins. Following general methods for fiber production, spider silk proteins may be solubilized in a strongly polar solvent. The protein concentration of such a protein solution should typically be greater than 5% and is preferably between 8 and 20%.

Fibers may preferably be spun from solutions having properties characteristic of a liquid crystal phase. The fiber concentration at which phase transition can occur is dependent on the polypeptide composition of a protein or combination of proteins present in the solution. Phase transition, however, may be detected by monitoring the clarity and birefringence of the solution. Onset of a liquid crystal phase may be detected when the solution acquires a translucent appearance and registers birefringence when viewed through crossed polarizing filters.

The solvent used to dissolve a spider silk protein may be polar, and is preferably highly polar. Such solvents are exemplified by di- and tri-haloacetic acids, haloalcohols (e.g. hexafluoroisopropanol). In some instances, co-solvents such as acetone are useful. Solutions of chaotropic agents, such as lithium thiocyanate, guanidine thiocyanate or urea may also be used.

In one fiber-forming technique, fibers are first extruded from the protein solution through an orifice into methanol, until a length sufficient to be picked up by a mechanical means is produced. A fiber may then be pulled by such mechanical means through a methanol solution, collected, and dried. Methods for drawing fibers are considered well-known in the art. For example, fibers made from a 58 kDa synthetic MaSp consensus polypeptide were drawn by methods similar to those used for drawing low molecular weight nylons. Such methods are described in U.S. Pat. No. 5,994,099 and Lazaris et al. (2002, Science 295:472-476) the entire contents of which are incorporated herein by reference.

Of note, spider silk proteins have primary structures dominated by imperfect repetition of a short sequence of amino acids. A "unit repeat" constitutes one such short sequence. Thus, the primary structure of a spider silk protein may be thought to consist mostly of a series of small variations of a unit repeat. Unit repeats in a naturally occurring protein are often distinct from each other. In other words, there is little or no exact duplication of a unit repeat along the length of a protein. Synthetic spider silks, however, may be generated wherein the primary structure of a synthetic spider silk protein may be described as a number of exact repetitions of a single unit repeat. See FIG. 5 (SEQ ID NO: 3), which provides a nucleic acid sequence encoding a synthetic spider silk protein (SS1) comprised of sixteen repeats of a MaSp2 monomeric unit (FIG. 4; SEQ ID NO: 2). Additional synthetic spider silks may be designed comprising a number of repetitions of one unit repeat together with a number of repetitions of a second unit repeat. Such a structure would be similar to a typical block copolymer. The present invention also encompasses generation of synthetic spider silk proteins comprising unit repeats derived from several different spider silk sequences (naturally occurring variants or genetically engineered variants thereof).

Such synthetic hybrid spider silk proteins may each have 900 to 2700 amino acids with 25 to 100, preferably 30 to 90 repeats. A spider silk or fragment or variant thereof usually has a molecular weight of at least about 16,000 daltons, preferably 16,000 to 150,000 daltons, more preferably 50,000 to 120,000 daltons for fragments and greater than 100,000 but less than 500,000 daltons, preferably 120,000 to 350,000 for a full length protein.

C. Antibodies

The methods of the present invention also utilize antibodies capable of immunospecifically binding to spider silk proteins. Such antibodies may comprise polyclonal or monoclonal antibodies immunologically specific for a spider silk protein or functional fragments or derivatives thereof. Such antibodies may be used to advantage to identify and/or purify spider silk proteins. For example, antibodies may be utilized for affinity separation of a spider silk protein with which it immunospecifically interacts. Antibodies may also be used to immunoprecipitate a spider silk protein from a sample containing a mixture of proteins and other biological molecules. Other uses of anti-spider silk protein antibodies are described below.

III. Uses of Spider Silk-Encoding Nucleic Acids and Spider Silk Proteins

A. Spider Silk-Encoding Nucleic Acids

Spider silk protein-encoding nucleic acids may be used for a variety of purposes in accordance with the present invention. Spider silk protein-encoding DNA, RNA, or fragments thereof may be used as probes to detect the presence of and/or expression of genes encoding spider silk proteins. Methods in which spider silk protein-encoding nucleic acids may be utilized as probes for such assays include, but are not limited to: (1) in situ hybridization; (2) Southern hybridization; (3) northern hybridization; and (4) assorted amplification reactions such as polymerase chain reactions (PCR).

Host cells comprising at least one spider silk protein encoding DNA molecule are encompassed in the present invention. Host cells contemplated for use in the present invention include but are not limited to bacterial cells, fungal cells, insect cells, mammalian cells, and plant cells. In a preferred aspect of the present invention, spider silk proteins are expressed in plant cells in vitro. In a particularly preferred aspect of the present invention, spider silk proteins are expressed in plant cells in vivo. The spider silk protein-encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., *Current Protocols in Molecular Biology*, John Wiley & Sons, NY, N.Y. 1995, the disclosure of which is incorporated by reference herein.

As described above, spider silk protein-encoding nucleic acids may also used to advantage to produce large quantities of substantially pure spider silk proteins, or selected portions thereof.

B. Proteins and Antibodies

Purified spider silk protein, or fragments thereof, produced by methods of the present invention may be used to advantage in a variety of different applications, including, but not limited to, production of fabric, sutures, medical coverings, high-tech clothing, rope, reinforced plastics, and other applications in which various combinations of strength and elasticity are required.

Table I lists physical properties of various biological and manmade materials

| Material | Material Strength ($N\,m^{-2}$) | Elasticity (%) | Energy to Break ($J\,kg^{-1}$) |
| --- | --- | --- | --- |
| Dragline Silk | $4 \times 10^9$ | 35 | $1 \times 10^5$ |
| Minor Silk | $1 \times 10^9$ | 5 | $3 \times 10^4$ |
| Flagelliform Silk | $1 \times 10^9$ | 200+ | $1 \times 10^5$ |
| KEVLAR | $4 \times 10^9$ | 5 | $3 \times 10^4$ |
| Rubber | $1 \times 10^9$ | 600 | $8 \times 10^4$ |
| Tendon | $1 \times 10^9$ | 5 | $5 \times 10^3$ |

Data derived from Gosline et al (9) and Stauffer et al (18).

As shown in Table I, spider silks are characterized by advantageous physical properties, including, but not limited to, high tensile strength and pronounced elasticity, that are highly desirable for numerous applications. It is significant to note that spider silks possess these physical properties in aggregation which renders them unique proteins having unparalleled utility. For example, spider dragline silk has a tensile strength greater than steel or carbon fibers (200 ksi), elasticity as great as some nylon (35%), a stiffness as low as silk (0.6 msi), and the ability to supercontract in water (up to 60% decrease in length). In view of its high tensile strength and elasticity, the energy required to break dragline silk exceeds that required to break any known fiber including Kelvar™ and steel. These properties are unmatched by any known natural or manmade material. Moreover, the new materials of the present invention would also provide unique combinations of such desirable features in a very low weight material.

In view of the foregoing advantageous properties, incorporation of spider silk proteins expressed in plant cells into materials used to generate a product would produce a superior product. When spider silk is dissolved in an appropriate solvent and forced through a small orifice to generate spider silk fibers, such fibers may be woven into a fabric/material or added into a composite fabric/material. For example, spider silk fibers may be woven into fabrics to modulate the strength and elasticity of a fabric, thus rendering materials comprising such modified fabric optimized for different applications. Spider silk fibers may be of particular utility when incorporated into materials used to make high-tech clothing, rope, sails, parachutes, wings on aerial devices (e.g., hang gliders), flexible tie downs for electrical components, sutures, and even as a biomaterial for implantation (e.g., artificial ligaments or aortic banding).

Biomedical applications involve use of natural and/or synthetic spider silk fibers produced by the methods of the present invention in sutures used in surgical procedures, including, but not limited to: eye surgery, reconstructive surgery (e.g., nerve or tympanic membrane reconstruction), vascular closure, bowel surgery, cosmetic surgery, and central nervous system surgery. Natural and synthetic spider silk fibers may also be of utility in the generation of antibiotic impregnated sutures and implant material and matrix material for reconstruction of bone and connective tissue. Implants and matrix material for reconstruction may be impregnated with aggregated growth factors, differentiation factors, and/or cell attractants to facilitate incorporation of the exogenous material and optimize recovery of a patient. Plant-expressed spider silk proteins and fibers may be used for any application in which various combinations of strength and elasticity are required. Moreover, spider silk proteins may be modified to optimize their utility in any application. As described above, sequences of spider silk proteins may be modified to alter various physical properties of a fibroin and different spider silk proteins and variants thereof may be woven in combination to produce fibers comprised of at least one spider silk protein or variant thereof. In a preliminary study designed to evaluate the potential for an immune response to a natural spider silk protein, natural dragline silk was implanted into mice and rats intramuscularly, intraperitoneally, or subcutaneously. Animals into which natural dragline silk was introduced did not mount an immune response to the spider silk protein, irrespective of the site of implantation. Of note, tissue sections surrounding spider silk protein implants were essentially identical to tissue sections derived from implantation sites into which a polyethylene rod was inserted. Since a polyethylene rod was used as the solid matrix about which the dragline spider silk protein was wrapped prior to implantation, introduction of a polyethylene rod alone serves as a negative control for such experiments. In view of the above, spider silk proteins of the present invention are expected to elicit minimal immunological responses when introduced into vertebrate animals.

Synthetic spider silk fibers are of utility in any applications for which natural spider silk fibers may be used. For example, synthetic fibers may be mixed with various plastics and/or resins to prepare a fiber-reinforced plastic and/or resin product. Because spider silk is stable up to 180° C., spider silk protein fibers would be of utility as structural reinforcement material in thermal injected plastics.

It should be apparent from the foregoing that spider silk proteins expressed in plants may be generated in large quantities by means generally known to those of skill in the art and described herein. Spider silk proteins and derivatives thereof can be made into fibers for any intended use. Moreover, mixed composites of fibers are also of interest as a consequence of their unique combined properties. Such mixed composites may confer characteristics of flexibility and strength to any material into which they can be incorporated.

Polyclonal or monoclonal antibodies immunologically specific for a spider silk protein may be used in a variety of assays designed to detect and quantitate spider silk proteins. Such assays include, but are not limited to: (1) flow cytometric analysis; and (2) immunoblot analysis (e.g., dot blot, Western blot) of extracts from various cells. Additionally, anti-spider silk protein antibodies may be used for purification of a spider silk protein and any associated subunits (e.g., affinity column purification, immunoprecipitation).

From the foregoing discussion, it can be seen that the methods of the present invention may be used, for example, to: 1) transform plant cells from which transgenic plants may be derived; 2) express large quantities of spider silk proteins (e.g. natural or synthetic spider silk proteins) in plant cells in vitro and in vivo; 3) purify large quantities of these spider silk proteins; 4) draw fibers comprised of plant-expressed spider silk proteins; 5) weave these spider silk fibers, singly and in combination, into fabric; and 6) detect expression of spider silk proteins in cells and/or organisms.

Methods of Use for Nucleic and Amino Acid Sequences and Antibodies

Synthetic genes have been constructed which encode 4, 8, 16, and 32 units of the consensus repeat sequence of MaSp1 and MaSp 2 (17). The method involved starts with a DNA representing the consensus sequence for the silk, which is repeatedly doubled using compatible but non-regenerable restriction enzymes until the desired size is reached. Each of these constructs has been shown to produce a protein of the expected size in $E.$ $coli$. The 16 monomeric repeat MaSp2-derived protein has been over-expressed in $E.$ $coli$ to a level that has facilitated the synthesis of over 25 grams of purified protein from a series of 10 liter cultures. Although this is useful for analytical purposes, insufficient amounts were produced by this approach for commercial applications. Methods are provided herein for the generation of additional synthetic spider silk proteins. See Example IV.

The following examples are provided to illustrate embodiments of the invention. They are not intended to limit the scope of the invention in any way.

Example I

Generation of *Arabidopsis* Plants Expressing Synthetic Spider Silk Protein (SS1)

In order to express a spider silk protein in a transgenic plant, a nucleic acid sequence (SEQ ID NO: 3) which encodes a synthetic spider silk protein (SS1) was constructed and subcloned via multiple intermediate vectors into pIBT110. pIBT110 is a plant expression vector which has been shown to drive the expression of high levels of exogenous molecules (e.g., RNA and protein) in a variety of plant cells in vitro and in vivo, including *Arabidopsis* cells. As described below, pIBT110 comprising SEQ ID NO: 3 was utilized in the transformation of *Arabidopsis* plants, which resulted in the expression of synthetic spider silk protein in these plants. Similar methods may be used to express other synthetic spider silk proteins, such as but not limited to, the synthetic spider silk proteins described herein. See Example IV.

The following protocols are provided to facilitate practice of the methods of the present invention.

Methods and Materials

Western blotting to demonstrate steady state SS1 protein in transgenic *Arabidopsis*. Leaves from individual transgenic *Arabidopsis* plants were ground in liquid nitrogen followed by addition of buffer (50 mM Tris-Cl, pH 8.0, 10 mM MgCl, 100 mM NaCl) at a ratio of 1 g tissue:1 ml buffer. The lysate then centrifuged at 10,000×g for 10 minutes at 5° C. The supernatant was removed and subjected to SDS polyacrylamide gel electrophoresis. The gel was blotted onto nitrocellulose and air dried for 5 minutes. The blot was incubated in Blotto (1 M Tris-Cl, pH 7.8, 2 M NaCl, 3% non-fat dried milk) for 2 hours at room temperature. The wet blot was then incubated in fresh Blotto plus MaSp2 antiserum at a 1:2000 dilution overnight at 4° C. with shaking. Subsequently, the blot was washed three times for 15 minutes each in Blotto at room temperature. The blot was then incubated in Blotto minus dried milk plus anti-IgG-peroxidase (1:15,000 dilution) for 1 hour at room temperature with shaking. The blot was then washed six times in Blotto minus milk for 15 minutes each wash. Subsequently, the blot was immersed in chemiluminescence substrate for 1 minute followed by rinsing with distilled water for 10 sec and exposure to X-ray film.

Northern blotting to demonstrate SS1 mRNA production in transgenic *Arabidopsis*. Total RNA from transgenic lines was extracted using a Gentra kit. The RNA samples were resolved on a 1.0% denaturing formaldehyde gel. The gel was rinsed in deionized water and blotted onto a Zeta probe membrane. The blot was rinsed in 6×SSC, allowed to air dry and baked in vacuo at 80° C. for 30 minutes. The SS1 probe was prepared and hybridized to the blot as described below for Southern blotting.

Southern blotting to demonstrate SS1 gene insertion into *Arabidopsis*. Genomic DNA from putative transgenic $T_2$ *Arabidopsis* plants was purified using a DNA kit from Gentra, Inc. DNA was then digested with BamH1. As a positive control the synthetic MaSp2 gene (SS1) was digested from pET19. The DNAs were resolved on an agarose gel, followed by depurination in 0.25M HCl for 25 minutes and washing in deionized water. DNA was then denatured in 1.5M NaCl/0.5M NaOH for 30 minutes, washed in sterile deionized water, and neutralized in 1.5M NaCl/0.5M Tris-Cl (pH 7) for 30 minutes followed by a final wash in deionized water. The gel was blotted onto a Zeta probe membrane, washed in 2×SSC and dried in vacuo.

The probe was prepared by digesting pET19 with BamH1 to release the SS1 sixteen repeat fragment followed by purification of the SS1 gene. The resultant DNA was radiolabeled using a random priming kit (Sigma). The labeled probe was purified by spin column chromatography. Blots were prehybridized in 6×SSC, 5×Denhardt's solution, 0.5% SDS, 100 mg/ml ssDNA for 3 hours at 45° C. The labeled probe was then added to the solution and incubation continued overnight at 45° C. Subsequently the blot was washed in 2×SSC, 0.2% SDS with shaking for 10 minutes and then in 0.2×SSC/0.1% SDS at room temperature for 10 minutes. The blot was then exposed to X-ray film.

Results

In order to determine if spider silk could be produced in a large scale and stable manner by transgenic plants, a nucleic acid sequence (SEQ ID NO: 3) which encodes a synthetic spider silk protein was constructed and subcloned via multiple intermediate vectors into pIBT110. As described above, SEQ ID NO: 3 comprises sixteen repeats of a monomeric unit (SEQ ID NO: 2) which was based on a unit repeat of MaSp2 (FIG. 3; SEQ ID NO: 1). The final construct (pIBT110-SS1) was determined to be in the proper reading frame and flanked by multiple in-frame histidine (His) sequences that allowed affinity purification of the expressed protein. The vector pIBT110 was used because it is commercially available and drives high level expression of proteins in plants. In addition to the required signal sequences for foreign gene incorporation, the vector also comprises the cauliflower mosaic virus (CaMV) 35S promoter, duplicated enhancers linked to the tobacco etch 5'untranslated leader region (UTR), the soybean vspB 3' UTR and polyadenylation signal. The presence of a kanamycin resistance gene selectable marker also facilitates selection of transformed plants with kanamycin.

The presence of the fragment containing the synthetic spider silk DNA in pIBT110 was confirmed by restriction endonuclease analysis of isolated plasmid. The pIBT110 plasmid was then shuttled into *Agrobacterium tumefaciens*. This bacterium is a plant pathogen which has the ability to insert DNA that is flanked by specific targeting sequences into the plant genome. Once inserted, the foreign DNA is typically replicated concordant with that of the genomic DNA of the transformed plant, generation to generation in a stable inherited fashion. The *A. tumefaciens* used in this study has been disarmed such that only essential transfer sequences remain. Thus, transformation with such vectors does not incite disease.

The pIBT110 construct comprising the synthetic spider silk (pIBT110-SS1; FIG. 1) was transformed into *Agrobacterium tumefaciens* and then introduced into *Arabidopsis thaliana* by standard techniques (11). *Arabidopsis* is a model plant system because these plants are easily transformed and regenerated, and grow very rapidly. In this example, *A. thaliana* was infected by the floral dipping method. See above protocol and the following website, www.arabidopsis.org, the entire contents of which is incorporated herein by reference. Putative transformed seeds were selected by plating on kanamycin plates, followed by transplantation to soil mix under greenhouse conditions.

Western blotting of extracts derived from $T_1$ and $T_2$ plants established that spider silk was stably expressed. See FIG. 6. In FIG. 6, the expression of synthetic spider silk protein in Transgenic *Arabidopsis* is shown. Lanes 1-5 were loaded with varying concentrations of recombinant MaSp2 protein purified from *E. coli*. Lanes 6-7 contained the protein crude extracts from transgenic *Arabidopsis* transformed with the synthetic silk gene using pIBT110. 1× was no dilution, 0.2× was 5 times dilution from the crude extract. Lane 8 was the control plant transformed with pIBT110 plasmid only.

In FIG. 7, a Southern blot analysis of the silk transgene and its copy number in transgenic *Arabidopsis* plants is shown. Genomic DNA extracted from $T_2$ transgenic lines #5, #6 (lane 4, 5 respectively) and from plants transformed with pIBT110 plasmid only (lane 6) was digested with BamHI. Plasmid DNA from the pET19 vector containing the synthetic silk gene was also digested with BamH1. The silk gene fragment was random labeled and used as a probe in Southern hybridization. After calculating the ratio between pET19SS (7.1 kb) and the *Arabidopsis* genome (125,000 kb), the loading amount of genomic DNA and plasmid DNA was used to show a single copy. About 18 ug of digested genomic DNA was loaded in lane 4-6, and 0.2 ng, 1 ng and 5 ng digested plasmid DNA were loaded in lanes 1-3, respectively, as a standard. The intensity of the bands was compared between standards and plant samples to determine copy number.

In FIG. 8, Northern blot analysis of transgene expression is shown. Total RNA was extracted from *Arabidopsis* leaves and about 1.0 ug of total RNA per lane was blotted onto a zeta-probe membrane (lane 1-3). Probe was the same as in Southern blot. The total RNA from plant transformed with pIBT110 plasmid only was also prepared as a control shown in lane 4. The mRNA size was marked as an arrow.

Notably, *Arabidopsis* plants transformed to express SS1 protein were phenotypically normal. This study has provided the foundation to engineer additional crop plants using the methods of the present invention.

Example II

Generation of *Arabidopsis* Plants Expressing Native Spider Silk Proteins

Natural or native nucleic acid sequences, such as *Nephila clavipes* dragline silk fibroin mRNA (SEQ ID NO: 1; FIG. 3), *Argiope trifasciata* aciniform fibroin 1 (SEQ ID NO: 4; FIG. 9), *Phidippus audax* fibroin 1 (SEQ ID NO: 5; FIG. 10); *Zorocrates* sp. fibroin 1 (SEQ ID NO: 6; FIG. 11); *Kukulcania* MaSp (SEQ ID NO: 7; FIG. 12); *Kukulcania* MaSp (SEQ ID NO: 8; FIG. 13); *Kukulcania* MaSp (SEQ ID NO: 9; FIG. 14); *Argiope* MiSp (SEQ ID NO: 10; FIG. 15); and *Argiope* MiSp (SEQ ID NO: 11; FIG. 16) may be subcloned into a plant expression vector (e.g., pIBT110). Such methods may be used to express amino acid sequences comprising *Argiope trifasciata* aciniform fibroin 1 (SEQ ID NO: 15; FIG. 9), *Phidippus audax* fibroin 1 (SEQ ID NO: 16; FIG. 10), *Zorocrates* sp. fibroin 1 (SEQ ID NO: 17; FIG. 11); *Kukulcania* MaSps (SEQ ID NOs: 7, 8, 9; FIGS. 12, 13, and 14, respectively); and *Argiope* MiSps (SEQ ID NOs: 10 and 11; FIGS. 15 and 16, respectively). Spider silk proteins may also be expressed in plants as fusion proteins comprising a spider silk protein operably linked to a tag moiety (e.g. His or myc tag). Methods for producing fusion proteins are disclosed herein and known to those skilled in the art. The incorporation of such tags facilitates detection and purification of a spider silk fusion protein expressed in a plant cell. A pIBT110 construct comprising SEQ ID NO: 1, 4, 5, 6, 7, 8, 9, 10, or 11 may be transformed into *Agrobacterium tumefaciens* and positive transformants selected on antibiotic media as described above. *Arabidopsis*, for example, may be infected with *Agrobacterium* transformed with a pIBT110 expression vector comprising SEQ ID NO: 1, 4, 5, 6, 7, 8, 9, 10, or 11 by the floral dipping method. Seed may be collected and positive transformants selected on kanamycin plates. $T_1$ plants may be generated, allowed to self-fertilize, and seed collected therefrom for analysis. Extracts may be isolated from $T_1$ plants transformed with pIBT110-MaSp2, for example, and analyzed by immunoblotting using antiserum immunologically specific for the spider silk protein MaSp2. Extracts isolated from $T_1$ plants transformed with a pIBT110 expression vector comprising SEQ ID NO: 4, 5, 6, 7, 8, 9, 10, or 11 may be analyzed by immunoblotting with the appropriate immunologically specific antibodies. For embodiments in which spider silk proteins are expressed as fusion proteins, antibodies specific for the tag moiety may be used to detect the fusion protein on immunoblots. As described above, standard procedures may be used to perform the above Western blotting experiments. Expression of natural spider silk proteins in plants may provide an additional resource for the production of spider silk proteins having desirable qualities for diverse applications.

Example III

Generation of Alfalfa Plants Expressing High Levels of Spider Silk Protein

Figure 2:
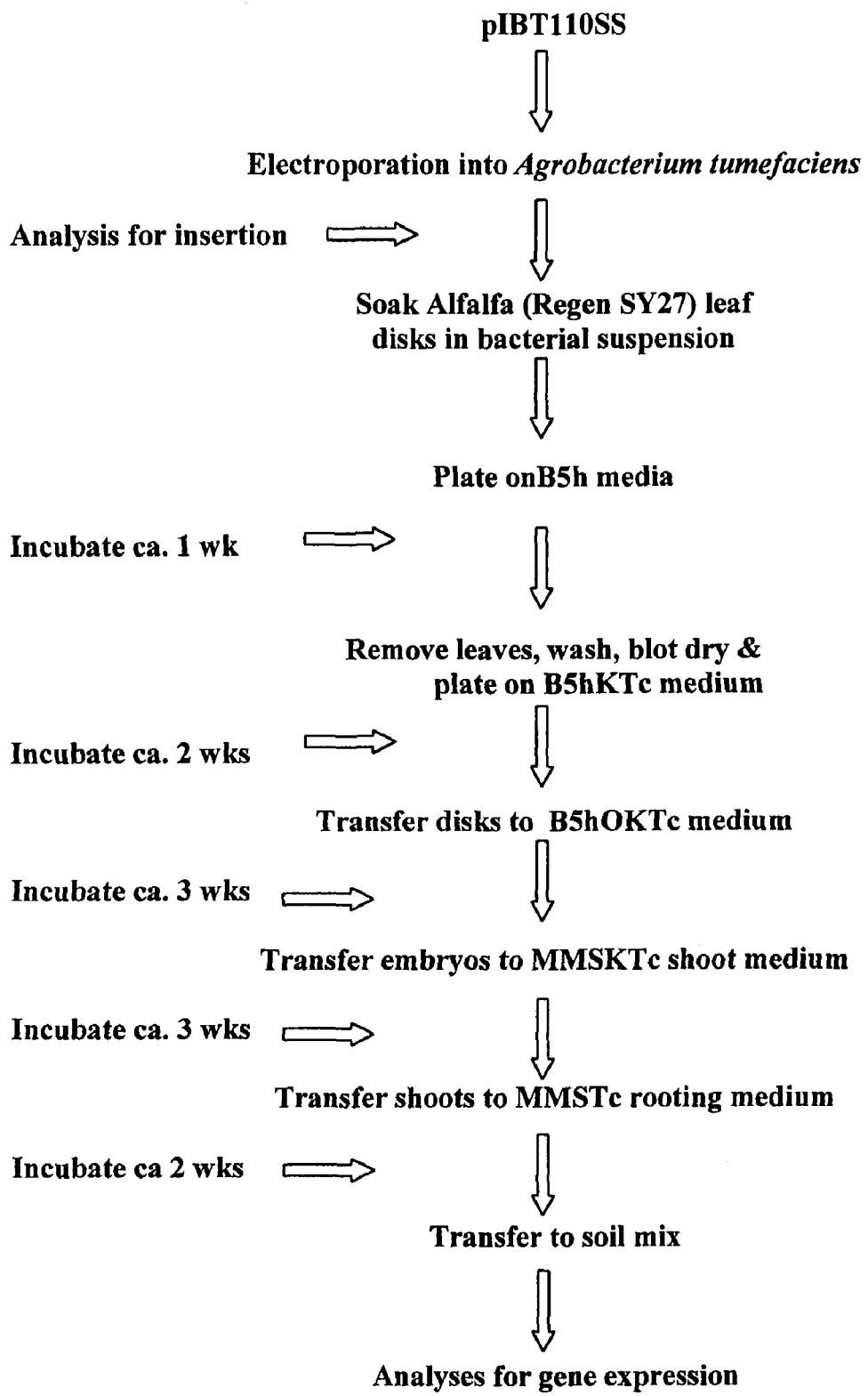
FIG. 2 shows a flow chart of the transformation and selection of transgenic plants.
Figure 6:
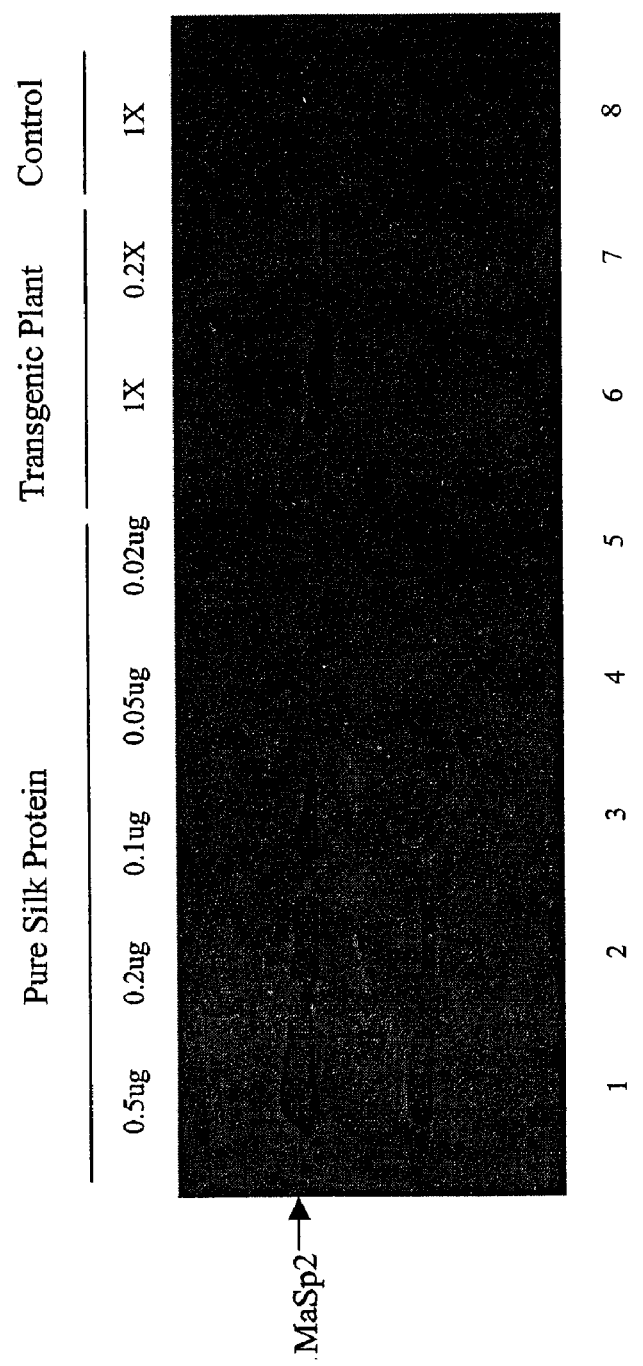
FIG. 6 shows a Western blot of *Arabidopsis* cellular lysates probed with an antibody immunologically specific for MaSp2 protein.
Figure 7:
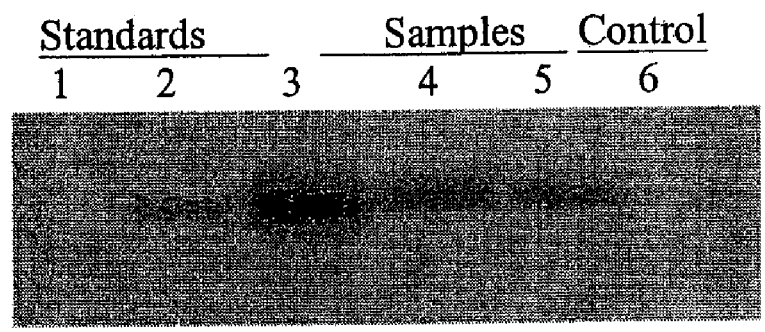
FIG. 7 shows a Southern blot of DNA isolated from transgenic *Arabidopsis* plants and probed with a SS1 specific probe.
Figure 8:
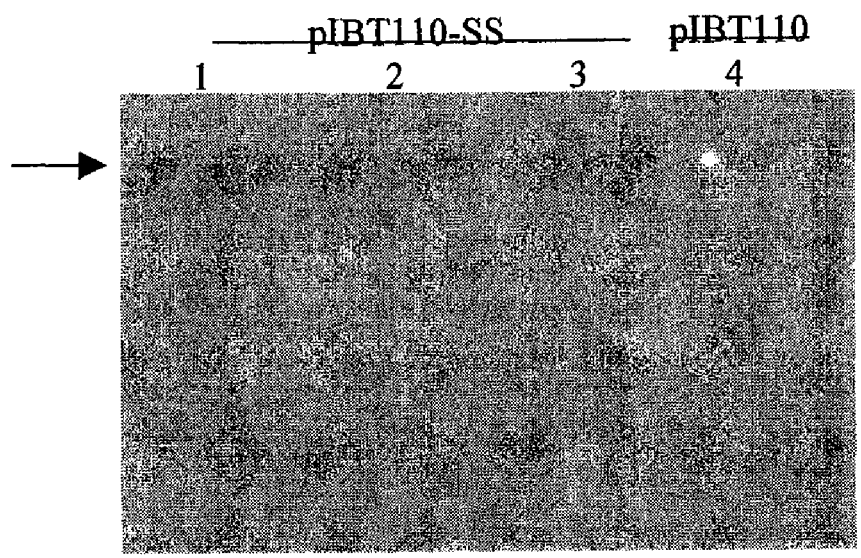
FIG. 8 shows a Northern blot of RNA isolated from transgenic *Arabidopsis* plants and probed with a SS1 specific probe.

As described above, the *Nephila clavipes* dragline silk fibroin synthetic DNA (SEQ ID NO: 3) was subcloned into the plant expression vector pIBT110. Alfalfa may be transformed with the pIBT110 empty vector as a control and with pIBT110-SS1, for example, according to the procedure of D. A. Samac (University of Minnesota, pers. communication). A flow chart depicting a process for transforming alfalfa and selecting positive transformants is provided in FIG. 2. Briefly, excised leaf discs may be soaked in an *Agrobacterium* suspension (described elsewhere herein) and subsequently replated on different media to generate callus, shoots, and roots.

In a preferred embodiment, alfalfa may be transformed to express any natural and/or synthetic spider silk protein described herein. This procedure is based upon co-cultivation of surface sterilized alfalfa leaves (variety Regen SY27) with *A. tumefaciens* for 15 minutes. Regen SY27 was selected because it is easily agro-transformed and amenable to tissue culture. Inoculated leaves may be transferred to B5h plates to allow plant cell growth in vitro (1, 3). Following incubation for seven days, leaf pieces may be rinsed in sterile water and transferred to B5hKTc selection plates (1, 3). B5hKTc medium contains 25 mg/L kanamycin and 500 mg/L carbenicillin to effect selection of transformants and kill remaining bacterial cells associated with the leaves, respectively. Within two weeks of infection by *A. tumefaciens*, callus begin to grow from transformed cells that are resistant to the kanamycin. These cells may be transferred to B5hOKTc media (1, 3) that lack hormones, thus allowing embryo and shoot growth.

Green plantlets may be transferred to MMSTc rooting medium (1, 3) that lacks kanamycin and allows root generation. Following formation of a vigorous root system, plants may be transplanted to soil mix and grown under growth chamber conditions. Fifty individual kanamycin resistant plantlets that represent apparent separate transformations may be selected for further testing. Insertion of the target gene from pIBT110 into the plant genome occurs in an essentially random fashion, thus, screening must be done to establish incorporation of the gene and determine the number of inserts or fragments incorporated. Additionally, the expression level of the encoded spider silk protein may vary between independent transformants and must be quantified. Multiple transformations may be examined to ensure that sufficient plants are available for selection procedures.

Regeneration and selection of transformants. Plants into which pIBT110-SS1, for example, has been incorporated are rendered resistant to kanamycin and referred to herein as primary transformants ($T_0$). $T_0$ plants may be analyzed to evaluate their phenotype and vegetatively propagated to obtain sufficient plant material for testing. Initial assays to establish SS1 gene expression may be performed by isolating extracts prepared from plant leaves transformed with empty pIBT110 vector (control) or pIBT110-SS1 and analyzing them by immunoblotting with antibodies immunologically specific for MaSp2. Additional controls may comprise purified MaSp2 protein alone and in the presence of plant extracts.

In brief, leaf tissue from transformants may be frozen in liquid nitrogen and ground into a fine powder. Buffer may be added (as described in reference 4) and the homogenate filtered through four layers of sterile cheesecloth followed by centrifugation at 10,000×g for 15 minutes. Proteins in the supernatant may be resolved by SDS-polyacrylamide gel electrophoresis (SDS-PAGE) followed by blotting onto nitrocellulose membranes. Membranes may be incubated with pre-hybridization blocking buffer (6, 7) followed by incubation with antiserum immunologically specific for MaSp2 (provided by Nexia Biotechnologies). Following hybridization, the membranes may be thoroughly washed and incubated in hybridization buffer containing secondary antibody conjugated to horseradish peroxidase. Unbound antibody may be removed by washing. Washed membranes may be immersed in chemiluminescence solution and the chemiluminescent signal detected by exposing the membranes to X-ray film. This technique is used routinely in research laboratories and is well known to those skilled in the art. See references 6 and 7. This method affords an estimation of the relative SS1 expression levels among transformed plants. Since spider silk protein is not effectively detected by Coomassie Blue staining techniques, the immunoblotting approach as described above provides workable means with which to compare SS1 expression levels among transformed plants.

The phenotype of transgenic plants may be evaluated based upon comparisons among non-transgenic parent plants, pIBT110 only transformed plants, and silk-expressing transformed (e.g., pIBT110-SS1) plants based on the following parameters: germination time, percentage germination, plant height at two weeks, one and three months, time to flowering, flower number and dry matter at harvest. In addition, visual examinations may be done throughout the growth cycle. Data may be collected for 30 individuals in each line and statistically evaluated to determine if silk expression and/or the level of silk expression affects phenotype. As described in Example I, measurements of transgenic *Arabidopsis* plants transformed to express SS1 revealed that spider silk expression did not effect phenotype in these plants. In brief, ten transgenic alfalfa lines shown to express high levels of protein and exhibit a normal phenotype as compared to controls will be selected for further analyses.

Molecular assays of transgenic plants for gene insertion and expression. Following propagation of transgenic plants, detailed molecular analyses of the transgene insert may be performed to ensure continued, appropriate expression and to identify any events (such as multiple insertion or insertion of SS1 fragments) that may be unacceptable from a functional and/or regulatory perspective. These experiments may be used to establish the copy number of inserted spider silk encoding DNA (e.g. SS1) in a transformed alfalfa genome, determine the level of mRNA production, and confirm protein expression levels. Southern blotting may be used to evaluate the presence and copy number of spider silk DNA in the genome.

Plant DNA may be isolated using the cetyl trimethyl ammonium bromide (CTAB) procedure wherein leaf tissue homogenate in CTAB buffer is incubated in 5% Sarkosyl for 60 minutes at 60° C. with mixing, followed by chloroform/octanol extraction and ethanol precipitation of DNA (12). As described above, the treated DNA may be digested with BamH1, resolved on an agarose gel, and transferred to a nylon membrane. The DNA may be crosslinked to the membrane by exposure to UV light. The membrane may be incubated with prehybridization buffer followed by hybridization buffer containing a denatured complementary SS1 oligonucleotide probe. The probe may be labeled by nick translation to a specific activity $>1\times10^8$ dpm/mg. Following hybridization, the membrane may be thoroughly washed and signal developed by autoradiography. Such methods may be used to establish the productive insertion of spider silk DNA into the alfalfa genome.

For Northern blotting, total RNA may be isolated as previously described (12) and resolved on a 1.5% agarose gel under denaturing conditions followed by electro-blotting onto a Zeta-Probe membrane. RNA may be fixed to the filter by ultraviolet crosslinking. Hybridizations may be performed as described (10) using a degenerate synthetic oligonucleotide probe of the spider silk nucleotide sequence. The probe may be labeled by nick translation using $^{32}$P-DATP according to standard procedures (10). Following extensive washing of the filter, bands may be visualized by autoradiography. Each of these procedures may be performed according to established protocols.

Protocols for the isolation and purification of spider silk from alfalfa. Protocols for the efficient isolation of spider silk from plants may be necessary for large-scale industrial and medical uses. The SS1 protein, for example, may be expressed as a fusion protein in which the SS1 sequences have been operably linked to multiple His sequences to facilitate affinity purification of spider silk protein on nickel columns. Such purification methods may be used to advantage for small scale characterization studies.

Affinity purification strategies amenable for large-scale applications, however, are desirable. Affinity purification gauged for large-scale applications may be performed as follows: leaves may be homogenized by grinding in extraction buffer (50 mM Tris, pH 6.5, 10 mM $MgCl_2$ and 100 mM NaCl) and filtered through four layers of sterile cheesecloth. Following centrifugation at 10,000×g for 15 minutes, the supernatant may be incubated for 30 minutes with the nickel resin. Unbound supernatant may be removed by vacuum filtration and the resin washed in 10 volumes of binding buffer (5 mM imidazole, 500 mM NaCl, 20 mM Tris-Cl, pH 7.9) followed by 6 volumes of wash buffer (60 mM imidazole, 500 mM NaCl and 20 nM Tris-Cl, pH 7.9). Following filtration to remove any residual liquid, the protein may be eluted using 300 ml of stripping buffer (100 mM EDTA, 500 mM NaCl and 20 mM Tris-HcL, pH 7.9). The elutant may be dialyzed, lyophilized, and re-solubilized in sterile water prior to immunoblotting analysis as described above. This procedure may be used to yield an analytical amount of silk protein for quantitation by amino acid analysis. This procedure has been utilized extensively to analyze silk expression from *E. coli*. See Lewis et al. (1996, Protein Expression and Purification 7:400). Using this approach, silk protein expression in transgenic plants may be determined as a percentage of total protein and as a percentage of dry and fresh weight.

Alternatively, standard purification strategies designed to differentially isolate silk protein from plant homogenates may be used to advantage. Such methods are described in Scheller et al. (2001, Nature Biotechnology 19:573), the entire contents of which is incorporated herein by reference. Purification of the expressed spider silk protein may be facilitated by its extreme stability under conditions that denature typical proteins, such as, for example, high heat and low pH. Accordingly, general protein purification strategies may be adapted to optimize silk purification from leaves. Aboveground portions of transgenic plants may be harvested and allowed to air dry as per normal production practices. The "hay" may be homogenized in buffer (see reference 4) followed by various treatments designed to differentially eliminate contaminants.

Development of a specific purification protocol is essentially an empirical process and silk protein recovery may be optimized following treatments in which homogenates are subject to individual and/or combinations of 1) boiling for various times in the presence or absence of detergent; 2) differential centrifugation; 3) progressively decreasing the pH; and 4) precipitation with varying concentrations of urea or ammonium sulfate. One of ordinary skill in the art may vary the above treatments to optimize the yield and efficiency of purification of spider silk proteins from plants.

The level of silk protein may be determined by immunoblotting and the purity and concentration assessed definitively by amino acid analysis. Purified silk protein may be analyzed for mechanical properties as previously described (18) to ensure that the recombinant protein possesses the desired properties.

The material remaining after silk extraction may be subject to compositional analyses according to standard protocols. Such data may be used to advantage in evaluating the suitability of the material as a feed crop.

Introduction of the trait into cultivars adaptable to geographic regions. Following regeneration of shoots and roots, positive transformants ($T_0$ transgenic plants) may be selected, grown to flowering, and hybridized to any alfalfa strain optimized for growth in a particular geographical region. In one embodiment, for example, the transformants may be hybridized to diverse alfalfa breeding materials specifically adapted to various environmental conditions (as described in 1, 16). These materials are available from the Groose collection. Backcrossing may be used to advantage to (a) confirm stable Mendelian transmission of the SS1 gene in alfalfa chromosomes, (b) remove any unwanted somoclonal variation (deleterious mutations) arising from the cell culture/transformation process, and (c) take the first step towards concentrating the spider silk gene from primary transformants (hemizygote simplex genotype Sxxx, where S=silk) to develop a population (cultivar) of autotetraploid alfalfa plants that are primarily triplex (SSSx) or quadriplex (SSSS) to ensure high levels of silk protein production in a finished cultivar. Backcrossing may be done under greenhouse conditions and progeny qualitatively and quantitatively evaluated for silk expression by immunoblotting to provide information pertaining to statistical analysis and further selection.

Example IV

Exemplary Methods for Designing Synthetic Spider Silk Proteins for Expression in Plants The following methods for designing synthetic spider silk proteins are based on the amino acid composition of spider silk proteins and how repetitive regions of amino acid sequences contribute to the structural/physical properties of spider silk proteins.

Synthetic spider silk proteins may be comprised of a series of tandem exact repeats of amino acid sequence regions identified as possessing a particular spectrum of physical properties. Exact repeats comprise regions of amino acid sequences that are duplicated precisely. Alternatively, synthetic spider silk proteins may be comprised of a series of tandem inexact repeats identified as having a spectrum of physical properties. Inexact repeats may comprise regions of amino acid sequences in which at least one amino acid in the basic inexact repeat unit has been altered as long as the alteration does not change the spectrum of physical properties characteristic of the basic inexact repeat unit remain the same.

In order to increase the tensile strength of a minor ampullate silk, for example, to adapt it for applications in which strength and very little elasticity are needed, such as bulletproof vests, the (GA)n regions may be replaced by (A)n regions. This change would increase the tensile strength. The typical MiSp1 protein has sixteen (GA) units. Replacing eight (GA) regions, for example, with (A) regions would increase the tensile strength from 100,000 psi to at least 400,000 psi. Moreover, if the (A)n regions were as long as the (GA)n regions the tensile strength would increase to greater than 600,000 psi.

To create a fiber with high tensile strength and greater elasticity than major ampullate silk, the number of (GPGXX; SEQ ID NO: 24) regions may be increased from 4-5 regions, the range of (GPGXX; SEQ ID NO: 24) regions typically found in naturally occurring major ampullate spider silk proteins, to a larger number of regions. For example, if the number were increased to 10-12 (GPGXX; SEQ ID NO: 24) regions, the elasticity would increase to 50-60%. If the number were further increased to 25-30 regions, the elasticity would be near 100%. Such fibers may be used to advantage in coverings for wounds (for example, burn wounds) to facilitate easier placement and provide structural support. Such fibers may also be used for clothing and as fibers in composite materials.

The tensile strength of a very elastic flagelliform silk may be increased by replacing some of the (GPGXX; SEQ ID NO: 24) units with (A)n regions. A flagelliform silk protein contains an average of 50 (GPGXX; SEQ ID NO: 24) units per repeat. Replacing two units in each repeat with (A) regions may, therefore, increase the tensile strength of a flagelliform silk by a factor of four to achieve a tensile strength of about 400,000 psi. Uses for such flagelliform silk proteins are similar to those described for major ampullate proteins having augmented elasticity (as described hereinabove). The flagelliform proteins have additional utility in that the spacer regions therein confer the ability to attach functional molecules like antibiotics and/or growth factors (or combinations thereof) to composites comprising flagelliform proteins.

Synthetic spider proteins may also comprise the following elastic sequence motifs: GPGQQGPGQQ (SEQ ID NO: 25), from *Araneus* dragline; GPGGYGPGPGGQQG (SEQ ID NO: 26) from *Lactrodectus* dragline; and GPGAGQQGPG-SQGPGSGGQQGPGQQ (SEQ ID NO: 27), from *Argiope* dragline. Genes comprising 2, 4, 8 and 16 repeats of these motifs may be constructed. The naturally occurring linker, GPYGPGS (SEQ ID NO: 28), connected to a poly-alanine segment of eight residues may be used to flank each repeat unit. The poly-alanine segment may be used as in the natural protein for fiber formation. This entire unit may be increased up to 16 repeat units to generate an encoded protein of 70-80 kD. Varying the number of these motifs alters the amount of elasticity from about 30% (for a synthetic spider silk protein comprising two repeats derived from *Araneus*) to nearly 200% (for a synthetic spider silk protein comprising sixteen repeats derived from *Argiope*). Varying the sequence of the motifs modifies the elastic modulus (higher with *Araneus*, lower with *Argiope*).

Genes encoding synthetic spider proteins derived from one of the *Araneus* MaSp2 protein analog genes may also be constructed. Such *Araneus* MaSp2 protein analog genes comprise β-sheet motifs from poly-alanine segments of 5 and 14 residues that are the smallest and largest poly-alanine tracts found in the major ampullate silk proteins. These segments may also be constructed the novel sequence motif (gly-ala or gly-val)$_n$ with the numerical value of n ranging from 3 to 8, the range observed in natural spider silk proteins. Varying the length and sequence of the β-sheet region alters the tensile strength from approximately that of the typical minor ampullate silk (100,000 psi) to at least 600,000 psi, double that of dragline silk. Moreover, the specific sequence of the repeat influences the tensile strength of the fiber.

Table II shows spider silk protein unit repeats of utility in the construction of synthetic spider silk protein.

| Elastic | Hard | Linker | Helix |
|---|---|---|---|
| GPGGYGPGQQ (29) | (A)$_n$ | GPSGPGS (36) | 20) (GGX)$_n$ |
| GPGQQGPGQQ (25) | (GA)$_n$ | GPYGPS (37) | X = Y, L, Q, V, A, S |
| GPGGYGPGPGXQQGY (30) | (GV)$_n$ | GPYGPG (38) | |
| GPGAGQQGPSQGPGSGGQQGPGGQ (31) | (AQ)$_n$ | GPGGPG* (39) | |
| GPGSGQQGPGQQGPGSGGQQGPGGQ (32) | (AY)$_n$ | GPGGPGSS* (40) | |
| GPGGYGPGSQGPSGPGAY* (33) | | GPSGPGGAS* (41) | |
| GPGGQGPGQQGPGGY* (34) | | GPGSG (42) | |
| GPGGX (35) with X = A, Y, S, V | | | |

*= a novel motif; n = 4-14, more likely 4-8.
Numbers in parenthesis are utilized to indicate SEQ ID NO:.

Elastic spider silk protein unit repeats include SEQ ID NOs: 25 and 29-35. Hard spider silk protein unit repeats include $(A)_n$; $(GA)_n$; $(GV)_n$; $(AQ)_n$; and $(AY)_n$. Linker unit repeats include SEQ ID NOs: 36-42. Helix spider silk protein unit repeats include $(GGX)_n$, wherein X may be Y, L, Q, V, A, or S. Unit repeats may be combined as indicated herein to produce a larger repeat, multimers of which may be assembled to produce a spider silk protein.

General Guidelines:

1) Elastic units or combinations of elastic units (n=2-63) may be combined with any linker and any hard unit and any helix in that order to create a repeat unit for a MaSp2 protein except:

a) The following combinations are excluded:

SEQ ID NO: 29 operably linked to $(A)_n$ operably linked to SEQ ID NO: 36;

SEQ ID NO: 25 operably linked to $(A)_n$ operably linked to SEQ ID NO: 38;

SEQ ID NO: 30 operably linked to $(A)_n$ operably linked to SEQ ID NO: 42;

SEQ ID NO: 31 operably linked to $(A)_n$ operably linked to SEQ ID NO: 37; and

SEQ ID NO: 32 operably linked to $(A)_n$ operably linked to SEQ ID NO: 37.

The above excluded combinations may be used to generate an amino acid sequence consisting essentially of the amino acid sequence of one of the natural spider silk proteins. The number of repeats (N) may range from 4-9, depending on the specific repeat unit, since they vary within the silk protein.

2) Any single hard segment or combination of segments may be combined with any helix segment to create a repeat unit for a MaSp1 protein.

3) Single repeat units or combinations of repeat units may be used to create proteins with molecular weights ranging from 50,000 dal to 500,000.

The composition of six exemplary synthetic spider silk proteins is provided herein below.

1) three copies of SEQ ID NO: 29 with 1 copy of $(A)_n$ (n=8) with SEQ ID NO: 40 to produce a repeat (SEQ ID NO: 43) and 24 copies of repeat SEQ ID NO: 43 to produce a synthetic spider silk protein with a M.W. of approximately 110,000 dal (SEQ ID NO: 49).

2) four copies of SEQ ID NO: 25 with 1 copy of $(GA)_n$ (n=7) with SEQ ID NO: 38 to produce a repeat (SEQ ID NO: 44) and 50 copies of repeat SEQ ID NO: 44 to produce a synthetic spider silk protein with a M.W. of approximately 300,000 dal (SEQ ID NO: 50).

3) 30 copies of SEQ ID NO: 35 with X=S, Y, S, Y, A repeating in that order with five copies of $(GGX)_n$ with X=A with SEQ ID NO: 37 to produce a repeat (SEQ ID NO: 45) and 20 copies of repeat SEQ ID NO: 45 to produce a synthetic spider silk protein with a M.W. of approximately 330,000 dal (SEQ ID NO: 51).

4) 10 copies of SEQ ID NO: 35 with X=alternating S and Y with 1 copy of $(A)_n$ (n=6) with SEQ ID NO: 36 to produce a repeat (SEQ ID NO: 46) and 32 copies of repeat SEQ ID NO: 46 to produce a synthetic spider silk protein with a M.W. of approximately 202,000 dal (SEQ ID NO: 52).

5) six copies of $(GGX)_n$ with X=Y, L, and Q in that order with 1 copy of $(GA)_n$ (n=9) to produce a repeat (SEQ ID NO: 47) and 64 copies of repeat SEQ ID NO: 47 to produce a synthetic spider silk protein with a M.W. of approximately 205,000 dal (SEQ ID NO: 53).

6) six copies of $(GGX)_n$ with X=alternating V and A with 1 copy of $(GV)_n$ with n=7 to produce a repeat (SEQ ID NO: 48) and 48 copies of repeat SEQ ID NO: 48 to produce a synthetic spider silk protein with a M.W. of approximately 154,000 dal (SEQ ID NO: 54).

Synthetic spider silk proteins 1-3 are provided to exemplify MaSp2 analogs. Synthetic spider silk protein 4 illustrates a Flag analog. Examples of MaSp1 analogs are provided in synthetic spider silk proteins 5 and 6. One of skill in the art, given the guidance and examples provided herein, would be able to design and produce a variety of synthetic spider silk proteins.

Plant expression constructs comprising any of the above modified synthetic spider silk proteins may be constructed and used to transform higher plants as described hereinabove. Modified synthetic spider silk proteins may be isolated from plant cell extracts and manipulated as described hereinabove to produce spider silk protein fibers. Plant-expressed spider silk protein fibers may be woven singly or in combination, as proscribed by a particular application. Such fibers have utility in a variety of applications, including, but not limited to, production of fabric, sutures, artificial ligaments and tendons, medical coverings, flexible casts, high-tech clothing, rope, and reinforced plastics.

REFERENCES

1. Austin, S., Bingham, E. T., Mathews, D. E., Shahan, M. N., Will, J. and Burgess, R. R. 1995 Production and field performance of transgenic alfalfa (*Medicago sativa* L.) expressing alpha-amylase and manganese-dependent lignin peroxidase. *Euphytica* 85, 381-393.
2. Bell A L, Peakall D B (1969) Changes in the fine structure during silk protein productions in the ampullate gland of the spider *Araneus sericatus*. *J Cell Biol* 42, 284-295.
3. Brown, D. C. W. and Atanassov, A. 1985. Role of genetic background in somatic embryogenesis in *Medicago*. *Plant Cell Tissue Organ Culture* 4, 111-122.
4. Chang, L. Y., Yang, W. Y., Browning, K. and Roth, D. A. 1999. Specific in vitro phosphorylation of plant eIF2a by eukaryotic eIF2a kinases. *Plant Mol Biol* 41, 363-370.
5. Fischer, E. 1907 About Spider Silk. *Hoppe-Seyler's Z Physiol Chem* 53, 440-450.
6. Gil, J., Esteban, M. and Roth, D. A. 2000. In vivo regulation of protein synthesis by phosphorylation of the a subunit of wheat eukaryotic initiation factor 2. *Biochemistry* 39, 7521-7530.
7. Gil, J., Esteban, M. and Roth, D. A. 2000. In vivo Regulation of the dsRNA-dependent protein kinase PKR by the cellular glycoprotein p67. *Biochemistry* 39, 16016-16025.
8. Gosline, J. M., Denny, M. W. and DeMont, M. E. 1984. Spider silk as rubber. *Nature* 309, 551-552.
9. Gosline, J. M., DeMont, M. E. and Denny, M. W. 1986. The structure and properties of spider silk. *Endeavor* 10, 37-43.
10. Hinman, M. B. and Lewis, R. V. 1992 Isolation of a clone encoding a second dragline silk fibroin. *J Biol Chem* 267, 19320-19324.
11. Horsch, R., Fry, J., Hoffman, N., Eichholtz, D., Rogers, S. and Fraley, R. 1985. A simple and general method for transferring genes into plants. *Science* 227, 1229-1231.
12. Huang, S., Raman, A. S., Ream, J. E., Fujiwara, H., Cerny, R. E. and Brown, S. M. 1998. Overexpression of 20-oxidase confers a gibberellin-overproduction phenotype in *Arabidopsis*. *Pl Physiol* 118, 773-781.
13. Iiazuka, E. 1983. The physico-chemical properties of silk fibers and the fiber spinning process. *Experientia* 39, 449-454.

14. Kovoor, J. 1972. Etude histochimique et cytologique des glandes sericigenes de quelques Argiopidae. *Ann Sci Nat Zool Biol Anim* 14, 1-10.
15. Lucas, F. 1964. Spiders and their silk. *Discovery* 25, 20-6.
16. Micallef, M. C., Austin, S., and Bingham, E. T. 1995. Improvement of transgenic alfalfa by backcrossing. *Dev. Biol.-Plant.* 31, 187-192.
17. Parkhe, A. J., Seeley, S. K., Gardner, K., Thompson L. and Lewis, R. V. 1997. Structural Studies of Spider Silk Proteins in the Fiber. *J of Molecular Recognition* 10, 1-6.
18. Stauffer, S. L., Coguill, S. L., and Lewis, R. V. 1994. Comparison of physical properties of three silks from *Nephila clavipes* and *Araneus gemmoides*. *J. Arachnology* 22, 5-11.
19. Theil, B. L., Kunkel, D. D., and Viney, C. 1994. Physical and chemical microstructure of spider dragline: a study by analytical transmission electron microscopy. *Biopolymers* 34, 1089-1097.
20. Vollrath, F. 1992. Spider webs and silks. *Scientific American* 266, 70-76.
21. Willcox P. J., Gido S. P., Muller, W., and Kaplan D. L. 1996. Evidence for a Cholesteric Liquid Crystalline Phase in Natural Spinning Processes. *Macromolecules* 29, 5109-10.
22. Work R. W. 1977. Dimensions, Birefringence and Force-elongation behavior. *Textile Res J* 47, 650-662.
23. Xu, M., and Lewis, R. V. 1990. Structure of a protein superfiber: Spider dragline silk. *Proc Natl Aca Sci USA* 87, 7120-7124.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

I claim:

1. An isolated nucleic acid encoding an artificial synthetic spider silk protein comprising a plurality of elastic repeats, a plurality of hard repeats, linkers, and optionally helical repeat segments, said nucleic acid encoding linker amino acid sequences selected from the group consisting of SEQ ID NOS: 39 or 41.

2. The nucleic acid of claim 1 encoding SEQ ID NO: $25_{(x)}$ operably linked via said linker to $A_{(n)}$, wherein x is 2-63 repeats and n is 4-14 repeats.

3. The nucleic acid of claim 1 encoding SEQ ID NO: $29_{(x)}$ operably linked via said linker to $A_{(n)}$, wherein x is 2-63 repeats and n is 4-14 repeats.

4. The nucleic acid of claim 1 encoding SEQ ID NO: $30_{(x)}$ operably linked via said linker to $A_{(n)}$ wherein x is 2-63 repeats and n is 4-14 repeats.

5. The nucleic acid of claim 1 encoding SEQ ID NO: $31_{(x)}$ operably linked via said linker to $A_{(n)}$, wherein x is 2-63 repeats and n is 4-14 repeats.

6. The nucleic acid of claim 1 encoding SEQ ID NO: $32_{(x)}$ operably linked via said linker to $A_{(n)}$, wherein x is 2-63 and n is 4-14.

7. The nucleic acid of claim 1 encoding SEQ ID NO: $33_{(x)}$ operably linked via said linker to $A_{(n)}$, wherein x is 2-63 repeats and n is 4-14 repeats.

8. The nucleic acid of claim 1 encoding SEQ ID NO: $34_{(x)}$ operably linked via said linker to $A_{(n)}$, wherein x is 2-63 repeats and n is 4-14 repeats.

9. The nucleic acid of claim 1 encoding SEQ ID NO: $35_{(x)}$ operably linked via said linker to $A_{(n)}$, wherein x is 2-63 and n is 4-14.

10. A vector comprising the nucleic acid encoding the spider silk protein of claim 1.

11. The vector of claim 10, wherein said vector is selected from the group consisting of pBI121 and pIBT110.

12. A host cell comprising a vector of claim 10.

13. The host cell of claim 12 which is a plant cell.

14. The plant cell of claim 13, wherein said plant is selected from the group consisting of *Arabidopsis*, tobacco, tubers, sunflower, canola, alfalfa, soybean, maize, sorghum, wheat, cotton, small grains, and rice.

15. The host cell of claim 12, selected from the group consisting of a prokaryotic cell and a eukaryotic cell.

16. A synthetic artificial spider silk protein encoded by the isolated nucleic acid of claim 1.

17. A synthetic artificial spider silk protein produced by expression of the vector of claim 10 in a host cell.

* * * * *

SEQUENCE LISTING

```
<160> NUMBER OF SEQ ID NOS: 54

<210> SEQ ID NO 1
<211> LENGTH: 1981
<212> TYPE: DNA
<213> ORGANISM: Nephila clavipes

<400> SEQUENCE: 1
cctggaggat atggaccagg acaacaaggc ccaggaggat atggccctgg acaacaagga      60
ccatctggac ctggcagtgc cgctgcagca gcagcagccg ccgcagcagg acctggagga     120
tatggccctg gacaacaagg acccggagga tatggaccag gacaacaagg acccggaaga     180
tatggaccag gacaacaagg accatctgga cctggcagtg ccgctgcagc cgcagcagga     240
tctggacaac aaggcccagg aggatatgga ccacgtcaac aaggtccagg aggttatgga     300
caaggacaac aaggaccatc tggaccaggc agtgcagccg cagcctcagc cgcagcctca     360
gcagaatctg gacaacaagg cccaggaggt tatggaccag gtcaacaagg cccaggaggt     420
tatggaccag gtcaacaagg tcctggagga tatggaccag gacaacaagg accatctgga     480
ccaggtagtg ccgctgcagc agccgccgcc gcatcaggac ctggacaaca aggaccagga     540
ggatatggac caggtcaaca aggtcctgga ggatatggac caggacaaca aggaccatct     600
ggaccaggta gtgccgctgc agccgccgcc gccgcatcag gacctggaca acaaggacca     660
ggaggatatg gaccaggtca acaaggtcca ggaggttatg gaccaggaca acaaggacta     720
tctggaccag gcagtgcagc tgcagcagcc gcagcaggac tggacaaca aggacccgga     780 ggatatggac caggacaaca aggaccatct ggacccggta gtgccgctgc agcagcagcc     840
gccgcagcag gacctggagg atatggccct ggacaacaag gacccggagg atatggacca     900
ggacaacaag gaccatctgg agcaggcagt gcagcagcag cagccgcagc aggacctgga     960
caacaaggat taggaggtta tggaccagga caacaaggtc caggaggata tggaccagga    1020
caacaaggtc caggaggata tggaccaggt agtgcatctg cagcagcagc cgcagcagga    1080
cctggacaac aaggaccagg aggatatgga cctggacaac aaggaccatc tggaccaggc    1140
agtgcatctg cagcagcagc cgcagccgca gcaggaccag gaggatatgg accaggacaa    1200
caaggtccag gaggatatgc accaggacaa caaggaccat ctggaccagg cagtgcatct    1260
gcagcagcag ccgcagccgc agcaggacca ggaggatatg gaccaggaca acaaggtcca    1320
```

```
ggaggatatg caccaggaca acaaggacca tctggaccag gcagtgcagc agcagcagca    1380
gctgctgcag caggacctgg tggatatgga ccagcgcaac agggaccatc tggtcctgga    1440
atcgcagctt cagctgcttc agcaggacct ggaggttatg gaccagcaca acaaggacca    1500
gctggatatg ggcctggaag cgcagtagca gcctctgccg gtgcaggatc tgcaggttat    1560
gggccaggtt ctcaagcttc cgctgcagct ctcgtctgg cttctccaga ttcaggcgct     1620
agagttgcat cagctgtttc taacttggta tccagtggcc caactagctc tgctgcctta    1680
tcaagtgtta tcagtaacgc tgtgtctcaa attggcgcaa gtaatcctgg tctctctggt    1740
tgcgatgtcc tcattcaagc tctcttggaa atcgtttctg cttgtgtaac catcctttct    1800
tcatccagca ttggtcaagt taattatgga gcggcttctc agttcgccca gttgtcggc    1860 caatctgttt tgagtgcatt ttaattgaaa aatttattaa aatatgcatg gattttctag    1920
cctgggcaac taattgctcg tactatgtaa tttttttta aataaattct ttgcaacttc    1980
t                                                                    1981

<210> SEQ ID NO 2
<211> LENGTH: 111
<212> TYPE: DNA
<213> ORGANISM: Artificial Sequence
<220> FEATURE:
<223> OTHER INFORMATION: synthetic monomeric repeat unit of MaSp2

<400> SEQUENCE: 2
cccgggtggc tatggtcctg dacagcaagg tcctggcggt tacggtcctg gccaacaggg    60
tccctctggt ccaggcagtg cagctgccgc agccgccgca gcgggtccgg a              111

<210> SEQ ID NO 3
<211> LENGTH: 1789
<212> TYPE: DNA
<213> ORGANISM: Artificial Sequence
<220> FEATURE:
<223> OTHER INFORMATION: synthetic spider silk protein (SS1) comprising
      sixteen monomeric repeats of MaSp2

<400> SEQUENCE: 3
gatccccggg gtggctatgg tcctggacag caaggtcctg gcggttacgg tcctggccaa    60
cagggtccct ctggtccagg cagtgcagct gccgcagccg ccgcagcggg tccgggtggc   120
tatggtcctg dacagcaagg tcctggcggt tacggtcctg gccaacaggg tccctctggt   180
ccaggcagtg cagctgccgc agccgccgca gcgggtccgg gtggctatgg tcctggacag   240
caaggtcctg gcggttacgg tcctggccaa cagggtccct ctggtccagg cagtgcagct   300
gccgcagccg ccgcagcggg tccgggtgg ctatggtcct ggacagcaag gtcctggcgg    360
ttacggtcct ggccaacagg gtccctctgg tccaggcagt gcagctgccg cagccgccgc   420
agcgggtccg gacccgggtg ctatggtcc tggacagcaa ggtcctggcg gttacggtcc    480
tggccaacag ggtccctctg gtccaggcag tgcagctgcc gcagccgccg cagcgggtcc   540
ggacccgggt ggctatggtc ctggacagca aggtcctggc ggttacggtc tggccaaca    600 gggtccctct ggtccaggca gtgcagctgc cgcagccgcc gcagcgggtc cggacccggg   660
tggctatggt cctggacagc aaggtcctgg cggttacggt cctggccaac agggtccctc   720
tggtccaggc agtgcagctg ccgcagccgc cgcagcgggt ccgacccgg gtggctatgg    780 tcctggacag caaggtcctg gcggttacgg tcctggccaa cagggtccct ctggtccagg   840
cagtgcagct gccgcagccg ccgcagcggg tccgacccg gtggctatg gtcctggaca    900
```

```
gcaaggtcct ggcggttacg gtcctggcca acagggtccc tctggtccag gcagtgcagc    960
tgccgcagcc gccgcagcgg gtccggaccc gggtggctat ggtcctggac agcaaggtcc   1020
tggcggttac ggtcctggcc aacagggtcc ctctggtcca ggcagtgcag ctgccgcagc   1080
cgccgcagcg ggtccggacc cgggtggcta tggtcctgga cagcaaggtc ctggcggtta   1140
cggtcctggc caacagggtc cctctggtcc aggcagtgca gctgccgcag ccgccgcagc   1200
gggtccggac ccgggtggct atggtcctgg acagcaaggt cctggcggtt acggtcctgg   1260
ccaacagggt ccctctggtc caggcagtgc agctgccgca gccgccgcag cgggtccgga   1320
cccgggtggc tatggtcctg acagcaagg tcctggcggt tacggtcctg gccaacaggg   1380
tccctctggt ccaggcagtg cagctgccgc agccgccgca gcgggtccgg acccgggtgg   1440
ctatggtcct ggacagcaag gtcctggcgg ttacggtcct ggccaacagg gtccctctgg   1500
tccaggcagt gcagctgccg cagccgccgc agcgggtccg gacccgggtg gctatggtcc   1560
tggacagcaa ggtcctggcg gttacggtcc tggccaacag ggtccctctg gtccaggcag   1620
tgcagctgcc gcagccgccg cagcgggtcc ggaccgggtg gctatggtcc tggacagcaa   1680
ggtcctggcg gttacggtcc tggccaacag ggtccctctg gtccaggcag tgcagctgcc   1740
gcagccgccg cagcgggtcc ggatcaagct tatcgatacc gtcgggatc                1789

<210> SEQ ID NO 4
<211> LENGTH: 709
<212> TYPE: DNA
<213> ORGANISM: Argiope trifasciata

<400> SEQUENCE: 4
ggcatcaatg tagatagcgg cagtgtacaa agtgacatta gttccagtag cagcttcctc     60
tcaacaagct cgtcttcggc cagttactct caggcatcag cttcttcgag cagcggtgcc    120
ggatacacag gaccttctgg accttccact ggaccgtctg gctaccctgg gcctttgagt    180
ggcggagcgt cgttcggctc tggccaatct tctttcggtc aaacttcagc cttttccgca    240
tctggtgctg acaatcggc tggagtatct gttatatctt ctcttaattc acccgttgga    300
ttgaggtctc cttctgctgc ttctagactt agtcaattaa catcatccat aacgaatgca    360
gttggtgcca atggtgttga tgctaattct cttgcccgta gtcttcaatc tagtttctcg    420
gcactcagaa gctccggcat gtcttcaagc gatgctaaaa ttgaagtatt gttggaaacc    480
attgttggtc tgcttcagct tttgagcaac actcaagtcc gaggagtaaa cccggcaacg    540
gcttcttcag tagcaaattc tgctgcgaga tcttttgaat tagttttggc ttaagagata    600
ttgattgtta gacctggaga taatgtaac ttttctgata tgcaatttgc atacgaaatt    660
tcttattaaa taaaagcatt ttgaaacatt aaaaaaaaaa aaaaaaaa                 709

<210> SEQ ID NO 5
<211> LENGTH: 1711
<212> TYPE: DNA
<213> ORGANISM: Phidippus audax
<220> FEATURE:
<221> NAME/KEY: misc_feature
<222> LOCATION: (1066)
<223> OTHER INFORMATION: s = c or g
<220> FEATURE:
<221> NAME/KEY: misc_feature
<222> LOCATION: (1078)
<223> OTHER INFORMATION: r = a or g
<220> FEATURE:
<221> NAME/KEY: misc_feature
<222> LOCATION: (1681)
```

<223> OTHER INFORMATION: n = a, c, g, or t

<400> SEQUENCE: 5

| | | | | | |
|---|---|---|---|---|---:|
| ggagctggag | ctggcgctgg | ctatggtgca | ggtgctggtt | caggagctgg | tgcaggctct | 60 |
| ggtgcaggag | ctggagcagg | agctggagca | ggagctggag | caggctatgg | agcaggagca | 120 |
| ggttcaggag | ctggtgctgg | cgcaggttac | ggacgaggtg | caggagcagg | agcgggagct | 180 |
| ggagcaggtt | acggccaagg | tgctggagcg | ggagctggtc | ccggcgcagg | ctatggcgct | 240 |
| ggagctggat | ctggagctgg | agccggctat | ggtacaggtg | ctggttcagg | agctggttca | 300 |
| ggagctggtt | caggagctgg | atcaggagct | ggagcaggag | ctggagcagg | tgcaggttat | 360 |
| ggagcaggag | caggttcagg | agctggtgct | ggcgcaggct | acggacgagg | tgcaggagca | 420 |
| ggagcgggag | ctggagcagg | ttacggccaa | ggtgctggag | caggagctgg | tgccggtgca | 480 |
| ggtgctggtt | caggagctgg | tgcaggttct | ggtgcaggag | ctggtgctgg | tgcaggttac | 540 |
| ggacaaggtg | caggagcagg | agctggtgcc | ggtgcagggt | atggcgctgg | agcaggttct | 600 |
| ggagctggag | ctggcgctgg | ctacggtgca | ggtgctggtt | caggagctgg | tgcaggttct | 660 |
| ggtgcaggag | ctggtgctgg | agcaggttac | ggtcaaggtg | ctggagctgg | agctggcgcc | 720 |
| ggctatggtg | caggtgctgg | ttctggagct | ggtgcaggct | ctggtgcagg | agctggatca | 780 |
| ggagctggag | ctggttcagg | ctatggcgca | ggagctggtt | caggagctgg | cgctggcgca | 840 |
| ggttatggac | aaggtgccgg | agcaggtgct | ggtgcaggtg | caggctatgg | tgcaggagca | 900 |
| ggttctggag | ctggaactgg | tgcaggctat | ggtgctggtg | caggtgcagg | atatggtgct | 960 |
| ggtgcaggtg | caggagctgg | ttcaggagca | ggtgccgggg | caggttatgg | tgctggtgct | 1020 |
| ggtgcaggcg | ctggagcagg | ctatggtgct | ggagctggtt | ccggascagg | tgcaggarca | 1080 |
| ggttatggtg | ctggtgcagg | tgcaggttca | ggtgtaggag | caggtgctgg | agctggtgct | 1140 |
| ggagcaggat | atggagctgg | agcaggtgca | ggagcaggct | atggtgctgg | tgcaggtgca | 1200 |
| ggtgctggtg | ctggtgcagg | agcaggatat | ggcgctggag | caggtgcagg | tgcttctgta | 1260 |
| agttccactg | tatctaacac | tgcttccaga | atgtcttcag | agaatacatc | acgtcgtgtt | 1320 |
| tcttcagcca | tttcaagcat | tgtcggctct | ggtggagtta | acatgaattc | tctttcaaac | 1380 |
| gtaatctcta | atgtatcatc | gagcgttgct | gcatctaatc | ctggactgtc | tggatgtgaa | 1440 |
| gttcttgttc | aaaccctgtt | ggaagtagta | tctgcattgg | ttcacatttt | gagctatgca | 1500 |
| agtgtgggta | gtgttgatgc | cagcgctgct | ggtcagtcag | cccagactgt | agctacagcc | 1560 |
| atgagtagtg | taatgggttg | aattactttg | acctttcaat | atttttgaag | actttatgtt | 1620 |
| gttactttt | gaattacgta | atgtctgaaa | ataagataa | ataaatagaa | gtatatatgc | 1680 |
| naaaaaaaa | aaaaaaaaaa | aaaaaaaaaa | a | | | 1711 |

<210> SEQ ID NO 6
<211> LENGTH: 845
<212> TYPE: DNA
<213> ORGANISM: Zorocrates sp.

<400> SEQUENCE: 6

| | | | | | |
|---|---|---|---|---|---:|
| ggtgcagcag | ccgcagcctc | agcagcagca | gcaggcggac | gaggaagcca | aggaggttac | 60 |
| ggagatgacg | gtggtgcagc | agcagcagca | gcagcagcag | cggcggcagc | cgcggcagga | 120 |
| agtggtggaa | ccggaggagg | acaagggggg | cgcggagatg | gaggtgcggc | agcagcagca | 180 |
| gcagcagccg | cagaggccgc | agcaggtgga | aaaggaagac | aaggaagtta | cggagatgac | 240 |
| ggtggtgcag | cagtagcagc | agcagctgca | gcggcagcag | cggcaggaag | aggtggttcc | 300 |

```
ggaagaggac aaggacttcg tagagataaa ggaagttacg gagttgacgg tggtgcagaa    360
gcagcagcat ccgcagcggc cacagcaggc agacaaggaa gacaaggaag ttacggagat    420
gacggtggtg cagcagcagc agcagcagca gcggcttctg cttcacggtt agcctcctct    480
tctgctgttt ctcgagtctc atctgctgtt tctgcgctgt tgtcaaatgg cttttctgat    540
gtaaattccc tctccaacgt gatttctgga ctttctgctt ctgtatcttc ttccacacct    600
gagctgactg gttgcgaagt tctcgtggaa gtccttttgg aagtagtatc agctttggtt    660
catattttga actttgctga cattggaaac gttaatatta gtgcttcagg tgattccaca    720
tcccttgtag gccgaactgt tttagaagcc tttggctgaa atattactct attccttttt    780
tttttttgaa tattgtttca gcttttaact gtgacataaa aaatgttata taaggaataa    840
atata                                                                845

<210> SEQ ID NO 7
<211> LENGTH: 2282
<212> TYPE: DNA
<213> ORGANISM: Kukulcania hibernalis

<400> SEQUENCE: 7
gctggttcct caggcgatgg tgcgtcagca gcggcttctg ctgcagctgc tgctggagca     60
ggttctggaa gacgaggacc aggaggcgct agatctcgcg gaggagctgg tgctggtgct    120
ggtgccggat ctggagtagg aggctatggt tctggatcag gtgctggtgc tggcgcgggt    180
gctggggcag gcgcaggtgg tgaaggaggt tttggtgaag ccagggcta tggagcaggt    240 gctggagcag gatatggcgc tggccgtgca ggcggtagag gccgtggtgg acgtggtgga    300
gaagctttct ctgcttcttc agcttctagt gcagttgttt ttgaatcggc aggtgctggt    360
gcaggtgcag gttttggtgt tggagctggt gccggtgctg gagcaggagc aggttttggt    420
tctggagctg gtgcgggatc aggtgctgga gcaggatatg gcgctggccg tgcaggcggt    480
agaggccgtg gtggacgtgg tggagaagct ttctctgctt cttcagcttc tagtgcagtt    540
gtttttgaat cggcaggtcc aggcgaagaa gctggttcct caggcgatgg tgcgtcagca    600
gcggcttctg ctgcagcggc tgctggagca ggttctggaa gacgaggacc aggaggcgct    660
agatctcgcg gaggagctgg tgctggtgct ggtgccggat ccggagtagg aggctatggt    720
tctggatcag gtgctggtgc tggcgcgggt gctggggcag gcgcaggtgg tgaaggaggt    780
tttggtgaag ccagggcta tggagcaggt gctggggcag gctttggctc tggcgcaggt    840
gctggagctg agcaggttc gggtgcaggt gcaggagaag gcgttggttc tggcgcaggt    900
gctggtgcag gtgcaggttt tggtgttgga gctggtgccg tgctggagc aggagcaggt    960 tttggttctg gagctggtgc gggatcaggt gctggagcag gatatggcgc tggccgtgca   1020
ggcggtagag gccgtggtgg acgtggtgga gaagctttct ctgcttcttc agcttctagt   1080
gcagttgttt ttgaatcggc aggtccaggc gaggaagctg ttcctcagg cggtggtgcg   1140 tcagcagcgg cttctgctgc agcggctgct ggagcaggtt ctggaagacg aggaccagga   1200
ggcgctagat ctcgcggagg agctggtgct ggtgctggtc ccggatccgg agtaggaggc   1260
tatggttctg gatcaggtgc tggagctggc gcgggtgctg ggcaggcgc aggtggtgaa   1320 ggaggttttg gtgaaggcca gggctatgga gcaggtgctg ggcaggctt tggctctggc   1380 gcaggtgctg gagctggagc aggttcgggt gcaggtgcag gagaaggcgt tggttctggc   1440
gcaggtgctg gtgcaggtgc aggttttggt gttggagctg gtgccggtgc tggagcagga   1500
```

-continued

```
gcaggttttg gttctggagc tggtgcggga tcaggtgctg gagcaggata tggcgctggc    1560
cgtgcaggcg gtagaggccg tggtggacgt ggtggagaag ctttctctgc ttcttcagct    1620
tctagtgcag ttgttttga atcggcaggt ccaggcgagg aagctggttc ctcaggcggt    1680
ggtgcgtcag cagcggcttc tgctgcagcg gctgctggag caggttctgg aagacgagga    1740
ccaggaggcg ctagatctcg cggaggagct ggtgctggtg ctggtgccgg atccggagta    1800
ggaggctatg gttctggatc aggtgctggt gctggcgcgg gtgctgggc aggcgcaggt    1860 ggtgaaggag gttttggtga aggccagggc tatggagcag gtgctggagc cggagcaggt    1920
gctggggcag gctttggctc tggcgcaggt gctggagctg gagcaggttc gggtgcaggt    1980
gcaggagaag gcgttggttc tggcgcaggt gctggtgcag gtgcaggttt tggtgttgga    2040
gctggtgccg gtgctggagc aggagcaggt tttggttctg gagctggtgc gggatcaggt    2100
gctggagcag gatatggcgc tggccgtgca ggcggtagag gccgtggtgg acgtggtgga    2160
gaagctttct ctgcttcttc agcttctagt gcagttgttt ttgaatcggc aggtccaggc    2220
gaggaagctg gttcctcagg cgatggtgcg tcagcagcgg cttctgctgc agcgtctgct    2280
gg                                                                   2282
```

<210> SEQ ID NO 8
<211> LENGTH: 1199
<212> TYPE: DNA
<213> ORGANISM: Kukulcania

<400> SEQUENCE: 8

```
ggatctggct caggttctgg atctggctca ggttctggtt ctggtacagg ttctggatct     60
ggtgcaggct ctggatcagg ggcaggctct ggatcaggag caggctctgg atcaggagca    120
ggctctggat caggagcagg ctctggtgca ggctcaggtg ctgggtcagg atcaggtaat    180
ggttacggag gaggatttgg aataggttac ggtaaccaac aaggatatgg agcaggtttc    240
ggacaaggat ctggggcagg ttctggatcg ggctcaggtt ctggttctgg tgcaggttct    300
ggatctggct caggttctgg ttctggatct ggcgcaggtt ctggatcagg ctctggatct    360
ggttcaggtg caggttccgg atcaggttct ggatcgggct caggttctgg atcgggctca    420
ggttctggtt ctggtgccag ttctggatct ggcgcaggtt ctggttttgg cccaggttct    480
ggatcaagtt caagcccaag ttctggggca agctcagggg ctggttccag atcaggtaag    540
ggttttggag ggagaggata tggagcaggg ttcggacaag gatctggggc aggttctgga    600
tcggcttcag gttctggttc tggtgcaggt tctggatctg gctcaggttc tggttctgga    660
tctggcgcag gttctggatc aggctctgga tctggttcag gtgcaggttc cggatcaggt    720
tctggatcgg gctcaggttc tggatcgggc tcaggttttg gttctggtgc aggttctgga    780
tctggcgcag gttctggttc tggcgcaggt tctggatcag gttcaggcgc aggttctggt    840
gcaggctcag gtgctggttc aggatcaggt aatggttatg gaggaggata tggaataggt    900
tctagttacc aaggatatgg aacaggtttc gggcaaggag ctggcgcagg ttctggatct    960
ggttcaggtg caggttcggg atcaggttct ggatcgggct caggctctgg atctggctca   1020
ggttctggat ctggctcagg ttctggctct ggtgcaggtt ctggatctgg cgcaggcttt   1080
ggatcaggag caggctctgg tgcaggttcg gtgcaggct caggtgctgg gtcaggatct   1140
ggtaatggtt atggaggagg ttatggaata ggttacggtt accaacaagg atatggagc   1199
```

<210> SEQ ID NO 9
<211> LENGTH: 314

<212> TYPE: DNA
<213> ORGANISM: Kukulcania

<400> SEQUENCE: 9

```
ggagctggtg tcggagttgg tgctagtgtc ggagttggtg ctggtgtcgg agttggtgtt    60
ggtgtcgccg ccggtgctgg tgccgccgcc ggcgctggcg ccggtgctgg ggctggtggc   120
ggtgccggag ctggagctgg tgccggagct ggtgctggtg ctggagctgg tgctggcgct   180
ggtgctggag ctggagtcgg agttggtatc ggaatcggtg ctggagctgg tgctggtgct   240
ggagctggtg ctggagctgg tgctggagct ggtgctggtg ccgaagctgg tgtcggagtt   300
ggtgtcggag ttgg                                                    314
```

<210> SEQ ID NO 10
<211> LENGTH: 1682
<212> TYPE: DNA
<213> ORGANISM: Argiope trifasciata

<400> SEQUENCE: 10

```
atcggatatg gacgtggtgc tggtgcagga gcaggcgctg cagcagcggc tggtgctgga    60
gccggagctg gagcagcagg tggatatggg ggaggatacg gaattggagc tggagccggt   120
gcaagtgccg gagctggtgc cggtggagca ggcggatatg gacgtggtgc tggtgcagga   180
gcaggagctg cagcagcagc tggtgctgga gctggagcag caggtggata tggtggagga   240
tacggaggtg gagctggaga cggtgctgga gcaggagccg gtgctggagc aggagctggt   300
gccggtagtg caggcggata tggacgtggt gcaggtgcag gagcaggcgc tgcagcagcg   360
gctggtgctg gagccggagc tggagcagca ggtggatatg gtggaggata cggaattgga   420
gctggagccg gtgcaagtgc cggagctggt gccggtggag caggcggata tggacgtggt   480
gctggtgcag gagcaggagc aggcgctgca gcagcagctg gtgctggtgc cggagctgga   540
gcagcagggg gatatggtgg aggatacgga gctggagctg gaaccggtgc tggagcagga   600
gctggtgccg gtgtagcagg cggatatcga cgtggttctg gtgcaggagc aggcgctgca   660
gcagcggctg gtgctggagc cggagctgga gcagcaggtg gatatggtgg aggatacgga   720
attggagctg gagccggtgc aggttcagga gctggagccg gtgcaggagc aggagctggt   780
gccggtggag caggcggata tggacgtggt gcaggtgcag gagcaggcgc tgcagcagcg   840
gctggtgctg gtgcaggtgc cggtggagca ggcggctatg gacgtggtgc tggtgcagga   900
gcaggcgctg cagctgcggc tggaaccgga gctggagcag caggtggata tggtggagga   960
tacggaggtg gagctggagc gggtgtaggt gcaggagcag gagccggtgg agcaggcgga  1020
tatgacgtg gtgcaggagc aggagcaggc gctgcagcag cggctagtgc tggtgccgga  1080
gcaggaggat atggtggagg atacggagtc gcaggtggaa gtagtatttc atacggcgca  1140
acaagtagtt cagcaacgtc atcgagcaca gcatcttcta gtagatctgg catagttaca  1200
tctggtggat atggagcagg tgctgccgca ggggctggag caggtgccgc tgccggagct  1260
ggttcatata gtggttcgat tagtcgcttg tctagcgctg aagccgtgaa cagagtttct  1320
tctaacatag gagctgtcgc atctggaggt gcatccgccc ttcctggcgt aatttcaaac  1380
attttctctg gagtgagttc ttcggctggc tcctatgaag aagcggttat ccaatctctt  1440
ttggaagttc tttctgttct gcttcatata ttgagcaatt cttccatcgg ctatgttggg  1500
gcggaaggat taggagattc attggcagtt gtacagcaag ccgtaggacc tgttgtcggt  1560
taactcaaat gatgatcttg agccgtgtaa aacataaact taatagttta tcttctgtat  1620
```

-continued

```
tttattgtt atttctaatt aagagaaata aatttcgcat gttttgaaaa aaaaaaaaa      1680 aa                                                                   1682
```

<210> SEQ ID NO 11
<211> LENGTH: 681
<212> TYPE: DNA
<213> ORGANISM: Argiope

<400> SEQUENCE: 11

```
tctggatatg gagctggagc aggtggatct ggtgctggag caggttcagt ggctggatct      60
ggatacggaa gaggatttgc gttagctgcg gcagcaggat ctggtgctgg agcagcgtct     120
cgagctggat atggagctgg agcaggatct ggtgctggag caggttcagg tgcaggagca     180
ggatcaggtt ctgagctgg atatggagta ggagcaggat ctggtgctgg agcaggttca     240
ggtgcaggag ctggatatgg agctggagca ggatctggtg ctggagcagg ttcaggtgct     300
ggagcaggtt caggagctgg atctggatac ggaagaggat ttggagctgg agccggatct     360
ggtgctggag caggttctgg agctggatat ggagctggag caggatctgg tgctggagca     420
ggttcaggtg caggagcagg atcaggttct ggagctggat atggagtagg agcaggatct     480
ggtgctggag caggttcagg tgctggagcc ggatcagggt caggagcagg atacggaaga     540
ggatttggag ctggagccgg atctggtgct ggagcaggtt caggtgtagg agccggatca     600
ggttctggag ctggatatgg aagaagattt ggagctggtg ctggatatgg cgcaggatca     660
ggtgctggag ctggatctgg a                                               681
```

<210> SEQ ID NO 12
<211> LENGTH: 624
<212> TYPE: PRT
<213> ORGANISM: Nephila clavipes

<400> SEQUENCE: 12

```
Pro Gly Gly Tyr Gly Pro Gly Gln Gln Gly Pro Gly Gly Tyr Gly Pro
  1               5                  10                  15

Gly Gln Gln Gly Pro Ser Gly Pro Gly Ser Ala Ala Ala Ala Ala Ala
             20                  25                  30

Ala Ala Ala Ala Gly Pro Gly Gly Tyr Gly Pro Gly Gln Gln Gly Pro
         35                  40                  45

Gly Gly Tyr Gly Pro Gly Gln Gln Pro Gly Arg Tyr Gly Pro Gly
     50                  55                  60

Gln Gln Gly Pro Ser Gly Pro Gly Ser Ala Ala Ala Ala Ala Gly
 65                  70                  75                  80

Ser Gly Gln Gln Gly Pro Gly Gly Tyr Gly Pro Arg Gln Gln Gly Pro
                 85                  90                  95

Gly Gly Tyr Gly Gln Gly Gln Gln Gly Pro Ser Gly Pro Gly Ser Ala
            100                 105                 110

Ala Ala Ser Ala Ala Ala Ser Ala Glu Ser Gly Gln Gln Gly Pro
        115                 120                 125

Gly Gly Tyr Gly Pro Gly Gln Gln Gly Pro Gly Gly Tyr Gly Pro Gly
    130                 135                 140

Gln Gln Gly Pro Gly Gly Tyr Gly Pro Gly Gln Gln Gly Pro Ser Gly
145                 150                 155                 160

Pro Gly Ser Ala Ala Ala Ala Ala Ala Ala Ser Gly Pro Gly Gln
                165                 170                 175

Gln Gly Pro Gly Gly Tyr Gly Pro Gly Gln Gln Gly Pro Gly Gly Tyr
            180                 185                 190
```

```
Gly Pro Gly Gln Gln Gly Pro Ser Gly Pro Gly Ser Ala Ala Ala
            195                 200                 205

Ala Ala Ala Ala Ser Gly Pro Gly Gln Gln Gly Pro Gly Gly Tyr Gly
210                 215                 220

Pro Gly Gln Gln Gly Pro Gly Gly Tyr Gly Pro Gly Gln Gln Gly Leu
225                 230                 235                 240

Ser Gly Pro Gly Ser Ala Ala Ala Ala Ala Ala Gly Pro Gly Gln
            245                 250                 255

Gln Gly Pro Gly Gly Tyr Gly Pro Gln Gln Gly Pro Ser Gly Pro
            260                 265                 270

Gly Ser Ala Ala Ala Ala Ala Ala Ala Gly Pro Gly Gly Tyr
        275                 280                 285

Gly Pro Gly Gln Gln Gly Pro Gly Gly Tyr Gly Pro Gly Gln Gln Gly
            290                 295                 300

Pro Ser Gly Ala Gly Ser Ala Ala Ala Ala Ala Ala Gly Pro Gly
305                 310                 315                 320

Gln Gln Gly Leu Gly Gly Tyr Gly Pro Gly Gln Gln Gly Pro Gly Gly
                325                 330                 335

Tyr Gly Pro Gly Gln Gln Gly Pro Gly Gly Tyr Gly Pro Gly Ser Ala
            340                 345                 350

Ser Ala Ala Ala Ala Ala Ala Gly Pro Gly Gln Gln Gly Pro Gly Gly
        355                 360                 365

Tyr Gly Pro Gly Gln Gln Gly Pro Ser Gly Pro Gly Ser Ala Ser Ala
            370                 375                 380

Ala Ala Ala Ala Ala Ala Gly Pro Gly Gly Tyr Gly Pro Gly Gln
385                 390                 395                 400

Gln Gly Pro Gly Gly Tyr Ala Pro Gly Gln Gln Gly Pro Ser Gly Pro
                405                 410                 415

Gly Ser Ala Ser Ala Ala Ala Ala Ala Ala Gly Pro Gly Gly
            420                 425                 430

Tyr Gly Pro Gly Gln Gln Gly Pro Gly Gly Tyr Ala Pro Gly Gln Gln
            435                 440                 445

Gly Pro Ser Gly Pro Gly Ser Ala Ala Ala Ala Ala Ala Ala Ala
450                 455                 460

Gly Pro Gly Gly Tyr Gly Pro Ala Gln Gln Gly Pro Ser Gly Pro Gly
465                 470                 475                 480

Ile Ala Ala Ser Ala Ala Ser Ala Gly Pro Gly Gly Tyr Gly Pro Ala
                485                 490                 495

Gln Gln Gly Pro Ala Gly Tyr Gly Pro Gly Ser Ala Val Ala Ala Ser
            500                 505                 510

Ala Gly Ala Gly Ser Ala Gly Tyr Gly Pro Gly Ser Gln Ala Ser Ala
        515                 520                 525

Ala Ala Ser Arg Leu Ala Ser Pro Asp Ser Gly Ala Arg Val Ala Ser
        530                 535                 540

Ala Val Ser Asn Leu Val Ser Ser Gly Pro Thr Ser Ser Ala Ala Leu
545                 550                 555                 560

Ser Ser Val Ile Ser Asn Ala Val Ser Gln Ile Gly Ala Ser Asn Pro
            565                 570                 575

Gly Leu Ser Gly Cys Asp Val Leu Ile Gln Ala Leu Leu Glu Ile Val
            580                 585                 590

Ser Ala Cys Val Thr Ile Leu Ser Ser Ser Ser Ile Gly Gln Val Asn
            595                 600                 605
```

Tyr Gly Ala Ala Ser Gln Phe Ala Gln Val Val Gly Gln Ser Val Leu
        610                 615                 620

<210> SEQ ID NO 13
<211> LENGTH: 35
<212> TYPE: PRT
<213> ORGANISM: Artificial Sequence
<220> FEATURE:
<223> OTHER INFORMATION: synthetic monomeric repeat unit of MaSp2

<400> SEQUENCE: 13

Pro Gly Gly Tyr Gly Pro Gly Gln Gln Gly Pro Gly Gly Tyr Gly Pro
1               5                   10                  15

Gly Gln Gln Gly Pro Ser Gly Pro Gly Ser Ala Ala Ala Ala Ala Ala
            20                  25                  30

Ala Ala Gly
        35

<210> SEQ ID NO 14
<211> LENGTH: 596
<212> TYPE: PRT
<213> ORGANISM: Artificial Sequence
<220> FEATURE:
<223> OTHER INFORMATION: synthetic spider silk protein (SS1) comprising
      sixteen monomeric repeats of MaSp2

<400> SEQUENCE: 14

Asp Pro Pro Gly Gly Tyr Gly Pro Gly Gln Gln Gly Pro Gly Gly Tyr
1               5                   10                  15

Gly Pro Gly Gln Gln Gly Pro Ser Gly Pro Gly Ser Ala Ala Ala Ala
            20                  25                  30

Ala Ala Ala Ala Gly Pro Gly Gly Tyr Gly Pro Gly Gln Gln Gly Pro
        35                  40                  45

Gly Gly Tyr Gly Pro Gly Gln Gln Gly Pro Ser Gly Pro Gly Ser Ala
    50                  55                  60

Ala Ala Ala Ala Ala Ala Gly Pro Gly Gly Tyr Gly Pro Gly Gln Gln
65                  70                  75                  80

Gln Gly Pro Gly Gly Tyr Gly Pro Gly Gln Gln Gly Pro Ser Gly Pro
                85                  90                  95

Gly Ser Ala Ala Ala Ala Ala Ala Ala Gly Pro Gly Trp Leu Trp
            100                 105                 110

Ser Trp Thr Ala Arg Ser Trp Arg Leu Arg Ser Trp Pro Thr Gly Ser
        115                 120                 125

Leu Trp Ser Arg Gln Cys Ser Cys Arg Ser Arg Arg Ser Gly Ser Gly
    130                 135                 140

Pro Gly Trp Leu Trp Ser Trp Thr Ala Arg Ser Trp Arg Leu Arg Ser
145                 150                 155                 160

Trp Pro Thr Gly Ser Leu Trp Ser Arg Gln Cys Ser Cys Arg Ser Arg
                165                 170                 175

Arg Ser Gly Ser Gly Pro Gly Trp Leu Trp Ser Trp Thr Ala Arg Ser
            180                 185                 190

Trp Arg Leu Arg Ser Trp Pro Thr Gly Ser Leu Trp Ser Arg Gln Cys
        195                 200                 205

Ser Cys Arg Ser Arg Arg Ser Gly Ser Gly Pro Gly Trp Leu Trp Ser
    210                 215                 220

Trp Thr Ala Arg Ser Trp Arg Leu Arg Ser Trp Pro Thr Gly Ser Leu
225                 230                 235                 240

Trp Ser Arg Gln Cys Ser Cys Arg Ser Arg Arg Ser Gly Ser Gly Pro

-continued

```
                245                 250                 255
Gly Trp Leu Trp Ser Trp Thr Ala Arg Ser Trp Arg Leu Arg Ser Trp
            260                 265                 270

Pro Thr Gly Ser Leu Trp Ser Arg Gln Cys Ser Cys Arg Ser Arg Arg
        275                 280                 285

Ser Gly Ser Gly Pro Gly Trp Leu Trp Ser Trp Thr Ala Arg Ser Trp
    290                 295                 300

Arg Leu Arg Ser Trp Pro Thr Gly Ser Leu Trp Ser Arg Gln Cys Ser
305                 310                 315                 320

Cys Arg Ser Arg Arg Ser Gly Ser Gly Pro Gly Trp Leu Trp Ser Trp
                325                 330                 335

Thr Ala Arg Ser Trp Arg Leu Arg Ser Trp Pro Thr Gly Ser Leu Trp
            340                 345                 350

Ser Arg Gln Cys Ser Cys Arg Ser Arg Arg Ser Gly Ser Gly Pro Gly
        355                 360                 365

Trp Leu Trp Ser Trp Thr Ala Arg Ser Trp Arg Leu Arg Ser Trp Pro
    370                 375                 380

Thr Gly Ser Leu Trp Ser Arg Gln Cys Ser Cys Arg Ser Arg Arg Ser
385                 390                 395                 400

Gly Ser Gly Pro Gly Trp Leu Trp Ser Trp Thr Ala Arg Ser Trp Arg
                405                 410                 415

Leu Arg Ser Trp Pro Thr Gly Ser Leu Trp Ser Arg Gln Cys Ser Cys
            420                 425                 430

Arg Ser Arg Arg Ser Gly Ser Gly Pro Gly Trp Leu Trp Ser Trp Thr
        435                 440                 445

Ala Arg Ser Trp Arg Leu Arg Ser Trp Pro Thr Gly Ser Leu Trp Ser
    450                 455                 460

Arg Gln Cys Ser Cys Arg Ser Arg Arg Ser Gly Ser Gly Pro Gly Trp
465                 470                 475                 480

Leu Trp Ser Trp Thr Ala Arg Ser Trp Arg Leu Arg Ser Trp Pro Thr
                485                 490                 495

Gly Ser Leu Trp Ser Arg Gln Cys Ser Cys Arg Ser Arg Arg Ser Gly
            500                 505                 510

Ser Gly Pro Gly Trp Leu Trp Ser Trp Thr Ala Arg Ser Trp Arg Leu
        515                 520                 525

Arg Ser Trp Pro Thr Gly Ser Leu Trp Ser Arg Gln Cys Ser Cys Arg
    530                 535                 540

Ser Arg Arg Ser Gly Ser Gly Pro Gly Gly Tyr Gly Pro Gly Gln Gln
545                 550                 555                 560

Gly Pro Gly Gly Tyr Gly Pro Gly Gln Gln Gly Pro Ser Gly Pro Gly
                565                 570                 575

Ser Ala Ala Ala Ala Ala Ala Ala Ala Gly Pro Asp Gln Ala Tyr Arg
            580                 585                 590

Tyr Arg Arg Asp
        595

<210> SEQ ID NO 15
<211> LENGTH: 197
<212> TYPE: PRT
<213> ORGANISM: Argiope trifasciata

<400> SEQUENCE: 15

Gly Ile Asn Val Asp Ser Gly Ser Val Gln Ser Asp Ile Ser Ser Ser
 1               5                  10                  15
```

```
Ser Ser Phe Leu Ser Thr Ser Ser Ser Ala Ser Tyr Ser Gln Ala
                20                  25                  30

Ser Ala Ser Ser Ser Gly Ala Gly Tyr Thr Gly Pro Ser Gly Pro
        35                  40                  45

Ser Thr Gly Pro Ser Gly Tyr Pro Gly Pro Leu Ser Gly Ala Ser
50                  55                  60

Phe Gly Ser Gly Gln Ser Ser Phe Gly Gln Thr Ser Ala Phe Ser Ala
65                  70                  75                  80

Ser Gly Ala Gly Gln Ser Ala Gly Val Ser Val Ile Ser Ser Leu Asn
                85                  90                  95

Ser Pro Val Gly Leu Arg Ser Pro Ser Ala Ala Ser Arg Leu Ser Gln
                100                 105                 110

Leu Thr Ser Ser Ile Thr Asn Ala Val Gly Ala Asn Gly Val Asp Ala
                115                 120                 125

Asn Ser Leu Ala Arg Ser Leu Gln Ser Ser Phe Ser Ala Leu Arg Ser
130                 135                 140

Ser Gly Met Ser Ser Ser Asp Ala Lys Ile Glu Val Leu Leu Glu Thr
145                 150                 155                 160

Ile Val Gly Leu Leu Gln Leu Leu Ser Asn Thr Gln Val Arg Gly Val
                165                 170                 175

Asn Pro Ala Thr Ala Ser Ser Val Ala Asn Ser Ala Ala Arg Ser Phe
                180                 185                 190

Glu Leu Val Leu Ala
            195

<210> SEQ ID NO 16
<211> LENGTH: 525
<212> TYPE: PRT
<213> ORGANISM: Phidippus audax
<220> FEATURE:
<221> NAME/KEY: misc_feature
<222> LOCATION: (0)...(0)
<223> OTHER INFORMATION: Xaa = any amino acid

<400> SEQUENCE: 16

Ala Gly Ala Gly Ala Gly Tyr Gly Ala Gly Ala Gly Ser Gly Ala Gly
1               5                   10                  15

Ala Gly Ser Gly Ala Gly Ala Gly Ala Gly Ala Gly Ala Gly Ala Gly
                20                  25                  30

Ala Gly Tyr Gly Ala Gly Ala Gly Ser Gly Ala Gly Ala Gly Ala Gly
                35                  40                  45

Tyr Gly Arg Gly Ala Gly Ala Gly Ala Gly Ala Gly Ala Gly Tyr Gly
        50                  55                  60

Gln Gly Ala Gly Ala Gly Ala Gly Ala Gly Ala Gly Tyr Gly Ala Gly
65                  70                  75                  80

Ala Gly Ser Gly Ala Gly Ala Gly Tyr Gly Thr Gly Ala Gly Ser Gly
                85                  90                  95

Ala Gly Ser Gly Ala Gly Ser Gly Ala Gly Ser Gly Ala Gly Ala Gly
                100                 105                 110

Ala Gly Ala Gly Ala Gly Tyr Gly Ala Gly Ala Gly Ser Gly Ala Gly
                115                 120                 125

Ala Gly Ala Gly Tyr Gly Arg Gly Ala Gly Ala Gly Ala Gly Ala Gly
                130                 135                 140

Ala Gly Tyr Gly Gln Gly Ala Gly Ala Gly Ala Gly Ala Gly Ala Gly
145                 150                 155                 160

Ala Gly Ser Gly Ala Gly Ala Gly Ser Gly Ala Gly Ala Gly Ala Gly
```

```
                165                 170                 175
Ala Gly Tyr Gly Gln Gly Ala Gly Ala Gly Ala Gly Ala Gly
            180                 185                 190
Tyr Gly Ala Gly Ala Gly Ser Gly Ala Gly Ala Gly Ala Gly Tyr Gly
            195                 200                 205
Ala Gly Ala Gly Ser Gly Ala Gly Ala Gly Ser Gly Ala Gly
        210                 215                 220
Ala Gly Ala Gly Tyr Gly Gln Gly Ala Gly Ala Gly Ala Gly
225                 230                 235                 240
Tyr Gly Ala Gly Ala Gly Ser Gly Ala Gly Ala Gly Ser Gly Ala Gly
            245                 250                 255
Ala Gly Ser Gly Ala Gly Ala Gly Ser Gly Tyr Gly Ala Gly Ala Gly
            260                 265                 270
Ser Gly Ala Gly Ala Gly Ala Gly Tyr Gly Gln Gly Ala Gly Ala Gly
        275                 280                 285
Ala Gly Ala Gly Ala Gly Tyr Gly Ala Gly Ala Gly Ser Gly Ala Gly
        290                 295                 300
Thr Gly Ala Gly Tyr Gly Ala Gly Ala Gly Ala Gly Tyr Gly Ala Gly
305                 310                 315                 320
Ala Gly Ala Gly Ala Gly Ser Gly Ala Gly Ala Gly Ala Gly Tyr Gly
            325                 330                 335
Ala Gly Ala Gly Ala Gly Ala Gly Ala Gly Tyr Gly Ala Gly Ala Gly
        340                 345                 350
Ser Gly Xaa Gly Ala Gly Xaa Gly Tyr Gly Ala Gly Ala Gly Ala Gly
            355                 360                 365
Ser Gly Val Gly Ala Gly Ala Gly Ala Gly Ala Gly Tyr Gly
        370                 375                 380
Ala Gly Ala Gly Ala Gly Ala Gly Tyr Gly Ala Gly Ala Gly Ala Gly
385                 390                 395                 400
Ala Gly Ala Gly Ala Gly Ala Gly Tyr Gly Ala Gly Ala Gly Ala Gly
            405                 410                 415
Ala Ser Val Ser Ser Thr Val Ser Asn Thr Ala Ser Arg Met Ser Ser
            420                 425                 430
Glu Asn Thr Ser Arg Arg Val Ser Ser Ala Ile Ser Ser Ile Val Gly
            435                 440                 445
Ser Gly Gly Val Asn Met Asn Ser Leu Ser Asn Val Ile Ser Asn Val
        450                 455                 460
Ser Ser Ser Val Ala Ala Ser Asn Pro Gly Leu Ser Gly Cys Glu Val
465                 470                 475                 480
Leu Val Gln Thr Leu Leu Glu Val Val Ser Ala Leu Val His Ile Leu
            485                 490                 495
Ser Tyr Ala Ser Val Gly Ser Val Asp Ala Ser Ala Ala Gly Gln Ser
            500                 505                 510
Ala Gln Thr Val Ala Thr Ala Met Ser Ser Val Met Gly
        515                 520                 525

<210> SEQ ID NO 17
<211> LENGTH: 252
<212> TYPE: PRT
<213> ORGANISM: Zorocrates sp.

<400> SEQUENCE: 17

Gly Ala Ala Ala Ala Ser Ala Ala Ala Gly Gly Arg Gly Ser
1               5                   10                  15
```

```
Gln Gly Gly Tyr Gly Asp Asp Gly Gly Ala Ala Ala Ala Ala Ala
                20                  25                  30

Ala Ala Ala Ala Ala Ala Gly Ser Gly Gly Thr Gly Gly Gly Gln
            35                  40                  45

Gly Gly Arg Gly Asp Gly Ala Ala Ala Ala Ala Ala Ala Ala Ala
50                  55                  60

Glu Ala Ala Gly Gly Lys Gly Arg Gln Gly Ser Tyr Gly Asp Asp
65                  70                  75                  80

Gly Gly Ala Ala Val Ala Ala Ala Ala Ala Ala Ala Ala Ala Gly
                85                  90                  95

Arg Gly Gly Ser Gly Arg Gly Gln Gly Leu Arg Arg Asp Lys Gly Ser
                100                 105                 110

Tyr Gly Val Asp Gly Gly Ala Glu Ala Ala Ser Ala Ala Ala Thr
            115                 120                 125

Ala Gly Arg Gln Gly Arg Gln Gly Ser Tyr Gly Asp Asp Gly Gly Ala
        130                 135                 140

Ala Ala Ala Ala Ala Ala Ala Ser Ala Ser Arg Leu Ala Ser Ser
145                 150                 155                 160

Ser Ala Val Ser Arg Val Ser Ser Ala Val Ser Ala Leu Leu Ser Asn
                165                 170                 175

Gly Phe Ser Asp Val Asn Ser Leu Ser Asn Val Ile Ser Gly Leu Ser
            180                 185                 190

Ala Ser Val Ser Ser Ser Thr Pro Glu Leu Thr Gly Cys Glu Val Leu
        195                 200                 205

Val Glu Val Leu Leu Glu Val Val Ser Ala Leu Val His Ile Leu Asn
210                 215                 220

Phe Ala Asp Ile Gly Asn Val Asn Ile Ser Ala Ser Gly Asp Ser Thr
225                 230                 235                 240

Ser Leu Val Gly Arg Thr Val Leu Glu Ala Phe Gly
                245                 250

<210> SEQ ID NO 18
<211> LENGTH: 761
<212> TYPE: PRT
<213> ORGANISM: Kukulcania hibernalis

<400> SEQUENCE: 18

Ala Gly Ser Ser Gly Asp Gly Ala Ser Ala Ala Ser Ala Ala Ala
1               5                   10                  15

Ala Ala Gly Ala Gly Ser Gly Arg Arg Gly Pro Gly Gly Ala Arg Ser
            20                  25                  30

Arg Gly Gly Ala Gly Ala Gly Ala Gly Ala Gly Ser Gly Val Gly Gly
        35                  40                  45

Tyr Gly Ser Gly Ser Gly Ala Gly Ala Gly Ala Gly Ala Gly Ala Gly
    50                  55                  60

Ala Gly Gly Glu Gly Gly Phe Gly Glu Gly Gln Gly Tyr Gly Ala Gly
65                  70                  75                  80

Ala Gly Ala Gly Tyr Gly Ala Gly Arg Ala Gly Arg Gly Arg Gly
                85                  90                  95

Gly Arg Gly Gly Glu Ala Phe Ser Ala Ser Ser Ala Ser Ser Ala Val
            100                 105                 110

Val Phe Glu Ser Ala Gly Ala Gly Ala Gly Ala Gly Phe Gly Val Gly
        115                 120                 125

Ala Gly Ala Gly Ala Gly Ala Gly Ala Gly Phe Gly Ser Gly Ala Gly
    130                 135                 140
```

```
Ala Gly Ser Gly Ala Gly Ala Gly Tyr Gly Ala Gly Arg Ala Gly Gly
145                 150                 155                 160

Arg Gly Arg Gly Gly Arg Gly Glu Ala Phe Ser Ala Ser Ser Ala
            165                 170                 175

Ser Ser Ala Val Val Phe Glu Ser Ala Gly Pro Gly Glu Glu Ala Gly
                180                 185                 190

Ser Ser Gly Asp Gly Ala Ser Ala Ala Ser Ala Ala Ala Ala
            195                 200                 205

Gly Ala Gly Ser Gly Arg Arg Gly Pro Gly Gly Ala Arg Ser Arg Gly
210                 215                 220

Gly Ala Gly Ala Gly Ala Gly Ala Gly Ser Gly Val Gly Gly Tyr Gly
225                 230                 235                 240

Ser Gly Ser Gly Ala Gly Ala Gly Ala Gly Ala Gly Ala Gly
                245                 250                 255

Gly Glu Gly Gly Phe Gly Glu Gly Gln Gly Tyr Gly Ala Gly Ala Gly
            260                 265                 270

Ala Gly Phe Gly Ser Gly Ala Gly Ala Gly Ala Gly Ala Gly Ser Gly
            275                 280                 285

Ala Gly Ala Gly Glu Gly Val Gly Ser Gly Ala Gly Ala Gly Ala Gly
            290                 295                 300

Ala Gly Phe Gly Val Gly Ala Gly Ala Gly Ala Gly Ala Gly Ala Gly
305                 310                 315                 320

Phe Gly Ser Gly Ala Gly Ala Gly Ser Gly Ala Gly Ala Gly Tyr Gly
                325                 330                 335

Ala Gly Arg Ala Gly Gly Arg Gly Arg Gly Gly Arg Gly Gly Glu Ala
            340                 345                 350

Phe Ser Ala Ser Ser Ala Ser Ser Ala Val Val Phe Glu Ser Ala Gly
            355                 360                 365

Pro Gly Glu Glu Ala Gly Ser Ser Gly Gly Ala Ser Ala Ala Ala
370                 375                 380

Ser Ala Ala Ala Ala Gly Ala Gly Ser Gly Arg Arg Gly Pro Gly
385                 390                 395                 400

Gly Ala Arg Ser Arg Gly Gly Ala Gly Ala Gly Ala Gly Ala Gly Ser
                405                 410                 415

Gly Val Gly Gly Tyr Gly Ser Gly Ser Gly Ala Gly Ala Gly Ala Gly
            420                 425                 430

Ala Gly Ala Gly Ala Gly Glu Gly Gly Phe Gly Glu Gly Gln Gly
            435                 440                 445

Tyr Gly Ala Gly Ala Gly Ala Gly Phe Gly Ser Gly Ala Gly Ala Gly
            450                 455                 460

Ala Gly Ala Gly Ser Gly Ala Gly Ala Gly Glu Gly Val Gly Ser Gly
465                 470                 475                 480

Ala Gly Ala Gly Ala Gly Ala Gly Phe Gly Val Gly Ala Gly Ala Gly
            485                 490                 495

Ala Gly Ala Gly Ala Gly Phe Gly Ser Gly Ala Gly Ala Gly Ser Gly
            500                 505                 510

Ala Gly Ala Gly Tyr Gly Ala Gly Arg Ala Gly Gly Arg Gly Arg Gly
            515                 520                 525

Gly Arg Gly Gly Glu Ala Phe Ser Ala Ser Ser Ala Ser Ser Ala Val
            530                 535                 540

Val Phe Glu Ser Ala Gly Pro Gly Glu Glu Ala Gly Ser Ser Gly Gly
545                 550                 555                 560
```

-continued

```
Gly Ala Ser Ala Ala Ser Ala Ala Ala Ala Gly Ala Gly Ser
            565                 570                 575

Gly Arg Arg Gly Pro Gly Gly Ala Arg Ser Arg Gly Gly Ala Gly Ala
            580                 585                 590

Gly Ala Gly Ala Gly Ser Gly Val Gly Tyr Gly Ser Gly Ser Gly
            595                 600                 605

Ala Gly Ala Gly Ala Gly Ala Gly Ala Gly Gly Glu Gly Gly
            610                 615                 620

Phe Gly Glu Gly Gln Gly Tyr Gly Ala Gly Ala Gly Ala Gly
625                 630                 635                 640

Ala Gly Ala Gly Phe Gly Ser Gly Ala Gly Ala Gly Ala Ala Gly
            645                 650                 655

Ser Gly Ala Gly Ala Gly Glu Gly Val Gly Ser Gly Ala Gly Ala Gly
            660                 665                 670

Ala Gly Ala Gly Phe Gly Val Gly Ala Gly Ala Gly Ala Gly Ala Gly
            675                 680                 685

Ala Gly Phe Gly Ser Gly Ala Gly Ala Gly Ser Gly Ala Gly Ala Gly
            690                 695                 700

Tyr Gly Ala Gly Arg Ala Gly Gly Arg Gly Arg Gly Gly Arg Gly Gly
705                 710                 715                 720

Glu Ala Phe Ser Ala Ser Ser Ala Ser Ser Ala Val Val Phe Glu Ser
            725                 730                 735

Ala Gly Pro Gly Glu Glu Ala Gly Ser Ser Gly Asp Gly Ala Ser Ala
            740                 745                 750

Ala Ala Ser Ala Ala Ala Ser Ala Gly
            755                 760

<210> SEQ ID NO 19
<211> LENGTH: 384
<212> TYPE: PRT
<213> ORGANISM: Kukulcania

<400> SEQUENCE: 19

Gly Ser Gly Ser Gly Ser Gly Ser Gly Ser Gly Ser Gly Ser Gly Thr
1               5                   10                  15

Gly Ser Gly Ser Gly Ala Gly Ser Gly Ser Gly Ala Gly Ser Gly Ser
            20                  25                  30

Gly Ala Gly Ser Gly Ser Gly Ala Gly Ser Gly Ser Gly Ala Gly Ser
            35                  40                  45

Gly Ala Gly Ser Gly Ala Gly Ser Gly Ser Gly Asn Gly Tyr Gly Gly
            50                  55                  60

Gly Phe Gly Ile Gly Tyr Gly Asn Gln Gln Gly Tyr Gly Ala Gly Phe
65              70                  75                  80

Gly Gln Gly Ser Gly Ala Gly Ser Gly Ser Gly Ser Gly Ser Gly Ser
            85                  90                  95

Gly Ala Gly Ser Gly Ser Gly Ser Gly Ser Gly Ser Gly Ser Gly Ala
            100                 105                 110

Gly Ser Gly Ser Gly Ser Gly Ser Gly Ser Gly Ala Gly Ser Gly Ser
            115                 120                 125

Gly Ser Gly Ser Gly Ser Gly Ser Gly Ser Gly Ser Gly Ser Gly Ser
            130                 135                 140

Gly Ala Ser Ser Gly Ser Gly Ala Gly Ser Gly Phe Gly Pro Gly Ser
145                 150                 155                 160

Gly Ser Ser Ser Ser Pro Ser Ser Gly Ala Ser Ser Gly Ala Gly Ser
            165                 170                 175
```

-continued

```
Arg Ser Gly Lys Gly Phe Gly Gly Arg Gly Tyr Gly Ala Gly Phe Gly
            180                 185                 190

Gln Gly Ser Gly Ala Gly Ser Gly Ser Ala Ser Gly Ser Gly Ser Gly
            195                 200                 205

Ala Gly Ser Gly Ser Gly Ser Gly Ser Gly Ser Gly Ser Gly Ala Gly
            210                 215                 220

Ser Gly Ser Gly Ser Gly Ser Gly Ser Gly Ala Gly Ser Gly Ser Gly
225                 230                 235                 240

Ser Gly Ser Gly Ser Gly Ser Gly Ser Gly Phe Gly Ser Gly
            245                 250                 255

Ala Gly Ser Gly Ser Gly Ala Gly Ser Gly Ser Gly Ala Gly Ser Gly
            260                 265                 270

Ser Gly Asn Gly Tyr Gly Gly Tyr Gly Ile Gly Ser Ser Tyr Gln
            275                 280                 285

Gly Tyr Gly Thr Gly Phe Gly Gln Gly Ala Gly Ala Gly Ser Gly Ser
            290                 295                 300

Gly Ser Gly Ala Gly Ser Gly Ser Gly Ser Gly Ser Gly Ser Gly Ser
305                 310                 315                 320

Gly Ser Gly Ser Gly Ser Gly Ser Gly Ser Gly Ser Gly Ser Gly Ala
            325                 330                 335

Gly Ser Gly Ser Gly Ala Gly Phe Gly Ser Gly Ala Gly Ser Gly Ala
            340                 345                 350

Gly Ser Gly Ala Gly Ser Gly Ala Gly Ser Gly Ser Gly Asn Gly Tyr
            355                 360                 365

Gly Gly Gly Tyr Gly Ile Gly Tyr Gly Gln Gln Gly Tyr Gly Ala
            370                 375                 380

<210> SEQ ID NO 20
<211> LENGTH: 105
<212> TYPE: PRT
<213> ORGANISM: Kukulcania

<400> SEQUENCE: 20

Gly Ala Gly Val Gly Val Gly Ala Ser Val Gly Val Gly Ala Gly Val
1               5                   10                  15

Gly Val Gly Val Gly Val Ala Gly Ala Gly Ala Ala Ala Gly Ala
            20                  25                  30

Gly Ala Gly Ala Gly Ala Gly Gly Ala Gly Ala Gly Ala Gly Ala
        35                  40                  45

Gly Ala Gly Ala Gly Ala Gly Ala Gly Ala Gly Ala Gly Ala Gly Ala
    50                  55                  60

Gly Val Gly Val Gly Ile Gly Ile Gly Ala Gly Ala Gly Ala Gly Ala
65                  70                  75                  80

Gly Ala Gly Ala Gly Ala Gly Ala Gly Ala Gly Ala Gly Ala Glu Ala
            85                  90                  95

Gly Val Gly Val Gly Val Gly Val Gly
            100                 105

<210> SEQ ID NO 21
<211> LENGTH: 520
<212> TYPE: PRT
<213> ORGANISM: Argiope trifasciata

<400> SEQUENCE: 21

Ile Gly Tyr Gly Arg Gly Ala Gly Ala Gly Ala Gly Ala Ala Ala Ala
1               5                   10                  15
```

-continued

```
Ala Gly Ala Gly Ala Gly Ala Gly Ala Ala Gly Gly Tyr Gly Gly Gly
             20                  25                  30

Tyr Gly Ile Gly Ala Gly Ala Gly Ala Ser Ala Gly Ala Gly Ala Gly
             35                  40                  45

Gly Ala Gly Gly Tyr Gly Arg Gly Ala Gly Ala Gly Ala Gly Ala Ala
 50                  55                  60

Ala Ala Ala Gly Ala Gly Ala Gly Ala Ala Gly Gly Tyr Gly Gly Gly
 65                  70                  75                  80

Tyr Gly Gly Ala Gly Asp Gly Ala Gly Gly Ala Gly Ala Gly
             85                  90                  95

Ala Gly Ala Gly Ala Gly Ser Ala Gly Gly Tyr Gly Arg Gly Ala Gly
             100                 105                 110

Ala Gly Ala Gly Ala Ala Ala Ala Ala Gly Ala Gly Ala Gly Ala Gly
             115                 120                 125

Ala Gly Gly Gly Tyr Gly Gly Tyr Gly Ile Gly Ala Gly Ala Gly
             130                 135                 140

Ala Ser Ala Gly Ala Gly Ala Gly Gly Ala Gly Gly Tyr Gly Arg Gly
145                 150                 155                 160

Ala Gly Ala Gly Ala Gly Ala Gly Ala Ala Ala Ala Ala Gly Ala Gly
             165                 170                 175

Ala Gly Ala Gly Ala Ala Gly Gly Tyr Gly Gly Gly Tyr Gly Ala Gly
             180                 185                 190

Ala Gly Thr Gly Ala Gly Ala Gly Ala Gly Ala Gly Val Ala Gly Gly
             195                 200                 205

Tyr Arg Arg Gly Ser Gly Ala Gly Ala Gly Ala Ala Ala Ala Ala Gly
210                 215                 220

Ala Gly Ala Gly Ala Gly Ala Ala Gly Gly Tyr Gly Gly Gly Tyr Gly
225                 230                 235                 240

Ile Gly Ala Gly Ala Gly Ala Gly Ser Gly Ala Gly Ala Gly Ala Gly
             245                 250                 255

Ala Gly Ala Gly Ala Gly Gly Ala Gly Gly Tyr Gly Arg Gly Ala Gly
             260                 265                 270

Ala Gly Ala Gly Ala Ala Ala Ala Ala Gly Ala Gly Ala Gly Ala Gly
             275                 280                 285

Gly Ala Gly Gly Tyr Gly Arg Gly Ala Gly Ala Gly Ala Gly Ala Ala
             290                 295                 300

Ala Ala Ala Gly Thr Gly Ala Gly Ala Ala Gly Gly Tyr Gly Gly Gly
305                 310                 315                 320

Tyr Gly Gly Gly Ala Gly Ala Gly Val Gly Ala Gly Ala Gly Ala Gly
             325                 330                 335

Gly Ala Gly Gly Tyr Gly Arg Gly Ala Gly Ala Gly Ala Gly Ala Ala
             340                 345                 350

Ala Ala Ala Ser Ala Gly Ala Gly Ala Gly Gly Tyr Gly Gly Gly Tyr
             355                 360                 365

Gly Val Ala Gly Gly Ser Ser Ile Ser Tyr Gly Ala Thr Ser Ser Ser
 370                 375                 380

Ala Thr Ser Ser Ser Thr Ala Ser Ser Ser Arg Ser Gly Ile Val Thr
385                 390                 395                 400

Ser Gly Gly Tyr Gly Ala Gly Ala Ala Gly Ala Gly Ala Gly Ala Gly
             405                 410                 415

Ala Ala Gly Ala Gly Ser Tyr Ser Gly Ser Ile Ser Arg Leu Ser Ser
             420                 425                 430
```

-continued

```
Ala Glu Ala Val Asn Arg Val Ser Ser Asn Ile Gly Ala Val Ala Ser
        435                 440                 445

Gly Gly Ala Ser Ala Leu Pro Gly Val Ile Ser Asn Ile Phe Ser Gly
    450                 455                 460

Val Ser Ser Ser Ala Gly Ser Tyr Glu Glu Ala Val Ile Gln Ser Leu
465                 470                 475                 480

Leu Glu Val Leu Ser Val Leu Leu His Ile Leu Ser Asn Ser Ser Ile
                485                 490                 495

Gly Tyr Val Gly Ala Glu Gly Leu Gly Asp Ser Leu Ala Val Val Gln
            500                 505                 510

Gln Ala Val Gly Pro Val Val Gly
        515                 520

<210> SEQ ID NO 22
<211> LENGTH: 227
<212> TYPE: PRT
<213> ORGANISM: Argiope

<400> SEQUENCE: 22

Ser Gly Tyr Gly Ala Gly Ala Gly Gly Ser Gly Ala Gly Ala Gly Ser
 1               5                  10                  15

Val Ala Gly Ser Gly Tyr Gly Arg Gly Phe Ala Leu Ala Ala Ala Ala
            20                  25                  30

Gly Ser Gly Ala Gly Ala Ala Ser Arg Ala Gly Tyr Gly Ala Gly Ala
        35                  40                  45

Gly Ser Gly Ala Gly Ala Gly Ser Gly Ala Gly Ala Gly Ser Gly Ser
    50                  55                  60

Gly Ala Gly Tyr Gly Val Gly Ala Gly Ser Gly Ala Gly Ala Gly Ser
65                  70                  75                  80

Gly Ala Gly Ala Gly Tyr Gly Ala Gly Ala Gly Ser Gly Ala Gly Ala
                85                  90                  95

Gly Ser Gly Ala Gly Ala Gly Ser Gly Ala Gly Ser Gly Tyr Gly Arg
            100                 105                 110

Gly Phe Gly Ala Gly Ala Gly Ser Gly Ala Gly Ala Gly Ser Gly Ala
        115                 120                 125

Gly Tyr Gly Ala Gly Ala Gly Ser Gly Ala Gly Ala Gly Ser Gly Ala
    130                 135                 140

Gly Ala Gly Ser Gly Ser Gly Ala Gly Tyr Gly Val Gly Ala Gly Ser
145                 150                 155                 160

Gly Ala Gly Ala Gly Ser Gly Ala Gly Ala Gly Ser Gly Ser Gly Ala
                165                 170                 175

Gly Tyr Gly Arg Gly Phe Gly Ala Gly Ala Gly Ser Gly Ala Gly Ala
            180                 185                 190

Gly Ser Gly Val Gly Ala Gly Ser Gly Ser Gly Ala Gly Tyr Gly Arg
        195                 200                 205

Arg Phe Gly Ala Gly Ala Gly Tyr Gly Ala Gly Ser Gly Ala Gly Ala
    210                 215                 220

Gly Ser Gly
225

<210> SEQ ID NO 23
<211> LENGTH: 200
<212> TYPE: PRT
<213> ORGANISM: Artificial Sequence
<220> FEATURE:
<223> OTHER INFORMATION: consensus sequence repeat of the A. trifasciata
      aciniform fibroin 1 protein
```

-continued

```
<400> SEQUENCE: 23

Ser Ser Val Val Gln Arg Ala Ala Gln Ser Leu Ala Ser Thr Leu Gly
1               5                   10                  15

Val Asp Gly Asn Asn Leu Ala Arg Phe Ala Val Gln Ala Val Ser Arg
            20                  25                  30

Leu Pro Ala Gly Ser Asp Thr Ser Ala Tyr Ala Gln Ala Phe Ser Ser
        35                  40                  45

Ala Leu Phe Asn Ala Gly Val Leu Asn Ala Ser Asn Ile Asp Thr Leu
    50                  55                  60

Gly Ser Arg Val Leu Ser Ala Leu Leu Asn Gly Val Ser Ser Ala Ala
65                  70                  75                  80

Gln Gly Leu Gly Ile Asn Val Asp Ser Gly Ser Val Gln Ser Asp Ile
                85                  90                  95

Ser Ser Ser Ser Ser Phe Leu Ser Thr Ser Ser Ser Ala Ser Tyr
            100                 105                 110

Ser Gln Ala Ser Ala Ser Ser Thr Ser Gly Ala Gly Tyr Thr Gly Pro
        115                 120                 125

Ser Gly Pro Ser Thr Gly Pro Ser Gly Tyr Pro Gly Pro Leu Gly Gly
    130                 135                 140

Gly Ala Pro Phe Gly Gln Ser Gly Phe Gly Ser Ala Gly Pro Gln
145                 150                 155                 160

Gly Gly Phe Gly Ala Thr Gly Gly Ala Ser Ala Gly Leu Ile Ser Arg
                165                 170                 175

Val Ala Asn Ala Leu Ala Asn Thr Ser Thr Leu Arg Thr Val Leu Arg
            180                 185                 190

Thr Gly Val Ser Gln Gln Ile Ala
        195                 200

<210> SEQ ID NO 24
<211> LENGTH: 5
<212> TYPE: PRT
<213> ORGANISM: Artificial Sequence
<220> FEATURE:
<221> NAME/KEY: misc_feature
<222> LOCATION: (4, 5)
<223> OTHER INFORMATION: Xaa = any amino acid

<400> SEQUENCE: 24

Gly Pro Gly Xaa Xaa
1               5

<210> SEQ ID NO 25
<211> LENGTH: 10
<212> TYPE: PRT
<213> ORGANISM: Araneus

<400> SEQUENCE: 25

Gly Pro Gly Gln Gln Gly Pro Gly Gln Gln
1               5                   10

<210> SEQ ID NO 26
<211> LENGTH: 14
<212> TYPE: PRT
<213> ORGANISM: Lactrodectus

<400> SEQUENCE: 26

Gly Pro Gly Gly Tyr Gly Pro Gly Pro Gly Gly Gln Gln Gly
1               5                   10
```

```
<210> SEQ ID NO 27
<211> LENGTH: 25
<212> TYPE: PRT
<213> ORGANISM: Argiope

<400> SEQUENCE: 27

Gly Pro Gly Ala Gly Gln Gln Gly Pro Gly Ser Gln Gly Pro Gly Ser
1               5                   10                  15

Gly Gly Gln Gln Gly Pro Gly Gln Gln
            20                  25

<210> SEQ ID NO 28
<211> LENGTH: 7
<212> TYPE: PRT
<213> ORGANISM: Nephila

<400> SEQUENCE: 28

Gly Pro Tyr Gly Pro Gly Ser
1               5

<210> SEQ ID NO 29
<211> LENGTH: 10
<212> TYPE: PRT
<213> ORGANISM: Argiope

<400> SEQUENCE: 29

Gly Pro Gly Gly Tyr Gly Pro Gly Gln Gln
1               5                   10

<210> SEQ ID NO 30
<211> LENGTH: 15
<212> TYPE: PRT
<213> ORGANISM: Argiope
<220> FEATURE:
<221> NAME/KEY: misc_feature
<222> LOCATION: (11)
<223> OTHER INFORMATION: Xaa = any amino acid

<400> SEQUENCE: 30

Gly Pro Gly Gly Tyr Gly Pro Gly Pro Gly Xaa Gln Gln Gly Tyr
1               5                   10                  15

<210> SEQ ID NO 31
<211> LENGTH: 24
<212> TYPE: PRT
<213> ORGANISM: Argiope

<400> SEQUENCE: 31

Gly Pro Gly Ala Gly Gln Gln Gly Pro Ser Gln Gly Pro Gly Ser Gly
1               5                   10                  15

Gly Gln Gln Gly Pro Gly Gly Gln
            20

<210> SEQ ID NO 32
<211> LENGTH: 25
<212> TYPE: PRT
<213> ORGANISM: Argiope

<400> SEQUENCE: 32

Gly Pro Gly Ser Gly Gln Gln Gly Pro Gly Gln Gln Gly Pro Gly Ser
1               5                   10                  15

Gly Gly Gln Gln Gly Pro Gly Gly Gln
            20                  25
```

```
<210> SEQ ID NO 33
<211> LENGTH: 18
<212> TYPE: PRT
<213> ORGANISM: Argiope

<400> SEQUENCE: 33

Gly Pro Gly Gly Tyr Gly Pro Gly Ser Gln Gly Pro Ser Gly Pro Gly
1               5                   10                  15

Ala Tyr

<210> SEQ ID NO 34
<211> LENGTH: 15
<212> TYPE: PRT
<213> ORGANISM: Argiope

<400> SEQUENCE: 34

Gly Pro Gly Gly Gln Gly Pro Gly Gln Gln Gly Pro Gly Gly Tyr
1               5                   10                  15

<210> SEQ ID NO 35
<211> LENGTH: 5
<212> TYPE: PRT
<213> ORGANISM: Argiope
<220> FEATURE:
<221> NAME/KEY: misc_feature
<222> LOCATION: (5)
<223> OTHER INFORMATION: Xaa = Ala, Tyr, Ser, or Val

<400> SEQUENCE: 35

Gly Pro Gly Gly Xaa
1               5

<210> SEQ ID NO 36
<211> LENGTH: 7
<212> TYPE: PRT
<213> ORGANISM: Argiope

<400> SEQUENCE: 36

Gly Pro Ser Gly Pro Gly Ser
1               5

<210> SEQ ID NO 37
<211> LENGTH: 6
<212> TYPE: PRT
<213> ORGANISM: Argiope

<400> SEQUENCE: 37

Gly Pro Tyr Gly Pro Ser
1               5

<210> SEQ ID NO 38
<211> LENGTH: 6
<212> TYPE: PRT
<213> ORGANISM: Araneus

<400> SEQUENCE: 38

Gly Pro Tyr Gly Pro Gly
1               5

<210> SEQ ID NO 39
<211> LENGTH: 6
<212> TYPE: PRT
<213> ORGANISM: Argiope

<400> SEQUENCE: 39
```

```
Gly Pro Gly Gly Pro Gly
1               5

<210> SEQ ID NO 40
<211> LENGTH: 8
<212> TYPE: PRT
<213> ORGANISM: Argiope

<400> SEQUENCE: 40

Gly Pro Gly Gly Pro Gly Ser Ser
1               5

<210> SEQ ID NO 41
<211> LENGTH: 9
<212> TYPE: PRT
<213> ORGANISM: Argiope

<400> SEQUENCE: 41

Gly Pro Ser Gly Pro Gly Gly Ala Ser
1               5

<210> SEQ ID NO 42
<211> LENGTH: 5
<212> TYPE: PRT
<213> ORGANISM: Argiope

<400> SEQUENCE: 42

Gly Pro Gly Ser Gly
1               5

<210> SEQ ID NO 43
<211> LENGTH: 47
<212> TYPE: PRT
<213> ORGANISM: Artificial Sequence
<220> FEATURE:
<223> OTHER INFORMATION: synthetic spider silk protein repeat

<400> SEQUENCE: 43

Gly Pro Gly Gly Tyr Gly Pro Gly Gln Gln Gly Pro Gly Gly Tyr Gly
1               5                   10                  15

Pro Gly Gln Gln Gly Pro Gly Gly Tyr Gly Pro Gly Gln Gln Ala Ala
            20                  25                  30

Ala Ala Ala Ala Ala Ala Ala Gly Pro Gly Gly Pro Gly Ser Ser
        35                  40                  45

<210> SEQ ID NO 44
<211> LENGTH: 60
<212> TYPE: PRT
<213> ORGANISM: Artificial Sequence
<220> FEATURE:
<223> OTHER INFORMATION: synthetic spider silk protein repeat

<400> SEQUENCE: 44

Gly Pro Gly Gln Gln Gly Pro Gly Gln Gln Gly Pro Gly Gln Gln Gly
1               5                   10                  15

Pro Gly Gln Gln Gly Pro Gly Gln Gln Gly Pro Gly Gln Gln Gly Pro
            20                  25                  30

Gly Gln Gln Gly Pro Gly Gln Gln Gly Ala Gly Ala Gly Ala Gly Ala
        35                  40                  45

Gly Ala Gly Ala Gly Ala Gly Pro Tyr Gly Pro Gly
    50                  55                  60
```

```
<210> SEQ ID NO 45
<211> LENGTH: 171
<212> TYPE: PRT
<213> ORGANISM: Artificial Sequence
<220> FEATURE:
<223> OTHER INFORMATION: synthetic spider silk protein repeat

<400> SEQUENCE: 45

Gly Pro Gly Gly Ser Gly Pro Gly Gly Tyr Gly Pro Gly Gly Ser Gly
 1               5                  10                  15

Pro Gly Gly Tyr Gly Pro Gly Gly Ala Gly Pro Gly Gly Ser Gly Pro
             20                  25                  30

Gly Gly Tyr Gly Pro Gly Gly Ser Gly Pro Gly Gly Tyr Gly Pro Gly
         35                  40                  45

Gly Ala Gly Pro Gly Gly Ser Gly Pro Gly Gly Tyr Gly Pro Gly Gly
     50                  55                  60

Ser Gly Pro Gly Gly Tyr Gly Pro Gly Gly Ala Gly Pro Gly Gly Ser
 65                  70                  75                  80

Gly Pro Gly Gly Tyr Gly Pro Gly Gly Ser Gly Pro Gly Gly Tyr Gly
                 85                  90                  95

Pro Gly Gly Ala Gly Pro Gly Gly Ser Gly Pro Gly Gly Tyr Gly Pro
            100                 105                 110

Gly Gly Ser Gly Pro Gly Gly Tyr Gly Pro Gly Gly Ala Gly Pro Gly
        115                 120                 125

Gly Ser Gly Pro Gly Gly Tyr Gly Pro Gly Gly Ser Gly Pro Gly Gly
    130                 135                 140

Tyr Gly Pro Gly Gly Ala Gly Gly Ala Gly Gly Ala Gly Gly Ala Gly
145                 150                 155                 160

Gly Ala Gly Gly Ala Gly Pro Tyr Gly Pro Ser
                165                 170

<210> SEQ ID NO 46
<211> LENGTH: 63
<212> TYPE: PRT
<213> ORGANISM: Artificial Sequence
<220> FEATURE:
<223> OTHER INFORMATION: synthetic spider silk protein repeat

<400> SEQUENCE: 46

Gly Pro Gly Gly Ser Gly Pro Gly Gly Tyr Gly Pro Gly Gly Ser Gly
 1               5                  10                  15

Pro Gly Gly Tyr Gly Pro Gly Gly Ser Gly Pro Gly Gly Tyr Gly Pro
             20                  25                  30

Gly Gly Ser Gly Pro Gly Gly Tyr Gly Pro Gly Gly Ser Gly Pro Gly
         35                  40                  45

Gly Tyr Ala Ala Ala Ala Ala Ala Gly Pro Ser Gly Pro Gly Ser
     50                  55                  60

<210> SEQ ID NO 47
<211> LENGTH: 36
<212> TYPE: PRT
<213> ORGANISM: Artificial Sequence
<220> FEATURE:
<223> OTHER INFORMATION: synthetic spider silk protein repeat

<400> SEQUENCE: 47

Gly Gly Tyr Gly Gly Leu Gly Gly Gln Gly Gly Tyr Gly Gly Leu Gly
 1               5                  10                  15

Gly Gln Gly Ala Gly Ala Gly Ala Gly Ala Gly Ala Gly Ala Gly Ala
             20                  25                  30
```

Gly Ala Gly Ala
        35

<210> SEQ ID NO 48
<211> LENGTH: 32
<212> TYPE: PRT
<213> ORGANISM: Artificial Sequence
<220> FEATURE:
<223> OTHER INFORMATION: synthetic spider silk protein repeat

<400> SEQUENCE: 48

Gly Gly Val Gly Gly Ala Gly Gly Val Gly Gly Ala Gly Gly Val Gly
1               5                   10                  15

Gly Ala Gly Val Gly Val Gly Val Gly Val Gly Val Gly Val Gly Val
            20                  25                  30

<210> SEQ ID NO 49
<211> LENGTH: 1128
<212> TYPE: PRT
<213> ORGANISM: Artificial Sequence
<220> FEATURE:
<223> OTHER INFORMATION: synthetic spider silk protein

<400> SEQUENCE: 49

Gly Pro Gly Gly Tyr Gly Pro Gly Gln Gln Gly Pro Gly Gly Tyr Gly
1               5                   10                  15

Pro Gly Gln Gln Gly Pro Gly Gly Tyr Gly Pro Gly Gln Gln Ala Ala
            20                  25                  30

Ala Ala Ala Ala Ala Ala Gly Pro Gly Gly Pro Gly Ser Ser Gly Pro
        35                  40                  45

Gly Gly Tyr Gly Pro Gly Gln Gln Gly Pro Gly Gly Tyr Gly Pro Gly
    50                  55                  60

Gln Gln Gly Pro Gly Gly Tyr Gly Pro Gly Gln Gln Ala Ala Ala Ala
65                  70                  75                  80

Ala Ala Ala Ala Ala Ala Gly Pro Gly Gly Pro Gly Ser Ser Gly Pro
                85                  90                  95

Gly Gly Tyr Gly Pro Gly Gln Gln Gly Pro Gly Gly Tyr Gly Pro Gly
            100                 105                 110

Gln Gln Gly Pro Gly Gly Tyr Gly Pro Gly Gln Gln Ala Ala Ala Ala
        115                 120                 125

Ala Ala Ala Ala Ala Gly Pro Gly Gly Pro Gly Ser Ser Gly Pro Gly
    130                 135                 140

Gly Tyr Gly Pro Gly Gln Gln Gly Pro Gly Gly Tyr Gly Pro Gly Gln
145                 150                 155                 160

Gln Gly Pro Gly Gly Tyr Gly Pro Gly Gln Gln Ala Ala Ala Ala Ala
                165                 170                 175

Ala Ala Ala Gly Pro Gly Gly Pro Gly Ser Ser Gly Pro Gly Gly
            180                 185                 190

Tyr Gly Pro Gly Gln Gln Gly Pro Gly Gly Tyr Gly Pro Gly Gln Gln
        195                 200                 205

Gly Pro Gly Gly Tyr Gly Pro Gly Gln Gln Ala Ala Ala Ala Ala Ala
    210                 215                 220

Ala Ala Ala Gly Pro Gly Gly Pro Gly Ser Ser Gly Pro Gly Gly Tyr
225                 230                 235                 240

Gly Pro Gly Gln Gln Gly Pro Gly Gly Tyr Gly Pro Gly Gln Gln Gly
                245                 250                 255

Pro Gly Gly Tyr Gly Pro Gly Gln Gln Ala Ala Ala Ala Ala Ala Ala

-continued

```
                260                 265                 270
Ala Ala Gly Pro Gly Gly Pro Gly Ser Ser Gly Pro Gly Gly Tyr Gly
            275                 280                 285
Pro Gly Gln Gln Gly Pro Gly Gly Tyr Gly Pro Gly Gln Gln Gly Pro
            290                 295                 300
Gly Gly Tyr Gly Pro Gly Gln Gln Ala Ala Ala Ala Ala Ala Ala Ala
305                 310                 315                 320
Ala Gly Pro Gly Gly Pro Gly Ser Ser Gly Pro Gly Gly Tyr Gly Pro
                325                 330                 335
Gly Gln Gln Gly Pro Gly Gly Tyr Gly Pro Gly Gln Gln Gly Pro Gly
            340                 345                 350
Gly Tyr Gly Pro Gly Gln Gln Ala Ala Ala Ala Ala Ala Ala Ala Ala
            355                 360                 365
Gly Pro Gly Gly Pro Gly Ser Ser Gly Pro Gly Gly Tyr Gly Pro Gly
            370                 375                 380
Gln Gln Gly Pro Gly Gly Tyr Gly Pro Gly Gln Gln Gly Pro Gly Gly
385                 390                 395                 400
Tyr Gly Pro Gly Gln Gln Ala Ala Ala Ala Ala Ala Ala Ala Ala Gly
                405                 410                 415
Pro Gly Gly Pro Gly Ser Ser Gly Pro Gly Gly Tyr Gly Pro Gly Gln
            420                 425                 430
Gln Gly Pro Gly Gly Tyr Gly Pro Gly Gln Gln Gly Pro Gly Gly Tyr
            435                 440                 445
Gly Pro Gly Gln Gln Ala Ala Ala Ala Ala Ala Ala Ala Gly Pro
            450                 455                 460
Gly Gly Pro Gly Ser Ser Gly Pro Gly Gly Tyr Gly Pro Gly Gln Gln
465                 470                 475                 480
Gly Pro Gly Gly Tyr Gly Pro Gly Gln Gln Gly Pro Gly Gly Tyr Gly
                485                 490                 495
Pro Gly Gln Gln Ala Ala Ala Ala Ala Ala Ala Ala Gly Pro Gly
            500                 505                 510
Gly Pro Gly Ser Ser Gly Pro Gly Gly Tyr Gly Pro Gly Gln Gln Gly
            515                 520                 525
Pro Gly Gly Tyr Gly Pro Gly Gln Gln Gly Pro Gly Gly Tyr Gly Pro
            530                 535                 540
Gly Gln Gln Ala Ala Ala Ala Ala Ala Ala Ala Gly Pro Gly Gly
545                 550                 555                 560
Pro Gly Ser Ser Gly Pro Gly Gly Tyr Gly Pro Gly Gln Gln Gly Pro
                565                 570                 575
Gly Gly Tyr Gly Pro Gly Gln Gln Gly Pro Gly Gly Tyr Gly Pro Gly
            580                 585                 590
Gln Gln Ala Ala Ala Ala Ala Ala Ala Ala Gly Pro Gly Gly Pro
            595                 600                 605
Gly Ser Ser Gly Pro Gly Gly Tyr Gly Pro Gly Gln Gln Gly Pro Gly
            610                 615                 620
Gly Tyr Gly Pro Gly Gln Gln Gly Pro Gly Gly Tyr Gly Pro Gly Gln
625                 630                 635                 640
Gln Ala Ala Ala Ala Ala Ala Ala Ala Gly Pro Gly Gly Pro Gly
                645                 650                 655
Ser Ser Gly Pro Gly Gly Tyr Gly Pro Gly Gln Gln Gly Pro Gly Gly
            660                 665                 670
Tyr Gly Pro Gly Gln Gln Gly Pro Gly Gly Tyr Gly Pro Gly Gln Gln
            675                 680                 685
```

```
Ala Ala Ala Ala Ala Ala Ala Ala Gly Pro Gly Gly Pro Gly Ser
    690                 695                 700

Ser Gly Pro Gly Gly Tyr Gly Pro Gly Gln Gln Gly Pro Gly Tyr
705                 710                 715                 720

Gly Pro Gly Gln Gln Gly Pro Gly Gly Tyr Gly Pro Gly Gln Ala
                725                 730                 735

Ala Ala Ala Ala Ala Ala Ala Gly Pro Gly Pro Gly Ser Ser
            740                 745                 750

Gly Pro Gly Gly Tyr Gly Pro Gly Gln Gln Gly Pro Gly Tyr Gly
                755                 760                 765

Pro Gly Gln Gln Gly Pro Gly Gly Tyr Gly Pro Gly Gln Ala Ala
        770                 775                 780

Ala Ala Ala Ala Ala Ala Gly Pro Gly Pro Gly Ser Ser Gly
785                 790                 795                 800

Pro Gly Gly Tyr Gly Pro Gly Gln Gln Gly Pro Gly Tyr Gly Pro
                805                 810                 815

Gly Gln Gln Gly Pro Gly Gly Tyr Gly Pro Gly Gln Ala Ala Ala
            820                 825                 830

Ala Ala Ala Ala Ala Ala Gly Pro Gly Gly Pro Gly Ser Ser Gly Pro
            835                 840                 845

Gly Gly Tyr Gly Pro Gly Gln Gln Gly Pro Gly Gly Tyr Gly Pro Gly
    850                 855                 860

Gln Gln Gly Pro Gly Gly Tyr Gly Pro Gly Gln Ala Ala Ala Ala
865                 870                 875                 880

Ala Ala Ala Ala Ala Gly Pro Gly Gly Pro Gly Ser Ser Gly Pro Gly
                885                 890                 895

Gly Tyr Gly Pro Gly Gln Gln Gly Pro Gly Gly Tyr Gly Pro Gly Gln
                900                 905                 910

Gln Gly Pro Gly Gly Tyr Gly Pro Gly Gln Ala Ala Ala Ala Ala
        915                 920                 925

Ala Ala Ala Ala Gly Pro Gly Gly Pro Gly Ser Ser Gly Pro Gly Gly
    930                 935                 940

Tyr Gly Pro Gly Gln Gln Gly Pro Gly Gly Tyr Gly Pro Gly Gln Gln
945                 950                 955                 960

Gly Pro Gly Gly Tyr Gly Pro Gly Gln Ala Ala Ala Ala Ala
                965                 970                 975

Ala Ala Ala Gly Pro Gly Gly Pro Gly Ser Ser Gly Pro Gly Gly Tyr
            980                 985                 990

Gly Pro Gly Gln Gln Gly Pro Gly Gly Tyr Gly Pro Gly Gln Gln Gly
                995                1000                1005

Pro Gly Gly Tyr Gly Pro Gly Gln Ala Ala Ala Ala Ala Ala
    1010                1015                1020

Ala Ala Gly Pro Gly Gly Pro Gly Ser Ser Gly Pro Gly Gly Tyr Gly
1025                1030                1035                1040

Pro Gly Gln Gln Gly Pro Gly Gly Tyr Gly Pro Gly Gln Gln Gly Pro
                1045                1050                1055

Gly Gly Tyr Gly Pro Gly Gln Ala Ala Ala Ala Ala Ala Ala Ala
        1060                1065                1070

Ala Gly Pro Gly Gly Pro Gly Ser Ser Gly Pro Gly Gly Tyr Gly Pro
        1075                1080                1085

Gly Gln Gln Gly Pro Gly Gly Tyr Gly Pro Gly Gln Gln Gly Pro Gly
    1090                1095                1100
```

-continued

```
Gly Tyr Gly Pro Gly Gln Gln Ala Ala Ala Ala Ala Ala Ala
1105                1110                1115                1120

Gly Pro Gly Gly Pro Gly Ser Ser
            1125

<210> SEQ ID NO 50
<211> LENGTH: 3000
<212> TYPE: PRT
<213> ORGANISM: Artificial Sequence
<220> FEATURE:
<223> OTHER INFORMATION: synthetic spider silk protein

<400> SEQUENCE: 50

Gly Pro Gly Gln Gln Gly Pro Gly Gln Gln Gly Pro Gly Gln Gln Gly
 1               5                   10                  15

Pro Gly Gln Gln Gly Pro Gly Gln Gln Gly Pro Gly Gln Gln Gly Pro
                20                  25                  30

Gly Gln Gln Gly Pro Gly Gln Gln Gly Ala Gly Ala Gly Ala Gly Ala
            35                  40                  45

Gly Ala Gly Ala Gly Ala Gly Pro Tyr Gly Pro Gly Pro Gly Pro Gln
        50                  55                  60

Gln Gly Pro Gly Gln Gln Gly Pro Gly Gln Gln Gly Pro Gly Gln Gln
65                  70                  75                  80

Gly Pro Gly Gln Gln Gly Pro Gly Gln Gln Gly Pro Gly Gln Gln Gly
                85                  90                  95

Pro Gly Gln Gln Gly Ala Gly Ala Gly Ala Gly Ala Gly Ala Gly Ala
            100                 105                 110

Gly Ala Gly Pro Tyr Gly Pro Gly Pro Gly Pro Gln Gln Gly Pro Gly
        115                 120                 125

Gln Gln Gly Pro Gly Gln Gln Gly Pro Gly Gln Gln Gly Pro Gly Gln
    130                 135                 140

Gln Gly Pro Gly Gln Gln Gly Pro Gly Gln Gln Gly Pro Gly Gln Gln
145                 150                 155                 160

Gly Ala Gly Ala Gly Ala Gly Ala Gly Ala Gly Ala Gly Ala Gly Pro
                165                 170                 175

Tyr Gly Pro Gly Gly Pro Gly Gln Gln Gly Pro Gly Gln Gln Gly Pro
            180                 185                 190

Gly Gln Gln Gly Pro Gly Gln Gln Gly Pro Gly Gln Gln Gly Pro Gly
        195                 200                 205

Gln Gln Gly Pro Gly Gln Gln Gly Pro Gly Gln Gln Gly Ala Gly Ala
    210                 215                 220

Gly Ala Gly Ala Gly Ala Gly Ala Gly Ala Gly Pro Tyr Gly Pro Gly
225                 230                 235                 240

Gly Pro Gly Gln Gln Gly Pro Gly Gln Gln Gly Pro Gly Gln Gln Gly
                245                 250                 255

Pro Gly Gln Gln Gly Pro Gly Gln Gln Gly Pro Gly Gln Gln Gly Pro
            260                 265                 270

Gly Gln Gln Gly Pro Gly Gln Gln Gly Ala Gly Ala Gly Ala Gly Ala
        275                 280                 285

Gly Ala Gly Ala Gly Ala Gly Pro Tyr Gly Pro Gly Gly Pro Gly Gln
    290                 295                 300

Gln Gly Pro Gly Gln Gln Gly Pro Gly Gln Gln Gly Pro Gly Gln Gln
305                 310                 315                 320

Gly Pro Gly Gln Gln Gly Pro Gly Gln Gln Gly Pro Gly Gln Gln Gly
                325                 330                 335
```

-continued

```
Pro Gly Gln Gln Gly Ala Gly Ala Gly Ala Gly Ala Gly Ala
            340                 345                 350

Gly Ala Gly Pro Tyr Gly Pro Gly Gly Pro Gly Gln Gln Gly Pro Gly
            355                 360                 365

Gln Gln Gly Pro Gly Gln Gln Gly Pro Gly Gln Gln Gly Pro Gly Gln
            370                 375                 380

Gln Gly Pro Gly Gln Gln Gly Pro Gly Gln Gln Gly Pro Gly Gln Gln
385                 390                 395                 400

Gly Ala Gly Ala Gly Ala Gly Ala Gly Ala Gly Ala Gly Ala Gly Pro
                405                 410                 415

Tyr Gly Pro Gly Gly Pro Gly Gln Gln Gly Pro Gly Gln Gln Gly Pro
            420                 425                 430

Gly Gln Gln Gly Pro Gly Gln Gln Gly Pro Gly Gln Gln Gly Pro Gly
            435                 440                 445

Gln Gln Gly Pro Gly Gln Gln Gly Pro Gly Gln Gln Gly Ala Gly Ala
            450                 455                 460

Gly Ala Gly Ala Gly Ala Gly Ala Gly Ala Gly Pro Tyr Gly Pro Gly
465                 470                 475                 480

Gly Pro Gly Gln Gln Gly Pro Gly Gln Gln Gly Pro Gly Gln Gln Gly
                485                 490                 495

Pro Gly Gln Gln Gly Pro Gly Gln Gln Gly Pro Gly Gln Gln Gly Pro
            500                 505                 510

Gly Gln Gln Gly Pro Gly Gln Gln Gly Ala Gly Ala Gly Ala Gly Ala
            515                 520                 525

Gly Ala Gly Ala Gly Ala Gly Pro Tyr Gly Pro Gly Gly Pro Gly Gln
            530                 535                 540

Gln Gly Pro Gly Gln Gln Gly Pro Gly Gln Gln Gly Pro Gly Gln Gln
545                 550                 555                 560

Gly Pro Gly Gln Gln Gly Pro Gly Gln Gln Gly Pro Gly Gln Gln Gly
                565                 570                 575

Pro Gly Gln Gln Gly Ala Gly Ala Gly Ala Gly Ala Gly Ala Gly Ala
            580                 585                 590

Gly Ala Gly Pro Tyr Gly Pro Gly Pro Gly Gln Gln Gly Pro Gly
            595                 600                 605

Gln Gln Gly Pro Gly Gln Gln Gly Pro Gly Gln Gln Gly Pro Gly Gln
            610                 615                 620

Gln Gly Pro Gly Gln Gln Gly Pro Gly Gln Gln Gly Pro Gly Gln Gln
625                 630                 635                 640

Gly Ala Gly Ala Gly Ala Gly Ala Gly Ala Gly Ala Gly Ala Gly Pro
                645                 650                 655

Tyr Gly Pro Gly Gly Pro Gly Gln Gln Gly Pro Gly Gln Gln Gly Pro
            660                 665                 670

Gly Gln Gln Gly Pro Gly Gln Gln Gly Pro Gly Gln Gln Gly Pro Gly
            675                 680                 685

Gln Gln Gly Pro Gly Gln Gln Gly Pro Gly Gln Gln Gly Ala Gly Ala
            690                 695                 700

Gly Ala Gly Ala Gly Ala Gly Ala Gly Ala Gly Pro Tyr Gly Pro Gly
705                 710                 715                 720

Gly Pro Gly Gln Gln Gly Pro Gly Gln Gln Gly Pro Gly Gln Gln Gly
                725                 730                 735

Pro Gly Gln Gln Gly Pro Gly Gln Gln Gly Pro Gly Gln Gln Gly Pro
            740                 745                 750

Gly Gln Gln Gly Pro Gly Gln Gln Gly Ala Gly Ala Gly Ala Gly Ala
```

```
                    755                 760                 765
Gly Ala Gly Ala Gly Ala Gly Pro Tyr Gly Pro Gly Gly Pro Gly Gln
    770                 775                 780
Gln Gly Pro Gly Gln Gln Gly Pro Gly Gln Gln Gly Pro Gly Gln Gln
785                 790                 795                 800
Gly Pro Gly Gln Gln Gly Pro Gly Gln Gln Gly Pro Gly Gln Gln Gly
                805                 810                 815
Pro Gly Gln Gln Gly Ala Gly Ala Gly Ala Gly Ala Gly Ala Gly Ala
            820                 825                 830
Gly Ala Gly Pro Tyr Gly Pro Gly Gly Pro Gly Gln Gln Gly Pro Gly
            835                 840                 845
Gln Gln Gly Pro Gly Gln Gln Gly Pro Gly Gln Gln Gly Pro Gly Gln
    850                 855                 860
Gln Gly Pro Gly Gln Gln Gly Pro Gly Gln Gln Gly Pro Gly Gln Gln
865                 870                 875                 880
Gly Ala Gly Ala Gly Ala Gly Ala Gly Ala Gly Ala Gly Ala Gly Pro
                885                 890                 895
Tyr Gly Pro Gly Gly Pro Gly Gln Gln Gly Pro Gly Gln Gln Gly Pro
                900                 905                 910
Gly Gln Gln Gly Pro Gly Gln Gln Gly Pro Gly Gln Gln Gly Pro Gly
            915                 920                 925
Gln Gln Gly Pro Gly Gln Gln Gly Pro Gly Gln Gln Gly Ala Gly Ala
    930                 935                 940
Gly Ala Gly Ala Gly Ala Gly Ala Gly Pro Tyr Gly Pro Gly
945                 950                 955                 960
Gly Pro Gly Gln Gln Gly Pro Gly Gln Gln Gly Pro Gly Gln Gln Gly
                965                 970                 975
Pro Gly Gln Gln Gly Pro Gly Gln Gln Gly Pro Gly Gln Gln Gly Pro
            980                 985                 990
Gly Gln Gln Gly Pro Gly Gln Gln Gly Ala Gly Ala Gly Ala Gly Ala
            995                1000                1005
Gly Ala Gly Ala Gly Pro Tyr Gly Pro Gly Gly Pro Gly Gln
    1010                1015                1020
Gln Gly Pro Gly Gln Gln Gly Pro Gly Gln Gln Gly Pro Gly Gln Gln
1025                1030                1035                1040
Gly Pro Gly Gln Gln Gly Pro Gly Gln Gln Gly Pro Gly Gln Gln Gly
                1045                1050                1055
Pro Gly Gln Gln Gly Ala Gly Ala Gly Ala Gly Ala Gly Ala
            1060                1065                1070
Gly Ala Gly Pro Tyr Gly Pro Gly Gly Pro Gly Gln Gln Gly Pro Gly
            1075                1080                1085
Gln Gln Gly Pro Gly Gln Gln Gly Pro Gly Gln Gln Gly Pro Gly Gln
    1090                1095                1100
Gln Gly Pro Gly Gln Gln Gly Pro Gly Gln Gln Gly Pro Gly Gln Gln
1105                1110                1115                1120
Gly Ala Gly Ala Gly Ala Gly Ala Gly Ala Gly Ala Gly Ala Gly Pro
                1125                1130                1135
Tyr Gly Pro Gly Gly Pro Gly Gln Gln Gly Pro Gly Gln Gln Gly Pro
                1140                1145                1150
Gly Gln Gln Gly Pro Gly Gln Gln Gly Pro Gly Gln Gln Gly Pro Gly
            1155                1160                1165
Gln Gln Gly Pro Gly Gln Gln Gly Pro Gly Gln Gln Gly Ala Gly Ala
    1170                1175                1180
```

-continued

```
Gly Ala Gly Ala Gly Ala Gly Ala Gly Ala Gly Pro Tyr Gly Pro Gly
1185                1190                1195                1200

Gly Pro Gly Gln Gln Gly Pro Gly Gln Gln Gly Pro Gly Gln Gln Gly
            1205                1210                1215

Pro Gly Gln Gln Gly Pro Gly Gln Gln Gly Pro Gly Gln Gln Gly Pro
        1220                1225                1230

Gly Gln Gln Gly Pro Gly Gln Gln Gly Ala Gly Ala Gly Ala Gly Ala
    1235                1240                1245

Gly Ala Gly Ala Gly Ala Gly Pro Tyr Gly Pro Gly Gly Pro Gly Gln
1250                1255                1260

Gln Gly Pro Gly Gln Gln Gly Pro Gly Gln Gln Gly Pro Gly Gln Gln
1265                1270                1275                1280

Gly Pro Gly Gln Gln Gly Pro Gly Gln Gln Gly Pro Gly Gln Gln Gly
            1285                1290                1295

Pro Gly Gln Gln Gly Ala Gly Ala Gly Ala Gly Ala Gly Ala Gly Ala
        1300                1305                1310

Gly Ala Gly Pro Tyr Gly Pro Gly Gly Pro Gly Gln Gln Gly Pro Gly
    1315                1320                1325

Gln Gln Gly Pro Gly Gln Gln Gly Pro Gly Gln Gln Gly Pro Gly Gln
        1330                1335                1340

Gln Gly Pro Gly Gln Gln Gly Pro Gly Gln Gln Gly Pro Gly Gln Gln
1345                1350                1355                1360

Gly Ala Gly Ala Gly Ala Gly Ala Gly Ala Gly Ala Gly Ala Gly Pro
            1365                1370                1375

Tyr Gly Pro Gly Gly Pro Gly Gln Gln Gly Pro Gly Gln Gln Gly Pro
        1380                1385                1390

Gly Gln Gln Gly Pro Gly Gln Gln Gly Pro Gly Gln Gln Gly Pro Gly
    1395                1400                1405

Gln Gln Gly Pro Gly Gln Gln Gly Pro Gly Gln Gln Gly Ala Gly Ala
    1410                1415                1420

Gly Ala Gly Ala Gly Ala Gly Ala Gly Pro Tyr Gly Pro Gly
1425                1430                1435                1440

Gly Pro Gly Gln Gln Gly Pro Gly Gln Gln Gly Pro Gly Gln Gln Gly
            1445                1450                1455

Pro Gly Gln Gln Gly Pro Gly Gln Gln Gly Pro Gly Gln Gln Gly Pro
        1460                1465                1470

Gly Gln Gln Gly Pro Gly Gln Gln Gly Ala Gly Ala Gly Ala Gly Ala
    1475                1480                1485

Gly Ala Gly Ala Gly Pro Tyr Gly Pro Gly Gly Pro Gly Gln
1490                1495                1500

Gln Gly Pro Gly Gln Gln Gly Pro Gly Gln Gln Gly Pro Gly Gln Gln
1505                1510                1515                1520

Gly Pro Gly Gln Gln Gly Pro Gly Gln Gln Gly Pro Gly Gln Gln Gly
            1525                1530                1535

Pro Gly Gln Gln Gly Ala Gly Ala Gly Ala Gly Ala Gly Ala Gly Ala
        1540                1545                1550

Gly Ala Gly Pro Tyr Gly Pro Gly Gly Pro Gly Gln Gln Gly Pro Gly
    1555                1560                1565

Gln Gln Gly Pro Gly Gln Gln Gly Pro Gly Gln Gln Gly Pro Gly Gln
        1570                1575                1580

Gln Gly Pro Gly Gln Gln Gly Pro Gly Gln Gln Gly Pro Gly Gln Gln
1585                1590                1595                1600
```

```
Gly Ala Gly Ala Gly Ala Gly Ala Gly Ala Gly Ala Gly Ala Gly Pro
            1605                1610                1615

Tyr Gly Pro Gly Gly Pro Gly Gln Gln Gly Pro Gly Gln Gln Gly Pro
            1620                1625                1630

Gly Gln Gln Gly Pro Gly Gln Gln Gly Pro Gly Gln Gln Gly Pro Gly
            1635                1640                1645

Gln Gln Gly Pro Gly Gln Gln Gly Pro Gly Gln Gln Gly Ala Gly Ala
    1650                1655                1660

Gly Ala Gly Ala Gly Ala Gly Ala Gly Ala Gly Pro Tyr Gly Pro Gly
1665                1670                1675                1680

Gly Pro Gly Gln Gln Gly Pro Gly Gln Gln Gly Pro Gly Gln Gln Gly
            1685                1690                1695

Pro Gly Gln Gln Gly Pro Gly Gln Gln Gly Pro Gly Gln Gln Gly Pro
            1700                1705                1710

Gly Gln Gln Gly Pro Gly Gln Gln Gly Ala Gly Ala Gly Ala Gly Ala
            1715                1720                1725

Gly Ala Gly Ala Gly Ala Gly Pro Tyr Gly Pro Gly Gly Pro Gly Gln
            1730                1735                1740

Gln Gly Pro Gly Gln Gln Gly Pro Gly Gln Gln Gly Pro Gly Gln Gln
1745                1750                1755                1760

Gly Pro Gly Gln Gln Gly Pro Gly Gln Gln Gly Pro Gly Gln Gln Gly
            1765                1770                1775

Pro Gly Gln Gln Gly Ala Gly Ala Gly Ala Gly Ala Gly Ala Gly Ala
            1780                1785                1790

Gly Ala Gly Pro Tyr Gly Pro Gly Gly Pro Gly Gln Gln Gly Pro Gly
            1795                1800                1805

Gln Gln Gly Pro Gly Gln Gln Gly Pro Gly Gln Gln Gly Pro Gly Gln
            1810                1815                1820

Gln Gly Pro Gly Gln Gln Gly Pro Gly Gln Gln Gly Pro Gly Gln Gln
1825                1830                1835                1840

Gly Ala Gly Ala Gly Ala Gly Ala Gly Ala Gly Ala Gly Ala Gly Pro
            1845                1850                1855

Tyr Gly Pro Gly Gly Pro Gly Gln Gln Gly Pro Gly Gln Gln Gly Pro
            1860                1865                1870

Gly Gln Gln Gly Pro Gly Gln Gln Gly Pro Gly Gln Gln Gly Pro Gly
            1875                1880                1885

Gln Gln Gly Pro Gly Gln Gln Gly Pro Gly Gln Gln Gly Ala Gly Ala
    1890                1895                1900

Gly Ala Gly Ala Gly Ala Gly Ala Gly Ala Gly Pro Tyr Gly Pro Gly
1905                1910                1915                1920

Gly Pro Gly Gln Gln Gly Pro Gly Gln Gln Gly Pro Gly Gln Gln Gly
            1925                1930                1935

Pro Gly Gln Gln Gly Pro Gly Gln Gln Gly Pro Gly Gln Gln Gly Pro
            1940                1945                1950

Gly Gln Gln Gly Pro Gly Gln Gln Gly Ala Gly Ala Gly Ala Gly Ala
            1955                1960                1965

Gly Ala Gly Ala Gly Ala Gly Pro Tyr Gly Pro Gly Gly Pro Gly Gln
            1970                1975                1980

Gln Gly Pro Gly Gln Gln Gly Pro Gly Gln Gln Gly Pro Gly Gln Gln
1985                1990                1995                2000

Gly Pro Gly Gln Gln Gly Pro Gly Gln Gln Gly Pro Gly Gln Gln Gly
            2005                2010                2015

Pro Gly Gln Gln Gly Ala Gly Ala Gly Ala Gly Ala Gly Ala Gly Ala
```

-continued

```
                2020                2025                2030
Gly Ala Gly Pro Tyr Gly Pro Gly Gly Pro Gly Gln Gln Gly Pro Gly
            2035                2040                2045
Gln Gln Gly Pro Gly Gln Gln Gly Pro Gly Gln Gln Gly Pro Gly Gln
            2050                2055                2060
Gln Gly Pro Gly Gln Gln Gly Pro Gly Gln Gln Gly Pro Gly Gln Gln
2065                2070                2075                2080
Gly Ala Gly Ala Gly Ala Gly Ala Gly Ala Gly Ala Gly Ala Gly Pro
            2085                2090                2095
Tyr Gly Pro Gly Gly Pro Gly Gln Gln Gly Pro Gly Gln Gln Gly Pro
            2100                2105                2110
Gly Gln Gln Gly Pro Gly Gln Gln Gly Pro Gly Gln Gln Gly Pro Gly
            2115                2120                2125
Gln Gln Gly Pro Gly Gln Gln Gly Pro Gly Gln Gln Gly Ala Gly Ala
            2130                2135                2140
Gly Ala Gly Ala Gly Ala Gly Ala Gly Ala Gly Pro Tyr Gly Pro Gly
2145                2150                2155                2160
Gly Pro Gly Gln Gln Gly Pro Gly Gln Gln Gly Pro Gly Gln Gln Gly
            2165                2170                2175
Pro Gly Gln Gln Gly Pro Gly Gln Gln Gly Pro Gly Gln Gln Gly Pro
            2180                2185                2190
Gly Gln Gln Gly Pro Gly Gln Gln Gly Ala Gly Ala Gly Ala Gly Ala
            2195                2200                2205
Gly Ala Gly Ala Gly Ala Gly Pro Tyr Gly Pro Gly Gly Pro Gly Gln
            2210                2215                2220
Gln Gly Pro Gly Gln Gln Gly Pro Gly Gln Gln Gly Pro Gly Gln Gln
2225                2230                2235                2240
Gly Pro Gly Gln Gln Gly Pro Gly Gln Gln Gly Pro Gly Gln Gln Gly
            2245                2250                2255
Pro Gly Gln Gln Gly Ala Gly Ala Gly Ala Gly Ala Gly Ala Gly Ala
            2260                2265                2270
Gly Ala Gly Pro Tyr Gly Pro Gly Gly Pro Gly Gln Gln Gly Pro Gly
            2275                2280                2285
Gln Gln Gly Pro Gly Gln Gln Gly Pro Gly Gln Gln Gly Pro Gly Gln
            2290                2295                2300
Gln Gly Pro Gly Gln Gln Gly Pro Gly Gln Gln Gly Pro Gly Gln Gln
2305                2310                2315                2320
Gly Ala Gly Ala Gly Ala Gly Ala Gly Ala Gly Ala Gly Ala Gly Pro
            2325                2330                2335
Tyr Gly Pro Gly Gly Pro Gly Gln Gln Gly Pro Gly Gln Gln Gly Pro
            2340                2345                2350
Gly Gln Gln Gly Pro Gly Gln Gln Gly Pro Gly Gln Gln Gly Pro Gly
            2355                2360                2365
Gln Gln Gly Pro Gly Gln Gln Gly Pro Gly Gln Gln Gly Ala Gly Ala
            2370                2375                2380
Gly Ala Gly Ala Gly Ala Gly Ala Gly Ala Gly Pro Tyr Gly Pro Gly
2385                2390                2395                2400
Gly Pro Gly Gln Gln Gly Pro Gly Gln Gln Gly Pro Gly Gln Gln Gly
            2405                2410                2415
Pro Gly Gln Gln Gly Pro Gly Gln Gln Gly Pro Gly Gln Gln Gly Pro
            2420                2425                2430
Gly Gln Gln Gly Pro Gly Gln Gln Gly Ala Gly Ala Gly Ala Gly Ala
            2435                2440                2445
```

```
Gly Ala Gly Ala Gly Ala Gly Pro Tyr Gly Pro Gly Gly Pro Gly Gln
    2450                2455                2460
Gln Gly Pro Gly Gln Gln Gly Pro Gly Gln Gln Gly Pro Gly Gln Gln
2465                2470                2475                2480
Gly Pro Gly Gln Gln Gly Pro Gly Gln Gln Gly Pro Gly Gln Gln Gly
            2485                2490                2495
Pro Gly Gln Gln Gly Ala Gly Ala Gly Ala Gly Ala Gly Ala Gly Ala
        2500                2505                2510
Gly Ala Gly Pro Tyr Gly Pro Gly Gly Pro Gly Gln Gln Gly Pro Gly
            2515                2520                2525
Gln Gln Gly Pro Gly Gln Gln Gly Pro Gly Gln Gln Gly Pro Gly Gln
        2530                2535                2540
Gln Gly Pro Gly Gln Gln Gly Pro Gly Gln Gln Gly Pro Gly Gln Gln
2545                2550                2555                2560
Gly Ala Gly Ala Gly Ala Gly Ala Gly Ala Gly Ala Gly Ala Gly Pro
            2565                2570                2575
Tyr Gly Pro Gly Gly Pro Gly Gln Gln Gly Pro Gly Gln Gln Gly Pro
        2580                2585                2590
Gly Gln Gln Gly Pro Gly Gln Gln Gly Pro Gly Gln Gln Gly Pro Gly
        2595                2600                2605
Gln Gln Gly Pro Gly Gln Gln Gly Pro Gly Gln Gln Gly Ala Gly Ala
        2610                2615                2620
Gly Ala Gly Ala Gly Ala Gly Ala Gly Ala Gly Pro Tyr Gly Pro Gly
2625                2630                2635                2640
Gly Pro Gly Gln Gln Gly Pro Gly Gln Gln Gly Pro Gly Gln Gln Gly
            2645                2650                2655
Pro Gly Gln Gln Gly Pro Gly Gln Gln Gly Pro Gly Gln Gln Gly Pro
        2660                2665                2670
Gly Gln Gln Gly Pro Gly Gln Gln Gly Ala Gly Ala Gly Ala Gly Ala
            2675                2680                2685
Gly Ala Gly Ala Gly Ala Gly Pro Tyr Gly Pro Gly Gly Pro Gly Gln
        2690                2695                2700
Gln Gly Pro Gly Gln Gln Gly Pro Gly Gln Gln Gly Pro Gly Gln Gln
2705                2710                2715                2720
Gly Pro Gly Gln Gln Gly Pro Gly Gln Gln Gly Pro Gly Gln Gln Gly
            2725                2730                2735
Pro Gly Gln Gln Gly Ala Gly Ala Gly Ala Gly Ala Gly Ala Gly Ala
        2740                2745                2750
Gly Ala Gly Pro Tyr Gly Pro Gly Gly Pro Gly Gln Gln Gly Pro Gly
            2755                2760                2765
Gln Gln Gly Pro Gly Gln Gln Gly Pro Gly Gln Gln Gly Pro Gly Gln
        2770                2775                2780
Gln Gly Pro Gly Gln Gln Gly Pro Gly Gln Gln Gly Pro Gly Gln Gln
2785                2790                2795                2800
Gly Ala Gly Ala Gly Ala Gly Ala Gly Ala Gly Ala Gly Ala Gly Pro
            2805                2810                2815
Tyr Gly Pro Gly Gly Pro Gly Gln Gln Gly Pro Gly Gln Gln Gly Pro
        2820                2825                2830
Gly Gln Gln Gly Pro Gly Gln Gln Gly Pro Gly Gln Gln Gly Pro Gly
        2835                2840                2845
Gln Gln Gly Pro Gly Gln Gln Gly Pro Gly Gln Gln Gly Ala Gly Ala
2850                2855                2860
```

```
Gly Ala Gly Ala Gly Ala Gly Ala Gly Pro Tyr Gly Pro Gly
        2865                2870                2875                2880

Gly Pro Gly Gln Gln Gly Pro Gly Gln Gln Gly Pro Gly Gln Gln Gly
                    2885                2890                2895

Pro Gly Gln Gln Gly Pro Gly Gln Gln Gly Pro Gly Gln Gln Gly Pro
            2900                2905                2910

Gly Gln Gln Gly Pro Gly Gln Gln Gly Ala Gly Ala Gly Ala Gly Ala
        2915                2920                2925

Gly Ala Gly Ala Gly Ala Gly Pro Tyr Gly Pro Gly Pro Gly Gln
        2930                2935                2940

Gln Gly Pro Gly Gln Gln Pro Gly Gln Gln Gly Pro Gly Gln Gln
2945                2950                2955                2960

Gly Pro Gly Gln Gln Gly Pro Gly Gln Gln Gly Pro Gly Gln Gln Gly
                    2965                2970                2975

Pro Gly Gln Gln Gly Ala Gly Ala Gly Ala Gly Ala Gly Ala
            2980                2985                2990

Gly Ala Gly Pro Tyr Gly Pro Gly
        2995                3000

<210> SEQ ID NO 51
<211> LENGTH: 3420
<212> TYPE: PRT
<213> ORGANISM: Artificial Sequence
<220> FEATURE:
<223> OTHER INFORMATION: synthetic spider silk protein

<400> SEQUENCE: 51

Gly Pro Gly Gly Ser Gly Pro Gly Gly Tyr Gly Pro Gly Gly Ser Gly
 1               5                   10                  15

Pro Gly Gly Tyr Gly Pro Gly Gly Ala Gly Pro Gly Gly Ser Gly Pro
            20                  25                  30

Gly Gly Tyr Gly Pro Gly Gly Ser Gly Pro Gly Gly Tyr Gly Pro Gly
        35                  40                  45

Gly Ala Gly Pro Gly Gly Ser Gly Pro Gly Gly Tyr Gly Pro Gly Gly
    50                  55                  60

Ser Gly Pro Gly Gly Tyr Gly Pro Gly Gly Ala Gly Pro Gly Gly Ser
65                  70                  75                  80

Gly Pro Gly Gly Tyr Gly Pro Gly Gly Ser Gly Pro Gly Gly Tyr Gly
                85                  90                  95

Pro Gly Gly Ala Gly Pro Gly Gly Ser Gly Pro Gly Gly Tyr Gly Pro
            100                 105                 110

Gly Gly Ser Gly Pro Gly Gly Tyr Gly Pro Gly Gly Ala Gly Pro Gly
        115                 120                 125

Gly Ser Gly Pro Gly Gly Tyr Gly Pro Gly Gly Ser Gly Pro Gly Gly
    130                 135                 140

Tyr Gly Pro Gly Gly Ala Gly Ala Gly Gly Ala Gly Gly Ala Gly
145                 150                 155                 160

Gly Ala Gly Gly Ala Gly Pro Tyr Gly Pro Ser Gly Pro Gly Gly Ser
                165                 170                 175

Gly Pro Gly Gly Tyr Gly Pro Gly Gly Ser Gly Pro Gly Gly Tyr Gly
            180                 185                 190

Pro Gly Gly Ala Gly Pro Gly Gly Ser Gly Pro Gly Gly Tyr Gly Pro
        195                 200                 205

Gly Gly Ser Gly Pro Gly Gly Tyr Gly Pro Gly Gly Ala Gly Pro Gly
    210                 215                 220
```

-continued

```
Gly Ser Gly Pro Gly Gly Tyr Gly Pro Gly Gly Ser Gly Pro Gly Gly
225                 230                 235                 240
Tyr Gly Pro Gly Gly Ala Gly Pro Gly Gly Ser Gly Pro Gly Gly Tyr
                245                 250                 255
Gly Pro Gly Gly Ser Gly Pro Gly Gly Tyr Gly Pro Gly Gly Ala Gly
            260                 265                 270
Pro Gly Gly Ser Gly Pro Gly Gly Tyr Gly Pro Gly Gly Ser Gly Pro
        275                 280                 285
Gly Gly Tyr Gly Pro Gly Gly Ala Gly Pro Gly Gly Ser Gly Pro Gly
    290                 295                 300
Gly Tyr Gly Pro Gly Gly Ser Gly Pro Gly Gly Tyr Gly Pro Gly Gly
305                 310                 315                 320
Ala Gly Gly Ala Gly Gly Ala Gly Gly Ala Gly Gly Ala Gly Gly Ala
                325                 330                 335
Gly Pro Tyr Gly Pro Ser Gly Pro Gly Gly Ser Gly Pro Gly Gly Tyr
            340                 345                 350
Gly Pro Gly Gly Ser Gly Pro Gly Gly Tyr Gly Pro Gly Gly Ala Gly
        355                 360                 365
Pro Gly Gly Ser Gly Pro Gly Gly Tyr Gly Pro Gly Gly Ser Gly Pro
    370                 375                 380
Gly Gly Tyr Gly Pro Gly Gly Ala Gly Pro Gly Gly Ser Gly Pro Gly
385                 390                 395                 400
Gly Tyr Gly Pro Gly Gly Ser Gly Pro Gly Gly Tyr Gly Pro Gly Gly
                405                 410                 415
Ala Gly Pro Gly Gly Ser Gly Pro Gly Gly Tyr Gly Pro Gly Gly Ser
            420                 425                 430
Gly Pro Gly Gly Tyr Gly Pro Gly Gly Ala Gly Pro Gly Gly Ser Gly
        435                 440                 445
Pro Gly Gly Tyr Gly Pro Gly Gly Ser Gly Pro Gly Gly Tyr Gly Pro
    450                 455                 460
Gly Gly Ala Gly Pro Gly Gly Ser Gly Pro Gly Gly Tyr Gly Pro Gly
465                 470                 475                 480
Gly Ser Gly Pro Gly Gly Tyr Gly Pro Gly Gly Ala Gly Gly Ala Gly
                485                 490                 495
Gly Ala Gly Gly Ala Gly Gly Ala Gly Gly Ala Gly Pro Tyr Gly Pro
            500                 505                 510
Ser Gly Pro Gly Gly Ser Gly Pro Gly Gly Tyr Gly Pro Gly Gly Ser
        515                 520                 525
Gly Pro Gly Gly Tyr Gly Pro Gly Gly Ala Gly Pro Gly Gly Ser Gly
    530                 535                 540
Pro Gly Gly Tyr Gly Pro Gly Gly Ser Gly Pro Gly Gly Tyr Gly Pro
545                 550                 555                 560
Gly Gly Ala Gly Pro Gly Gly Ser Gly Pro Gly Gly Tyr Gly Pro Gly
                565                 570                 575
Gly Ser Gly Pro Gly Gly Tyr Gly Pro Gly Gly Ala Gly Pro Gly Gly
            580                 585                 590
Ser Gly Pro Gly Gly Tyr Gly Pro Gly Gly Ser Gly Pro Gly Gly Tyr
        595                 600                 605
Gly Pro Gly Gly Ala Gly Pro Gly Gly Ser Gly Pro Gly Gly Tyr Gly
    610                 615                 620
Pro Gly Gly Ser Gly Pro Gly Gly Tyr Gly Pro Gly Gly Ala Gly Pro
625                 630                 635                 640
Gly Gly Ser Gly Pro Gly Gly Tyr Gly Pro Gly Gly Ser Gly Pro Gly
```

-continued

```
               645                 650                 655
Gly Tyr Gly Pro Gly Gly Ala Gly Gly Ala Gly Gly Ala Gly Gly Ala
            660                 665                 670
Gly Gly Ala Gly Gly Ala Gly Pro Tyr Gly Pro Ser Gly Pro Gly Gly
            675                 680                 685
Ser Gly Pro Gly Gly Tyr Gly Pro Gly Gly Ser Gly Pro Gly Gly Tyr
            690                 695                 700
Gly Pro Gly Gly Ala Gly Pro Gly Gly Ser Gly Pro Gly Gly Tyr Gly
705                 710                 715                 720
Pro Gly Gly Ser Gly Pro Gly Gly Tyr Gly Pro Gly Gly Ala Gly Pro
            725                 730                 735
Gly Gly Ser Gly Pro Gly Gly Tyr Gly Pro Gly Gly Ser Gly Pro Gly
            740                 745                 750
Gly Tyr Gly Pro Gly Gly Ala Gly Pro Gly Gly Ser Gly Pro Gly Gly
            755                 760                 765
Tyr Gly Pro Gly Gly Ser Gly Pro Gly Gly Tyr Gly Pro Gly Gly Ala
            770                 775                 780
Gly Pro Gly Gly Ser Gly Pro Gly Gly Tyr Gly Pro Gly Gly Ser Gly
785                 790                 795                 800
Pro Gly Gly Tyr Gly Pro Gly Gly Ala Gly Pro Gly Gly Ser Gly Pro
            805                 810                 815
Gly Gly Tyr Gly Pro Gly Ser Gly Pro Gly Gly Tyr Gly Pro Gly
            820                 825                 830
Gly Ala Gly Gly Ala Gly Gly Ala Gly Gly Ala Gly Gly Ala Gly Gly
            835                 840                 845
Ala Gly Pro Tyr Gly Pro Ser Gly Pro Gly Ser Gly Pro Gly Gly
            850                 855                 860
Tyr Gly Pro Gly Gly Ser Gly Pro Gly Gly Tyr Gly Pro Gly Gly Ala
865                 870                 875                 880
Gly Pro Gly Gly Ser Gly Pro Gly Gly Tyr Gly Pro Gly Gly Ser Gly
            885                 890                 895
Pro Gly Gly Tyr Gly Pro Gly Gly Ala Gly Pro Gly Gly Ser Gly Pro
            900                 905                 910
Gly Gly Tyr Gly Pro Gly Gly Ser Gly Pro Gly Gly Tyr Gly Pro Gly
            915                 920                 925
Gly Ala Gly Pro Gly Gly Ser Gly Pro Gly Gly Tyr Gly Pro Gly Gly
            930                 935                 940
Ser Gly Pro Gly Gly Tyr Gly Pro Gly Gly Ala Gly Pro Gly Gly Ser
945                 950                 955                 960
Gly Pro Gly Gly Tyr Gly Pro Gly Gly Ser Gly Pro Gly Gly Tyr Gly
            965                 970                 975
Pro Gly Gly Ala Gly Pro Gly Gly Ser Gly Pro Gly Gly Tyr Gly Pro
            980                 985                 990
Gly Gly Ser Gly Pro Gly Gly Tyr Gly Pro Gly Gly Ala Gly Gly Ala
            995                1000                1005
Gly Gly Ala Gly Gly Ala Gly Gly Ala Gly Gly Ala Gly Pro Tyr Gly
           1010                1015                1020
Pro Ser Gly Pro Gly Gly Ser Gly Pro Gly Gly Tyr Gly Pro Gly Gly
1025                1030                1035                1040
Ser Gly Pro Gly Gly Tyr Gly Pro Gly Gly Ala Gly Pro Gly Gly Ser
           1045                1050                1055
Gly Pro Gly Gly Tyr Gly Pro Gly Gly Ser Gly Pro Gly Gly Tyr Gly
           1060                1065                1070
```

Pro Gly Gly Ala Gly Pro Gly Gly Ser Gly Pro Gly Gly Tyr Gly Pro
            1075                1080                1085

Gly Gly Ser Gly Pro Gly Gly Tyr Gly Pro Gly Gly Ala Gly Pro Gly
            1090                1095                1100

Gly Ser Gly Pro Gly Gly Tyr Gly Pro Gly Gly Ser Gly Pro Gly Gly
1105                1110                1115                1120

Tyr Gly Pro Gly Gly Ala Gly Pro Gly Gly Ser Gly Pro Gly Gly Tyr
            1125                1130                1135

Gly Pro Gly Gly Ser Gly Pro Gly Gly Tyr Gly Pro Gly Gly Ala Gly
            1140                1145                1150

Pro Gly Gly Ser Gly Pro Gly Gly Tyr Gly Pro Gly Gly Ser Gly Pro
            1155                1160                1165

Gly Gly Tyr Gly Pro Gly Gly Ala Gly Gly Ala Gly Ala Gly Gly
            1170                1175                1180

Ala Gly Gly Ala Gly Gly Ala Gly Pro Tyr Gly Pro Ser Gly Pro Gly
1185                1190                1195                1200

Gly Ser Gly Pro Gly Gly Tyr Gly Pro Gly Gly Ser Gly Pro Gly Gly
            1205                1210                1215

Tyr Gly Pro Gly Gly Ala Gly Pro Gly Gly Ser Gly Pro Gly Gly Tyr
            1220                1225                1230

Gly Pro Gly Gly Ser Gly Pro Gly Gly Tyr Gly Pro Gly Gly Ala Gly
            1235                1240                1245

Pro Gly Gly Ser Gly Pro Gly Gly Tyr Gly Pro Gly Gly Ser Gly Pro
            1250                1255                1260

Gly Gly Tyr Gly Pro Gly Gly Ala Gly Pro Gly Gly Ser Gly Pro Gly
1265                1270                1275                1280

Gly Tyr Gly Pro Gly Gly Ser Gly Pro Gly Gly Tyr Gly Pro Gly Gly
            1285                1290                1295

Ala Gly Pro Gly Gly Ser Gly Pro Gly Gly Tyr Gly Pro Gly Gly Ser
            1300                1305                1310

Gly Pro Gly Gly Tyr Gly Pro Gly Gly Ala Gly Pro Gly Gly Ser Gly
            1315                1320                1325

Pro Gly Gly Tyr Gly Pro Gly Gly Ser Gly Pro Gly Gly Tyr Gly Pro
            1330                1335                1340

Gly Gly Ala Gly Gly Ala Gly Gly Ala Gly Gly Ala Gly Gly Ala Gly
1345                1350                1355                1360

Gly Ala Gly Pro Tyr Gly Pro Ser Gly Pro Gly Gly Ser Gly Pro Gly
            1365                1370                1375

Gly Tyr Gly Pro Gly Gly Ser Gly Pro Gly Gly Tyr Gly Pro Gly Gly
            1380                1385                1390

Ala Gly Pro Gly Gly Ser Gly Pro Gly Gly Tyr Gly Pro Gly Gly Ser
            1395                1400                1405

Gly Pro Gly Gly Tyr Gly Pro Gly Gly Ala Gly Pro Gly Gly Ser Gly
            1410                1415                1420

Pro Gly Gly Tyr Gly Pro Gly Gly Ser Gly Pro Gly Gly Tyr Gly Pro
1425                1430                1435                1440

Gly Gly Ala Gly Pro Gly Gly Ser Gly Pro Gly Gly Tyr Gly Pro Gly
            1445                1450                1455

Gly Ser Gly Pro Gly Gly Tyr Gly Pro Gly Gly Ala Gly Pro Gly Gly
            1460                1465                1470

Ser Gly Pro Gly Gly Tyr Gly Pro Gly Gly Ser Gly Pro Gly Gly Tyr
            1475                1480                1485

-continued

```
Gly Pro Gly Gly Ala Gly Pro Gly Gly Ser Gly Pro Gly Gly Tyr Gly
    1490                1495                1500
Pro Gly Gly Ser Gly Pro Gly Gly Tyr Gly Pro Gly Gly Ala Gly Gly
1505                1510                1515                1520
Ala Gly Gly Ala Gly Gly Ala Gly Gly Ala Gly Gly Ala Gly Pro Tyr
                1525                1530                1535
Gly Pro Ser Gly Pro Gly Ser Gly Pro Gly Gly Tyr Gly Pro Gly
        1540                1545                1550
Gly Ser Gly Pro Gly Gly Tyr Gly Pro Gly Gly Ala Gly Pro Gly Gly
            1555                1560                1565
Ser Gly Pro Gly Gly Tyr Gly Pro Gly Gly Ser Gly Pro Gly Gly Tyr
    1570                1575                1580
Gly Pro Gly Gly Ala Gly Pro Gly Gly Ser Gly Pro Gly Gly Tyr Gly
1585                1590                1595                1600
Pro Gly Gly Ser Gly Pro Gly Gly Tyr Gly Pro Gly Gly Ala Gly Pro
                1605                1610                1615
Gly Gly Ser Gly Pro Gly Gly Tyr Gly Pro Gly Gly Ser Gly Pro Gly
        1620                1625                1630
Gly Tyr Gly Pro Gly Gly Ala Gly Pro Gly Gly Ser Gly Pro Gly Gly
            1635                1640                1645
Tyr Gly Pro Gly Gly Ser Gly Pro Gly Gly Tyr Gly Pro Gly Gly Ala
    1650                1655                1660
Gly Pro Gly Gly Ser Gly Pro Gly Gly Tyr Gly Pro Gly Gly Ser Gly
1665                1670                1675                1680
Pro Gly Gly Tyr Gly Pro Gly Gly Ala Gly Gly Ala Gly Gly Ala Gly
                1685                1690                1695
Gly Ala Gly Gly Ala Gly Gly Ala Gly Pro Tyr Gly Pro Ser Gly Pro
        1700                1705                1710
Gly Gly Ser Gly Pro Gly Gly Tyr Gly Pro Gly Gly Ser Gly Pro Gly
            1715                1720                1725
Gly Tyr Gly Pro Gly Gly Ala Gly Pro Gly Gly Ser Gly Pro Gly Gly
    1730                1735                1740
Tyr Gly Pro Gly Gly Ser Gly Pro Gly Gly Tyr Gly Pro Gly Gly Ala
1745                1750                1755                1760
Gly Pro Gly Gly Ser Gly Pro Gly Gly Tyr Gly Pro Gly Gly Ser Gly
                1765                1770                1775
Pro Gly Gly Tyr Gly Pro Gly Gly Ala Gly Pro Gly Gly Ser Gly Pro
        1780                1785                1790
Gly Gly Tyr Gly Pro Gly Gly Ser Gly Pro Gly Gly Tyr Gly Pro Gly
            1795                1800                1805
Gly Ala Gly Pro Gly Gly Ser Gly Pro Gly Gly Tyr Gly Pro Gly Gly
    1810                1815                1820
Ser Gly Pro Gly Gly Tyr Gly Pro Gly Gly Ala Gly Pro Gly Gly Ser
1825                1830                1835                1840
Gly Pro Gly Gly Tyr Gly Pro Gly Gly Ser Gly Pro Gly Gly Tyr Gly
                1845                1850                1855
Pro Gly Gly Ala Gly Gly Ala Gly Gly Ala Gly Gly Ala Gly Gly Ala
        1860                1865                1870
Gly Gly Ala Gly Pro Tyr Gly Pro Ser Gly Pro Gly Gly Ser Gly Pro
            1875                1880                1885
Gly Gly Tyr Gly Pro Gly Gly Ser Gly Pro Gly Gly Tyr Gly Pro Gly
            1890                1895                1900
Gly Ala Gly Pro Gly Gly Ser Gly Pro Gly Gly Tyr Gly Pro Gly Gly
```

-continued

```
            1905                1910                1915                1920
Ser Gly Pro Gly Gly Tyr Gly Pro Gly Gly Ala Gly Pro Gly Gly Ser
                1925                1930                1935
Gly Pro Gly Gly Tyr Gly Pro Gly Gly Ser Gly Pro Gly Gly Tyr Gly
                1940                1945                1950
Pro Gly Gly Ala Gly Pro Gly Gly Ser Gly Pro Gly Gly Tyr Gly Pro
                1955                1960                1965
Gly Gly Ser Gly Pro Gly Gly Tyr Gly Pro Gly Gly Ala Gly Pro Gly
                1970                1975                1980
Gly Ser Gly Pro Gly Gly Tyr Gly Pro Gly Gly Ser Gly Pro Gly Gly
1985                1990                1995                2000
Tyr Gly Pro Gly Gly Ala Gly Pro Gly Gly Ser Gly Pro Gly Gly Tyr
                2005                2010                2015
Gly Pro Gly Gly Ser Gly Pro Gly Gly Tyr Gly Pro Gly Gly Ala Gly
                2020                2025                2030
Gly Ala Gly Gly Ala Gly Gly Ala Gly Gly Ala Gly Gly Ala Gly Pro
                2035                2040                2045
Tyr Gly Pro Ser Gly Pro Gly Gly Ser Gly Pro Gly Gly Tyr Gly Pro
                2050                2055                2060
Gly Gly Ser Gly Pro Gly Gly Tyr Gly Pro Gly Gly Ala Gly Pro Gly
2065                2070                2075                2080
Gly Ser Gly Pro Gly Gly Tyr Gly Pro Gly Gly Ser Gly Pro Gly Gly
                2085                2090                2095
Tyr Gly Pro Gly Gly Ala Gly Pro Gly Gly Ser Gly Pro Gly Gly Tyr
                2100                2105                2110
Gly Pro Gly Gly Ser Gly Pro Gly Gly Tyr Gly Pro Gly Gly Ala Gly
                2115                2120                2125
Pro Gly Gly Ser Gly Pro Gly Gly Tyr Gly Pro Gly Gly Ser Gly Pro
                2130                2135                2140
Gly Gly Tyr Gly Pro Gly Gly Ala Gly Pro Gly Gly Ser Gly Pro Gly
2145                2150                2155                2160
Gly Tyr Gly Pro Gly Gly Ser Gly Pro Gly Gly Tyr Gly Pro Gly Gly
                2165                2170                2175
Ala Gly Pro Gly Gly Ser Gly Pro Gly Gly Tyr Gly Pro Gly Gly Ser
                2180                2185                2190
Gly Pro Gly Gly Tyr Gly Pro Gly Gly Ala Gly Gly Ala Gly Gly Ala
                2195                2200                2205
Gly Gly Ala Gly Gly Ala Gly Gly Ala Gly Pro Tyr Gly Pro Ser Gly
                2210                2215                2220
Pro Gly Gly Ser Gly Pro Gly Gly Tyr Gly Pro Gly Gly Ser Gly Pro
2225                2230                2235                2240
Gly Gly Tyr Gly Pro Gly Gly Ala Gly Pro Gly Gly Ser Gly Pro Gly
                2245                2250                2255
Gly Tyr Gly Pro Gly Gly Ser Gly Pro Gly Gly Tyr Gly Pro Gly Gly
                2260                2265                2270
Ala Gly Pro Gly Gly Ser Gly Pro Gly Gly Tyr Gly Pro Gly Gly Ser
                2275                2280                2285
Gly Pro Gly Gly Tyr Gly Pro Gly Gly Ala Gly Pro Gly Gly Ser Gly
                2290                2295                2300
Pro Gly Gly Tyr Gly Pro Gly Gly Ser Gly Pro Gly Gly Tyr Gly Pro
2305                2310                2315                2320
Gly Gly Ala Gly Pro Gly Gly Ser Gly Pro Gly Gly Tyr Gly Pro Gly
                2325                2330                2335
```

-continued

```
Gly Ser Gly Pro Gly Gly Tyr Gly Pro Gly Gly Ala Gly Pro Gly Gly
            2340                2345                2350

Ser Gly Pro Gly Gly Tyr Gly Pro Gly Gly Ser Gly Pro Gly Gly Tyr
            2355                2360                2365

Gly Pro Gly Gly Ala Gly Gly Ala Gly Gly Ala Gly Gly Ala Gly Gly
        2370                2375                2380

Ala Gly Gly Ala Gly Pro Tyr Gly Pro Ser Gly Pro Gly Gly Ser Gly
2385                2390                2395                2400

Pro Gly Gly Tyr Gly Pro Gly Gly Ser Gly Pro Gly Gly Tyr Gly Pro
        2405                2410                2415

Gly Gly Ala Gly Pro Gly Gly Ser Gly Pro Gly Gly Tyr Gly Pro Gly
            2420                2425                2430

Gly Ser Gly Pro Gly Gly Tyr Gly Pro Gly Gly Ala Gly Pro Gly Gly
            2435                2440                2445

Ser Gly Pro Gly Gly Tyr Gly Pro Gly Gly Ser Gly Pro Gly Gly Tyr
        2450                2455                2460

Gly Pro Gly Gly Ala Gly Pro Gly Gly Ser Gly Pro Gly Gly Tyr Gly
2465                2470                2475                2480

Pro Gly Gly Ser Gly Pro Gly Gly Tyr Gly Pro Gly Gly Ala Gly Pro
            2485                2490                2495

Gly Gly Ser Gly Pro Gly Gly Tyr Gly Pro Gly Gly Ser Gly Pro Gly
        2500                2505                2510

Gly Tyr Gly Pro Gly Gly Ala Gly Pro Gly Gly Ser Gly Pro Gly Gly
            2515                2520                2525

Tyr Gly Pro Gly Gly Ser Gly Pro Gly Gly Tyr Gly Pro Gly Gly Ala
        2530                2535                2540

Gly Gly Ala Gly Gly Ala Gly Gly Ala Gly Gly Ala Gly Gly Ala Gly
2545                2550                2555                2560

Pro Tyr Gly Pro Ser Gly Pro Gly Gly Ser Gly Pro Gly Gly Tyr Gly
            2565                2570                2575

Pro Gly Gly Ser Gly Pro Gly Gly Tyr Gly Pro Gly Gly Ala Gly Pro
        2580                2585                2590

Gly Gly Ser Gly Pro Gly Gly Tyr Gly Pro Gly Gly Ser Gly Pro Gly
            2595                2600                2605

Gly Tyr Gly Pro Gly Gly Ala Gly Pro Gly Gly Ser Gly Pro Gly Gly
        2610                2615                2620

Tyr Gly Pro Gly Gly Ser Gly Pro Gly Gly Tyr Gly Pro Gly Gly Ala
2625                2630                2635                2640

Gly Pro Gly Gly Ser Gly Pro Gly Gly Tyr Gly Pro Gly Gly Ser Gly
            2645                2650                2655

Pro Gly Gly Tyr Gly Pro Gly Gly Ala Gly Pro Gly Gly Ser Gly Pro
        2660                2665                2670

Gly Gly Tyr Gly Pro Gly Gly Ser Gly Pro Gly Gly Tyr Gly Pro Gly
            2675                2680                2685

Gly Ala Gly Pro Gly Gly Ser Gly Pro Gly Gly Tyr Gly Pro Gly Gly
        2690                2695                2700

Ser Gly Pro Gly Gly Tyr Gly Pro Gly Gly Ala Gly Gly Ala Gly Gly
        2705                2710                2715                2720

Ala Gly Gly Ala Gly Gly Ala Gly Gly Ala Gly Pro Tyr Gly Pro Ser
            2725                2730                2735

Gly Pro Gly Gly Ser Gly Pro Gly Gly Tyr Gly Pro Gly Gly Ser Gly
        2740                2745                2750
```

```
Pro Gly Gly Tyr Gly Pro Gly Gly Ala Gly Pro Gly Gly Ser Gly Pro
        2755                2760                2765

Gly Gly Tyr Gly Pro Gly Gly Ser Gly Pro Gly Gly Tyr Gly Pro Gly
    2770                2775                2780

Gly Ala Gly Pro Gly Gly Ser Gly Pro Gly Gly Tyr Gly Pro Gly Gly
2785                2790                2795                2800

Ser Gly Pro Gly Gly Tyr Gly Pro Gly Gly Ala Gly Pro Gly Gly Ser
        2805                2810                2815

Gly Pro Gly Gly Tyr Gly Pro Gly Gly Ser Gly Pro Gly Gly Tyr Gly
        2820                2825                2830

Pro Gly Gly Ala Gly Pro Gly Gly Ser Gly Pro Gly Gly Tyr Gly Pro
        2835                2840                2845

Gly Gly Ser Gly Pro Gly Gly Tyr Gly Pro Gly Gly Ala Gly Pro Gly
        2850                2855                2860

Gly Ser Gly Pro Gly Gly Tyr Gly Pro Gly Gly Ser Gly Pro Gly Gly
2865                2870                2875                2880

Tyr Gly Pro Gly Gly Ala Gly Ala Gly Gly Ala Gly Gly Ala Gly Gly
        2885                2890                2895

Gly Ala Gly Gly Ala Gly Pro Tyr Gly Pro Ser Gly Pro Gly Gly Ser
        2900                2905                2910

Gly Pro Gly Gly Tyr Gly Pro Gly Gly Ser Gly Pro Gly Gly Tyr Gly
        2915                2920                2925

Pro Gly Gly Ala Gly Pro Gly Gly Ser Gly Pro Gly Gly Tyr Gly Pro
        2930                2935                2940

Gly Gly Ser Gly Pro Gly Gly Tyr Gly Pro Gly Gly Ala Gly Pro Gly
2945                2950                2955                2960

Gly Ser Gly Pro Gly Gly Tyr Gly Pro Gly Gly Ser Gly Pro Gly Gly
        2965                2970                2975

Tyr Gly Pro Gly Gly Ala Gly Pro Gly Gly Ser Gly Pro Gly Gly Tyr
        2980                2985                2990

Gly Pro Gly Gly Ser Gly Pro Gly Gly Tyr Gly Pro Gly Gly Ala Gly
        2995                3000                3005

Pro Gly Gly Ser Gly Pro Gly Gly Tyr Gly Pro Gly Gly Ser Gly Pro
        3010                3015                3020

Gly Gly Tyr Gly Pro Gly Gly Ala Gly Pro Gly Gly Ser Gly Pro Gly
3025                3030                3035                3040

Gly Tyr Gly Pro Gly Gly Ser Gly Pro Gly Gly Tyr Gly Pro Gly Gly
            3045                3050                3055

Ala Gly Gly Ala Gly Gly Ala Gly Gly Ala Gly Gly Ala Gly Gly Ala
        3060                3065                3070

Gly Pro Tyr Gly Pro Ser Gly Pro Gly Gly Ser Gly Pro Gly Gly Tyr
        3075                3080                3085

Gly Pro Gly Gly Ser Gly Pro Gly Gly Tyr Gly Pro Gly Gly Ala Gly
        3090                3095                3100

Pro Gly Gly Ser Gly Pro Gly Gly Tyr Gly Pro Gly Gly Ser Gly Pro
3105                3110                3115                3120

Gly Gly Tyr Gly Pro Gly Gly Ala Gly Pro Gly Gly Ser Gly Pro Gly
            3125                3130                3135

Gly Tyr Gly Pro Gly Gly Ser Gly Pro Gly Gly Tyr Gly Pro Gly Gly
        3140                3145                3150

Ala Gly Pro Gly Gly Ser Gly Pro Gly Gly Tyr Gly Pro Gly Gly Ser
        3155                3160                3165

Gly Pro Gly Gly Tyr Gly Pro Gly Gly Ala Gly Pro Gly Gly Ser Gly
```

-continued

```
                3170                3175                3180
Pro Gly Gly Tyr Gly Pro Gly Gly Ser Gly Pro Gly Gly Tyr Gly Pro
3185                3190                3195                3200
Gly Gly Ala Gly Pro Gly Gly Ser Gly Pro Gly Gly Tyr Gly Pro Gly
                3205                3210                3215
Gly Ser Gly Pro Gly Gly Tyr Gly Pro Gly Gly Ala Gly Gly Ala Gly
                3220                3225                3230
Gly Ala Gly Gly Ala Gly Gly Ala Gly Gly Ala Gly Pro Tyr Gly Pro
            3235                3240                3245
Ser Gly Pro Gly Gly Ser Gly Pro Gly Gly Tyr Gly Pro Gly Gly Ser
            3250                3255                3260
Gly Pro Gly Gly Tyr Gly Pro Gly Gly Ala Gly Pro Gly Gly Ser Gly
3265                3270                3275                3280
Pro Gly Gly Tyr Gly Pro Gly Gly Ser Gly Pro Gly Gly Tyr Gly Pro
                3285                3290                3295
Gly Gly Ala Gly Pro Gly Gly Ser Gly Pro Gly Gly Tyr Gly Pro Gly
                3300                3305                3310
Gly Ser Gly Pro Gly Gly Tyr Gly Pro Gly Gly Ala Gly Pro Gly Gly
                3315                3320                3325
Ser Gly Pro Gly Gly Tyr Gly Pro Gly Gly Ser Gly Pro Gly Gly Tyr
            3330                3335                3340
Gly Pro Gly Gly Ala Gly Pro Gly Gly Ser Gly Pro Gly Gly Tyr Gly
3345                3350                3355                3360
Pro Gly Gly Ser Gly Pro Gly Gly Tyr Gly Pro Gly Gly Ala Gly Pro
                3365                3370                3375
Gly Gly Ser Gly Pro Gly Gly Tyr Gly Pro Gly Gly Ser Gly Pro Gly
                3380                3385                3390
Gly Tyr Gly Pro Gly Gly Ala Gly Ala Gly Gly Ala Gly Gly Ala
            3395                3400                3405
Gly Gly Ala Gly Gly Ala Gly Pro Tyr Gly Pro Ser
    3410                3415                3420
```

<210> SEQ ID NO 52
<211> LENGTH: 2016
<212> TYPE: PRT
<213> ORGANISM: Artificial Sequence
<220> FEATURE:
<223> OTHER INFORMATION: synthetic spider silk protein

<400> SEQUENCE: 52

```
Gly Pro Gly Gly Ser Gly Pro Gly Gly Tyr Gly Pro Gly Gly Ser Gly
1               5                   10                  15
Pro Gly Tyr Gly Pro Gly Gly Ser Gly Pro Gly Gly Tyr Gly Pro
                20                  25                  30
Gly Gly Ser Gly Pro Gly Gly Tyr Gly Pro Gly Gly Ser Gly Pro Gly
            35                  40                  45
Gly Tyr Ala Ala Ala Ala Ala Ala Gly Pro Ser Gly Pro Gly Ser Gly
    50                  55                  60
Pro Gly Gly Ser Gly Pro Gly Gly Tyr Gly Pro Gly Gly Ser Gly Pro
65                  70                  75                  80
Gly Gly Tyr Gly Pro Gly Gly Ser Gly Pro Gly Gly Tyr Gly Pro Gly
                85                  90                  95
Gly Ser Gly Pro Gly Gly Tyr Gly Pro Gly Gly Ser Gly Pro Gly Gly
            100                 105                 110
Tyr Ala Ala Ala Ala Ala Ala Gly Pro Ser Gly Pro Gly Ser Gly Pro
```

-continued

```
                115                 120                 125
Gly Gly Ser Gly Pro Gly Gly Tyr Gly Pro Gly Ser Gly Pro Gly
        130                 135                 140
Gly Tyr Gly Pro Gly Gly Ser Gly Pro Gly Gly Tyr Gly Pro Gly Gly
145                 150                 155                 160
Ser Gly Pro Gly Gly Tyr Gly Pro Gly Gly Ser Gly Pro Gly Gly Tyr
                165                 170                 175
Ala Ala Ala Ala Ala Ala Gly Pro Ser Gly Pro Ser Gly Pro Gly
                180                 185                 190
Gly Ser Gly Pro Gly Gly Tyr Gly Pro Gly Gly Ser Gly Pro Gly Gly
            195                 200                 205
Tyr Gly Pro Gly Gly Ser Gly Pro Gly Gly Tyr Gly Pro Gly Gly Ser
        210                 215                 220
Gly Pro Gly Gly Tyr Gly Pro Gly Gly Ser Gly Pro Gly Gly Tyr Ala
225                 230                 235                 240
Ala Ala Ala Ala Gly Pro Ser Gly Pro Ser Gly Pro Gly Gly
                245                 250                 255
Ser Gly Pro Gly Gly Tyr Gly Pro Gly Gly Ser Gly Pro Gly Gly Tyr
            260                 265                 270
Gly Pro Gly Gly Ser Gly Pro Gly Gly Tyr Gly Pro Gly Gly Ser Gly
        275                 280                 285
Pro Gly Gly Tyr Gly Pro Gly Gly Ser Gly Pro Gly Gly Tyr Ala Ala
290                 295                 300
Ala Ala Ala Ala Gly Pro Ser Gly Pro Ser Gly Pro Gly Gly Ser
305                 310                 315                 320
Gly Pro Gly Gly Tyr Gly Pro Gly Gly Ser Gly Pro Gly Gly Tyr Gly
            325                 330                 335
Pro Gly Gly Ser Gly Pro Gly Gly Tyr Gly Pro Gly Gly Ser Gly Pro
        340                 345                 350
Gly Gly Tyr Gly Pro Gly Gly Ser Gly Pro Gly Gly Tyr Ala Ala Ala
            355                 360                 365
Ala Ala Ala Gly Pro Ser Gly Pro Gly Ser Gly Pro Gly Gly Ser Gly
        370                 375                 380
Pro Gly Gly Tyr Gly Pro Gly Gly Ser Gly Pro Gly Gly Tyr Gly Pro
385                 390                 395                 400
Gly Gly Ser Gly Pro Gly Gly Tyr Gly Pro Gly Gly Ser Gly Pro Gly
                405                 410                 415
Gly Tyr Gly Pro Gly Gly Ser Gly Pro Gly Gly Tyr Ala Ala Ala Ala
            420                 425                 430
Ala Ala Gly Pro Ser Gly Pro Gly Ser Gly Pro Gly Gly Ser Gly Pro
        435                 440                 445
Gly Gly Tyr Gly Pro Gly Gly Ser Gly Pro Gly Gly Tyr Gly Pro Gly
        450                 455                 460
Gly Ser Gly Pro Gly Gly Tyr Gly Pro Gly Gly Ser Gly Pro Gly Gly
465                 470                 475                 480
Tyr Gly Pro Gly Gly Ser Gly Pro Gly Gly Tyr Ala Ala Ala Ala Ala
                485                 490                 495
Ala Gly Pro Ser Gly Pro Gly Ser Gly Pro Gly Gly Ser Gly Pro Gly
            500                 505                 510
Gly Tyr Gly Pro Gly Gly Ser Gly Pro Gly Gly Tyr Gly Pro Gly Gly
        515                 520                 525
Ser Gly Pro Gly Gly Tyr Gly Pro Gly Gly Ser Gly Pro Gly Gly Tyr
        530                 535                 540
```

-continued

```
Gly Pro Gly Gly Ser Gly Pro Gly Gly Tyr Ala Ala Ala Ala Ala
545                 550                 555                 560

Gly Pro Ser Gly Pro Gly Ser Gly Pro Gly Gly Ser Gly Pro Gly Gly
                565                 570                 575

Tyr Gly Pro Gly Gly Ser Gly Pro Gly Gly Tyr Gly Pro Gly Gly Ser
                580                 585                 590

Gly Pro Gly Gly Tyr Gly Pro Gly Gly Ser Gly Pro Gly Gly Tyr Gly
            595                 600                 605

Pro Gly Gly Ser Gly Pro Gly Gly Tyr Ala Ala Ala Ala Ala Gly
    610                 615                 620

Pro Ser Gly Pro Gly Ser Gly Pro Gly Gly Ser Gly Pro Gly Gly Tyr
625                 630                 635                 640

Gly Pro Gly Gly Ser Gly Pro Gly Gly Tyr Gly Pro Gly Gly Ser Gly
                645                 650                 655

Pro Gly Gly Tyr Gly Pro Gly Gly Ser Gly Pro Gly Gly Tyr Gly Pro
                660                 665                 670

Gly Gly Ser Gly Pro Gly Gly Tyr Ala Ala Ala Ala Ala Gly Pro
        675                 680                 685

Ser Gly Pro Gly Ser Gly Pro Gly Gly Ser Gly Pro Gly Gly Tyr Gly
690                 695                 700

Pro Gly Gly Ser Gly Pro Gly Gly Tyr Gly Pro Gly Gly Ser Gly Pro
705                 710                 715                 720

Gly Gly Tyr Gly Pro Gly Gly Ser Gly Pro Gly Gly Tyr Gly Pro Gly
                725                 730                 735

Gly Ser Gly Pro Gly Gly Tyr Ala Ala Ala Ala Ala Gly Pro Ser
            740                 745                 750

Gly Pro Gly Ser Gly Pro Gly Gly Ser Gly Pro Gly Gly Tyr Gly Pro
                755                 760                 765

Gly Gly Ser Gly Pro Gly Gly Tyr Gly Pro Gly Gly Ser Gly Pro Gly
            770                 775                 780

Gly Tyr Gly Pro Gly Gly Ser Gly Pro Gly Gly Tyr Gly Pro Gly Gly
785                 790                 795                 800

Ser Gly Pro Gly Gly Tyr Ala Ala Ala Ala Ala Gly Pro Ser Gly
            805                 810                 815

Pro Gly Ser Gly Pro Gly Gly Ser Gly Pro Gly Gly Tyr Gly Pro Gly
            820                 825                 830

Gly Ser Gly Pro Gly Gly Tyr Gly Pro Gly Gly Ser Gly Pro Gly Gly
            835                 840                 845

Tyr Gly Pro Gly Gly Ser Gly Pro Gly Gly Tyr Gly Pro Gly Gly Ser
850                 855                 860

Gly Pro Gly Gly Tyr Ala Ala Ala Ala Ala Gly Pro Ser Gly Pro
865                 870                 875                 880

Gly Ser Gly Pro Gly Gly Ser Gly Pro Gly Gly Tyr Gly Pro Gly Gly
            885                 890                 895

Ser Gly Pro Gly Gly Tyr Gly Pro Gly Gly Ser Gly Pro Gly Gly Tyr
                900                 905                 910

Gly Pro Gly Gly Ser Gly Pro Gly Gly Tyr Gly Pro Gly Gly Ser Gly
            915                 920                 925

Pro Gly Gly Tyr Ala Ala Ala Ala Ala Gly Pro Ser Gly Pro Gly
            930                 935                 940

Ser Gly Pro Gly Gly Ser Gly Pro Gly Gly Tyr Gly Pro Gly Gly Ser
945                 950                 955                 960
```

-continued

```
Gly Pro Gly Gly Tyr Gly Pro Gly Gly Ser Gly Pro Gly Gly Tyr Gly
            965                 970                 975
Pro Gly Gly Ser Gly Pro Gly Gly Tyr Gly Pro Gly Gly Ser Gly Pro
        980                 985                 990
Gly Gly Tyr Ala Ala Ala Ala Ala Ala Gly Pro Ser Gly Pro Gly Ser
    995                1000                1005
Gly Pro Gly Gly Ser Gly Pro Gly Gly Tyr Gly Pro Gly Gly Ser Gly
   1010                1015                1020
Pro Gly Gly Tyr Gly Pro Gly Gly Ser Gly Pro Gly Gly Tyr Gly Pro
1025                1030                1035                1040
Gly Gly Ser Gly Pro Gly Gly Tyr Gly Pro Gly Gly Ser Gly Pro Gly
           1045                1050                1055
Gly Tyr Ala Ala Ala Ala Ala Gly Pro Ser Gly Pro Gly Ser Gly
       1060                1065                1070
Pro Gly Gly Ser Gly Pro Gly Gly Tyr Gly Pro Gly Gly Ser Gly Pro
        1075                1080                1085
Gly Gly Tyr Gly Pro Gly Gly Ser Gly Pro Gly Gly Tyr Gly Pro Gly
    1090                1095                1100
Gly Ser Gly Pro Gly Gly Tyr Gly Pro Gly Gly Ser Gly Pro Gly Gly
1105                1110                1115                1120
Tyr Ala Ala Ala Ala Ala Ala Gly Pro Ser Gly Pro Gly Ser Gly Pro
        1125                1130                1135
Gly Gly Ser Gly Pro Gly Gly Tyr Gly Pro Gly Gly Ser Gly Pro Gly
           1140                1145                1150
Gly Tyr Gly Pro Gly Gly Ser Gly Pro Gly Gly Tyr Gly Pro Gly Gly
       1155                1160                1165
Ser Gly Pro Gly Gly Tyr Gly Pro Gly Gly Ser Gly Pro Gly Gly Tyr
    1170                1175                1180
Ala Ala Ala Ala Ala Ala Gly Pro Ser Gly Pro Gly Ser Gly Pro Gly
1185                1190                1195                1200
Gly Ser Gly Pro Gly Gly Tyr Gly Pro Gly Gly Ser Gly Pro Gly Gly
        1205                1210                1215
Tyr Gly Pro Gly Gly Ser Gly Pro Gly Gly Tyr Gly Pro Gly Gly Ser
       1220                1225                1230
Gly Pro Gly Gly Tyr Gly Pro Gly Gly Ser Gly Pro Gly Gly Tyr Ala
    1235                1240                1245
Ala Ala Ala Ala Gly Pro Ser Gly Pro Gly Ser Gly Pro Gly Gly
1250                1255                1260
Ser Gly Pro Gly Gly Tyr Gly Pro Gly Gly Ser Gly Pro Gly Gly Tyr
1265                1270                1275                1280
Gly Pro Gly Gly Ser Gly Pro Gly Gly Tyr Gly Pro Gly Gly Ser Gly
           1285                1290                1295
Pro Gly Gly Tyr Gly Pro Gly Gly Ser Gly Pro Gly Gly Tyr Ala Ala
       1300                1305                1310
Ala Ala Ala Gly Pro Ser Gly Pro Gly Ser Gly Pro Gly Gly Ser
    1315                1320                1325
Gly Pro Gly Gly Tyr Gly Pro Gly Gly Ser Gly Pro Gly Gly Tyr Gly
        1330                1335                1340
Pro Gly Gly Ser Gly Pro Gly Gly Tyr Gly Pro Gly Gly Ser Gly Pro
1345                1350                1355                1360
Gly Gly Tyr Gly Pro Gly Gly Ser Gly Pro Gly Gly Tyr Ala Ala Ala
           1365                1370                1375
Ala Ala Ala Gly Pro Ser Gly Pro Gly Ser Gly Pro Gly Gly Ser Gly
```

-continued

```
              1380            1385            1390
Pro Gly Gly Tyr Gly Pro Gly Gly Ser Gly Pro Gly Gly Tyr Gly Pro
        1395            1400            1405
Gly Gly Ser Gly Pro Gly Gly Tyr Gly Pro Gly Gly Ser Gly Pro Gly
        1410            1415            1420
Gly Tyr Gly Pro Gly Gly Ser Gly Pro Gly Gly Tyr Ala Ala Ala Ala
1425            1430            1435            1440
Ala Ala Gly Pro Ser Gly Pro Gly Ser Gly Pro Gly Gly Ser Gly Pro
            1445            1450            1455
Gly Gly Tyr Gly Pro Gly Gly Ser Gly Pro Gly Gly Tyr Gly Pro Gly
        1460            1465            1470
Gly Ser Gly Pro Gly Gly Tyr Gly Pro Gly Gly Ser Gly Pro Gly Gly
        1475            1480            1485
Tyr Gly Pro Gly Gly Ser Gly Pro Gly Gly Tyr Ala Ala Ala Ala Ala
    1490            1495            1500
Ala Gly Pro Ser Gly Pro Gly Ser Gly Pro Gly Gly Ser Gly Pro Gly
1505            1510            1515            1520
Gly Tyr Gly Pro Gly Gly Ser Gly Pro Gly Gly Tyr Gly Pro Gly Gly
        1525            1530            1535
Ser Gly Pro Gly Gly Tyr Gly Pro Gly Gly Ser Gly Pro Gly Gly Tyr
        1540            1545            1550
Gly Pro Gly Gly Ser Gly Pro Gly Gly Tyr Ala Ala Ala Ala Ala Ala
    1555            1560            1565
Gly Pro Ser Gly Pro Gly Ser Gly Pro Gly Gly Ser Gly Pro Gly Gly
        1570            1575            1580
Tyr Gly Pro Gly Gly Ser Gly Pro Gly Gly Tyr Gly Pro Gly Gly Ser
1585            1590            1595            1600
Gly Pro Gly Gly Tyr Gly Pro Gly Gly Ser Gly Pro Gly Gly Tyr Gly
        1605            1610            1615
Pro Gly Gly Ser Gly Pro Gly Gly Tyr Ala Ala Ala Ala Ala Gly
        1620            1625            1630
Pro Ser Gly Pro Gly Ser Gly Pro Gly Gly Ser Gly Pro Gly Gly Tyr
        1635            1640            1645
Gly Pro Gly Gly Ser Gly Pro Gly Gly Tyr Gly Pro Gly Gly Ser Gly
    1650            1655            1660
Pro Gly Gly Tyr Gly Pro Gly Gly Ser Gly Pro Gly Gly Tyr Gly Pro
1665            1670            1675            1680
Gly Gly Ser Gly Pro Gly Gly Tyr Ala Ala Ala Ala Ala Gly Pro
            1685            1690            1695
Ser Gly Pro Gly Ser Gly Pro Gly Gly Ser Gly Pro Gly Gly Tyr Gly
        1700            1705            1710
Pro Gly Gly Ser Gly Pro Gly Gly Tyr Gly Pro Gly Gly Ser Gly Pro
        1715            1720            1725
Gly Gly Tyr Gly Pro Gly Gly Ser Gly Pro Gly Gly Tyr Gly Pro Gly
        1730            1735            1740
Gly Ser Gly Pro Gly Gly Tyr Ala Ala Ala Ala Ala Gly Pro Ser
1745            1750            1755            1760
Gly Pro Gly Ser Gly Pro Gly Gly Ser Gly Pro Gly Gly Tyr Gly Pro
            1765            1770            1775
Gly Gly Ser Gly Pro Gly Gly Tyr Gly Pro Gly Gly Ser Gly Pro Gly
        1780            1785            1790
Gly Tyr Gly Pro Gly Gly Ser Gly Pro Gly Gly Tyr Gly Pro Gly Gly
        1795            1800            1805
```

Ser Gly Pro Gly Gly Tyr Ala Ala Ala Ala Ala Gly Pro Ser Gly
    1810                1815                1820

Pro Gly Ser Gly Pro Gly Gly Ser Gly Pro Gly Gly Tyr Gly Pro Gly
1825                1830                1835                1840

Gly Ser Gly Pro Gly Gly Tyr Gly Pro Gly Gly Ser Gly Pro Gly Gly
            1845                1850                1855

Tyr Gly Pro Gly Gly Ser Gly Pro Gly Gly Tyr Gly Pro Gly Gly Ser
            1860                1865                1870

Gly Pro Gly Gly Tyr Ala Ala Ala Ala Ala Gly Pro Ser Gly Pro
        1875                1880                1885

Gly Ser Gly Pro Gly Gly Ser Gly Pro Gly Gly Tyr Gly Pro Gly Gly
        1890                1895                1900

Ser Gly Pro Gly Gly Tyr Gly Pro Gly Gly Ser Gly Pro Gly Gly Tyr
1905                1910                1915                1920

Gly Pro Gly Gly Ser Gly Pro Gly Gly Tyr Gly Pro Gly Gly Ser Gly
            1925                1930                1935

Pro Gly Gly Tyr Ala Ala Ala Ala Ala Gly Pro Ser Gly Pro Gly
        1940                1945                1950

Ser Gly Pro Gly Gly Ser Gly Pro Gly Gly Tyr Gly Pro Gly Gly Ser
1955                1960                1965

Gly Pro Gly Gly Tyr Gly Pro Gly Gly Ser Gly Pro Gly Gly Tyr Gly
        1970                1975                1980

Pro Gly Gly Ser Gly Pro Gly Gly Tyr Gly Pro Gly Gly Ser Gly Pro
1985                1990                1995                2000

Gly Gly Tyr Ala Ala Ala Ala Ala Gly Pro Ser Gly Pro Gly Ser
            2005                2010                2015

<210> SEQ ID NO 53
<211> LENGTH: 2304
<212> TYPE: PRT
<213> ORGANISM: Artificial Sequence
<220> FEATURE:
<223> OTHER INFORMATION: synthetic spider silk protein

<400> SEQUENCE: 53

Gly Gly Tyr Gly Gly Leu Gly Gly Gln Gly Gly Tyr Gly Gly Leu Gly
1               5                   10                  15

Gly Gln Gly Ala Gly Ala Gly Ala Gly Ala Gly Ala Gly Ala Gly Ala
            20                  25                  30

Gly Ala Gly Ala Gly Gly Tyr Gly Gly Leu Gly Gly Gln Gly Gly Tyr
        35                  40                  45

Gly Gly Leu Gly Gly Gln Gly Ala Gly Ala Gly Ala Gly Ala Gly Ala
    50                  55                  60

Gly Ala Gly Ala Gly Ala Gly Ala Gly Tyr Gly Gly Leu Gly Gly
65                  70                  75                  80

Gln Gly Gly Tyr Gly Gly Leu Gly Gly Gln Gly Ala Gly Ala Gly Ala
                85                  90                  95

Gly Ala Gly Ala Gly Ala Gly Ala Gly Ala Gly Ala Gly Gly Tyr Gly
            100                 105                 110

Gly Leu Gly Gly Gln Gly Gly Tyr Gly Gly Leu Gly Gly Gln Gly Ala
        115                 120                 125

Gly Ala Gly Ala Gly Ala Gly Ala Gly Ala Gly Ala Gly Ala Gly Ala
    130                 135                 140

Gly Gly Tyr Gly Gly Leu Gly Gly Gln Gly Gly Tyr Gly Gly Leu Gly
145                 150                 155                 160

-continued

```
Gly Gln Gly Ala Gly Ala Gly Ala Gly Ala Gly Ala Gly Ala
            165                 170                 175
Gly Ala Gly Ala Gly Gly Tyr Gly Gly Leu Gly Gly Gln Gly Gly Tyr
        180                 185                 190
Gly Gly Leu Gly Gly Gln Gly Ala Gly Ala Gly Ala Gly Ala Gly Ala
            195                 200                 205
Gly Ala Gly Ala Gly Ala Gly Ala Gly Gly Tyr Gly Gly Leu Gly Gly
            210                 215                 220
Gln Gly Gly Tyr Gly Gly Leu Gly Gly Gln Gly Ala Gly Ala Gly Ala
225                 230                 235                 240
Gly Ala Gly Ala Gly Ala Gly Ala Gly Ala Gly Ala Gly Gly Tyr Gly
            245                 250                 255
Gly Leu Gly Gly Gln Gly Gly Tyr Gly Gly Leu Gly Gly Gln Gly Ala
            260                 265                 270
Gly Ala Gly Ala Gly Ala Gly Ala Gly Ala Gly Ala Gly Ala Gly Ala
            275                 280                 285
Gly Gly Tyr Gly Gly Leu Gly Gly Gln Gly Gly Tyr Gly Gly Leu Gly
            290                 295                 300
Gly Gln Gly Ala Gly Ala Gly Ala Gly Ala Gly Ala Gly Ala Gly Ala
305                 310                 315                 320
Gly Ala Gly Ala Gly Gly Tyr Gly Gly Leu Gly Gly Gln Gly Gly Tyr
            325                 330                 335
Gly Gly Leu Gly Gly Gln Gly Ala Gly Ala Gly Ala Gly Ala Gly Ala
            340                 345                 350
Gly Ala Gly Ala Gly Ala Gly Ala Gly Gly Tyr Gly Gly Leu Gly Gly
            355                 360                 365
Gln Gly Gly Tyr Gly Gly Leu Gly Gly Gln Gly Ala Gly Ala Gly Ala
            370                 375                 380
Gly Ala Gly Ala Gly Ala Gly Ala Gly Ala Gly Ala Gly Gly Tyr Gly
385                 390                 395                 400
Gly Leu Gly Gly Gln Gly Gly Tyr Gly Gly Leu Gly Gly Gln Gly Ala
            405                 410                 415
Gly Ala Gly Ala Gly Ala Gly Ala Gly Ala Gly Ala Gly Ala Gly Ala
            420                 425                 430
Gly Gly Tyr Gly Gly Leu Gly Gly Gln Gly Gly Tyr Gly Gly Leu Gly
            435                 440                 445
Gly Gln Gly Ala Gly Ala Gly Ala Gly Ala Gly Ala Gly Ala Gly Ala
450                 455                 460
Gly Ala Gly Ala Gly Gly Tyr Gly Gly Leu Gly Gly Gln Gly Gly Tyr
465                 470                 475                 480
Gly Gly Leu Gly Gly Gln Gly Ala Gly Ala Gly Ala Gly Ala Gly Ala
            485                 490                 495
Gly Ala Gly Ala Gly Ala Gly Gly Tyr Gly Gly Leu Gly Gly
            500                 505                 510
Gln Gly Gly Tyr Gly Gly Leu Gly Gly Gln Gly Ala Gly Ala Gly Ala
            515                 520                 525
Gly Ala Gly Ala Gly Ala Gly Ala Gly Ala Gly Ala Gly Gly Tyr Gly
            530                 535                 540
Gly Leu Gly Gly Gln Gly Gly Tyr Gly Gly Leu Gly Gly Gln Gly Ala
545                 550                 555                 560
Gly Ala Gly Ala Gly Ala Gly Ala Gly Ala Gly Ala Gly Ala Gly Ala
            565                 570                 575
```

-continued

Gly Gly Tyr Gly Gly Leu Gly Gly Gln Gly Gly Tyr Gly Gly Leu Gly
                580                 585                 590
Gly Gln Gly Ala Gly Ala Gly Ala Gly Ala Gly Ala Gly Ala Gly Ala
            595                 600                 605
Gly Ala Gly Ala Gly Gly Tyr Gly Gly Leu Gly Gly Gln Gly Gly Tyr
        610                 615                 620
Gly Gly Leu Gly Gly Gln Gly Ala Gly Ala Gly Ala Gly Ala Gly Ala
625                 630                 635                 640
Gly Ala Gly Ala Gly Ala Gly Ala Gly Gly Tyr Gly Gly Leu Gly Gly
            645                 650                 655
Gln Gly Gly Tyr Gly Gly Leu Gly Gly Gln Gly Ala Gly Ala Gly Ala
        660                 665                 670
Gly Ala Gly Ala Gly Ala Gly Ala Gly Ala Gly Gly Tyr Gly
        675                 680                 685
Gly Leu Gly Gly Gln Gly Gly Tyr Gly Gly Leu Gly Gly Gln Gly Ala
        690                 695                 700
Gly Ala Gly Ala Gly Ala Gly Ala Gly Ala Gly Ala Gly Ala Gly Ala
705                 710                 715                 720
Gly Gly Tyr Gly Gly Leu Gly Gly Gln Gly Gly Tyr Gly Gly Leu Gly
            725                 730                 735
Gly Gln Gly Ala Gly Ala Gly Ala Gly Ala Gly Ala Gly Ala Gly Ala
            740                 745                 750
Gly Ala Gly Ala Gly Gly Tyr Gly Gly Leu Gly Gly Gln Gly Gly Tyr
        755                 760                 765
Gly Gly Leu Gly Gly Gln Gly Ala Gly Ala Gly Ala Gly Ala Gly Ala
        770                 775                 780
Gly Ala Gly Ala Gly Ala Gly Ala Gly Gly Tyr Gly Gly Leu Gly Gly
785                 790                 795                 800
Gln Gly Gly Tyr Gly Gly Leu Gly Gly Gln Gly Ala Gly Ala Gly Ala
            805                 810                 815
Gly Ala Gly Ala Gly Ala Gly Ala Gly Ala Gly Gly Tyr Gly
            820                 825                 830
Gly Leu Gly Gly Gln Gly Gly Tyr Gly Gly Leu Gly Gly Gln Gly Ala
        835                 840                 845
Gly Ala Gly Ala Gly Ala Gly Ala Gly Ala Gly Ala Gly Ala Gly Ala
        850                 855                 860
Gly Gly Tyr Gly Gly Leu Gly Gly Gln Gly Gly Tyr Gly Gly Leu Gly
865                 870                 875                 880
Gly Gln Gly Ala Gly Ala Gly Ala Gly Ala Gly Ala Gly Ala Gly Ala
            885                 890                 895
Gly Ala Gly Ala Gly Gly Tyr Gly Gly Leu Gly Gly Gln Gly Gly Tyr
        900                 905                 910
Gly Gly Leu Gly Gly Gln Gly Ala Gly Ala Gly Ala Gly Ala Gly Ala
        915                 920                 925
Gly Ala Gly Ala Gly Ala Gly Ala Gly Gly Tyr Gly Gly Leu Gly Gly
        930                 935                 940
Gln Gly Gly Tyr Gly Gly Leu Gly Gly Gln Gly Ala Gly Ala Gly Ala
945                 950                 955                 960
Gly Ala Gly Ala Gly Ala Gly Ala Gly Ala Gly Gly Tyr Gly
            965                 970                 975
Gly Leu Gly Gly Gln Gly Gly Tyr Gly Gly Leu Gly Gly Gln Gly Ala
        980                 985                 990
Gly Ala Gly Ala Gly Ala Gly Ala Gly Ala Gly Ala Gly Ala Gly Ala

```
                995                1000               1005
Gly Gly Tyr Gly Gly Leu Gly Gly Gln Gly Gly Tyr Gly Gly Leu Gly
           1010                1015               1020
Gly Gln Gly Ala Gly Ala Gly Ala Gly Ala Gly Ala Gly Ala Gly Ala
1025                1030               1035               1040
Gly Ala Gly Ala Gly Gly Tyr Gly Gly Leu Gly Gly Gln Gly Gly Tyr
           1045                1050               1055
Gly Gly Leu Gly Gly Gln Gly Ala Gly Ala Gly Ala Gly Ala Gly Ala
           1060                1065               1070
Gly Ala Gly Ala Gly Ala Gly Ala Gly Gly Tyr Gly Gly Leu Gly Gly
           1075                1080               1085
Gln Gly Gly Tyr Gly Gly Leu Gly Gly Gln Gly Ala Gly Ala Gly Ala
           1090                1095               1100
Gly Ala Gly Ala Gly Ala Gly Ala Gly Ala Gly Ala Gly Gly Tyr Gly
1105                1110               1115               1120
Gly Leu Gly Gly Gln Gly Gly Tyr Gly Gly Leu Gly Gly Gln Gly Ala
           1125                1130               1135
Gly Ala Gly Ala Gly Ala Gly Ala Gly Ala Gly Ala Gly Ala Gly Ala
           1140                1145               1150
Gly Gly Tyr Gly Gly Leu Gly Gly Gln Gly Gly Tyr Gly Gly Leu Gly
           1155                1160               1165
Gly Gln Gly Ala Gly Ala Gly Ala Gly Ala Gly Ala Gly Ala Gly Ala
           1170                1175               1180
Gly Ala Gly Ala Gly Gly Tyr Gly Gly Leu Gly Gly Gln Gly Gly Tyr
1185                1190               1195               1200
Gly Gly Leu Gly Gly Gln Gly Ala Gly Ala Gly Ala Gly Ala Gly Ala
           1205                1210               1215
Gly Ala Gly Ala Gly Ala Gly Ala Gly Gly Tyr Gly Gly Leu Gly Gly
           1220                1225               1230
Gln Gly Gly Tyr Gly Gly Leu Gly Gly Gln Gly Ala Gly Ala Gly Ala
           1235                1240               1245
Gly Ala Gly Ala Gly Ala Gly Ala Gly Ala Gly Ala Gly Gly Tyr Gly
           1250                1255               1260
Gly Leu Gly Gly Gln Gly Gly Tyr Gly Gly Leu Gly Gly Gln Gly Ala
1265                1270               1275               1280
Gly Ala Gly Ala Gly Ala Gly Ala Gly Ala Gly Ala Gly Ala Gly Ala
           1285                1290               1295
Gly Gly Tyr Gly Gly Leu Gly Gly Gln Gly Gly Tyr Gly Gly Leu Gly
           1300                1305               1310
Gly Gln Gly Ala Gly Ala Gly Ala Gly Ala Gly Ala Gly Ala Gly Ala
           1315                1320               1325
Gly Ala Gly Ala Gly Gly Tyr Gly Gly Leu Gly Gly Gln Gly Gly Tyr
           1330                1335               1340
Gly Gly Leu Gly Gly Gln Gly Ala Gly Ala Gly Ala Gly Ala Gly Ala
1345                1350               1355               1360
Gly Ala Gly Ala Gly Ala Gly Ala Gly Gly Tyr Gly Gly Leu Gly Gly
           1365                1370               1375
Gln Gly Gly Tyr Gly Gly Leu Gly Gly Gln Gly Ala Gly Ala Gly Ala
           1380                1385               1390
Gly Ala Gly Ala Gly Ala Gly Ala Gly Ala Gly Ala Gly Gly Tyr Gly
           1395                1400               1405
Gly Leu Gly Gly Gln Gly Gly Tyr Gly Gly Leu Gly Gly Gln Gly Ala
           1410                1415               1420
```

```
Gly Ala Gly Ala Gly Ala Gly Ala Gly Ala Gly Ala Gly Ala Gly Ala
1425                1430                1435                1440

Gly Gly Tyr Gly Gly Leu Gly Gly Gln Gly Gly Tyr Gly Gly Leu Gly
            1445                1450                1455

Gly Gln Gly Ala Gly Ala Gly Ala Gly Ala Gly Ala Gly Ala Gly Ala
        1460                1465                1470

Gly Ala Gly Ala Gly Gly Tyr Gly Gly Leu Gly Gly Gln Gly Gly Tyr
            1475                1480                1485

Gly Gly Leu Gly Gly Gln Gly Ala Gly Ala Gly Ala Gly Ala Gly Ala
        1490                1495                1500

Gly Ala Gly Ala Gly Ala Gly Ala Gly Gly Tyr Gly Gly Leu Gly Gly
1505                1510                1515                1520

Gln Gly Gly Tyr Gly Gly Leu Gly Gly Gln Gly Ala Gly Ala Gly Ala
            1525                1530                1535

Gly Ala Gly Ala Gly Ala Gly Ala Gly Ala Gly Ala Gly Gly Tyr Gly
            1540                1545                1550

Gly Leu Gly Gly Gln Gly Gly Tyr Gly Gly Leu Gly Gly Gln Gly Ala
        1555                1560                1565

Gly Ala Gly Ala Gly Ala Gly Ala Gly Ala Gly Ala Gly Ala Gly Ala
        1570                1575                1580

Gly Gly Tyr Gly Gly Leu Gly Gly Gln Gly Gly Tyr Gly Gly Leu Gly
1585                1590                1595                1600

Gly Gln Gly Ala Gly Ala Gly Ala Gly Ala Gly Ala Gly Ala Gly Ala
        1605                1610                1615

Gly Ala Gly Ala Gly Gly Tyr Gly Gly Leu Gly Gly Gln Gly Gly Tyr
            1620                1625                1630

Gly Gly Leu Gly Gly Gln Gly Ala Gly Ala Gly Ala Gly Ala Gly Ala
        1635                1640                1645

Gly Ala Gly Ala Gly Ala Gly Ala Gly Gly Tyr Gly Gly Leu Gly Gly
        1650                1655                1660

Gln Gly Gly Tyr Gly Gly Leu Gly Gly Gln Gly Ala Gly Ala Gly Ala
1665                1670                1675                1680

Gly Ala Gly Ala Gly Ala Gly Ala Gly Ala Gly Ala Gly Gly Tyr Gly
            1685                1690                1695

Gly Leu Gly Gly Gln Gly Gly Tyr Gly Gly Leu Gly Gly Gln Gly Ala
        1700                1705                1710

Gly Ala Gly Ala Gly Ala Gly Ala Gly Ala Gly Ala Gly Ala Gly Ala
        1715                1720                1725

Gly Gly Tyr Gly Gly Leu Gly Gly Gln Gly Gly Tyr Gly Gly Leu Gly
        1730                1735                1740

Gly Gln Gly Ala Gly Ala Gly Ala Gly Ala Gly Ala Gly Ala Gly Ala
1745                1750                1755                1760

Gly Ala Gly Ala Gly Gly Tyr Gly Gly Leu Gly Gly Gln Gly Gly Tyr
            1765                1770                1775

Gly Gly Leu Gly Gly Gln Gly Ala Gly Ala Gly Ala Gly Ala Gly Ala
        1780                1785                1790

Gly Ala Gly Ala Gly Ala Gly Ala Gly Gly Tyr Gly Gly Leu Gly Gly
        1795                1800                1805

Gln Gly Gly Tyr Gly Gly Leu Gly Gly Gln Gly Ala Gly Ala Gly Ala
        1810                1815                1820

Gly Ala Gly Ala Gly Ala Gly Ala Gly Ala Gly Ala Gly Gly Tyr Gly
1825                1830                1835                1840
```

-continued

Gly Leu Gly Gly Gln Gly Gly Tyr Gly Gly Leu Gly Gly Gln Gly Ala
            1845                1850                1855

Gly Ala Gly Ala Gly Ala Gly Ala Gly Ala Gly Ala Gly Ala Gly Ala
        1860                1865                1870

Gly Gly Tyr Gly Gly Leu Gly Gly Gln Gly Gly Tyr Gly Gly Leu Gly
        1875                1880                1885

Gly Gln Gly Ala Gly Ala Gly Ala Gly Ala Gly Ala Gly Ala Gly Ala
        1890                1895                1900

Gly Ala Gly Ala Gly Gly Tyr Gly Gly Leu Gly Gly Gln Gly Gly Tyr
1905                1910                1915                1920

Gly Gly Leu Gly Gly Gln Gly Ala Gly Ala Gly Ala Gly Ala Gly Ala
            1925                1930                1935

Gly Ala Gly Ala Gly Ala Gly Ala Gly Gly Tyr Gly Gly Leu Gly Gly
            1940                1945                1950

Gln Gly Gly Tyr Gly Gly Leu Gly Gly Gln Gly Ala Gly Ala Gly Ala
        1955                1960                1965

Gly Ala Gly Ala Gly Ala Gly Ala Gly Ala Gly Ala Gly Gly Tyr Gly
        1970                1975                1980

Gly Leu Gly Gly Gln Gly Gly Tyr Gly Gly Leu Gly Gly Gln Gly Ala
1985                1990                1995                2000

Gly Ala Gly Ala Gly Ala Gly Ala Gly Ala Gly Ala Gly Ala Gly Ala
            2005                2010                2015

Gly Gly Tyr Gly Gly Leu Gly Gly Gln Gly Gly Tyr Gly Gly Leu Gly
            2020                2025                2030

Gly Gln Gly Ala Gly Ala Gly Ala Gly Ala Gly Ala Gly Ala Gly Ala
            2035                2040                2045

Gly Ala Gly Ala Gly Gly Tyr Gly Gly Leu Gly Gly Gln Gly Gly Tyr
        2050                2055                2060

Gly Gly Leu Gly Gly Gln Gly Ala Gly Ala Gly Ala Gly Ala Gly Ala
2065                2070                2075                2080

Gly Ala Gly Ala Gly Ala Gly Ala Gly Gly Tyr Gly Gly Leu Gly Gly
            2085                2090                2095

Gln Gly Gly Tyr Gly Gly Leu Gly Gly Gln Gly Ala Gly Ala Gly Ala
        2100                2105                2110

Gly Ala Gly Ala Gly Ala Gly Ala Gly Ala Gly Ala Gly Gly Tyr Gly
        2115                2120                2125

Gly Leu Gly Gly Gln Gly Gly Tyr Gly Gly Leu Gly Gly Gln Gly Ala
        2130                2135                2140

Gly Ala Gly Ala Gly Ala Gly Ala Gly Ala Gly Ala Gly Ala Gly Ala
2145                2150                2155                2160

Gly Gly Tyr Gly Gly Leu Gly Gly Gln Gly Gly Tyr Gly Gly Leu Gly
            2165                2170                2175

Gly Gln Gly Ala Gly Ala Gly Ala Gly Ala Gly Ala Gly Ala Gly Ala
            2180                2185                2190

Gly Ala Gly Ala Gly Gly Tyr Gly Gly Leu Gly Gly Gln Gly Gly Tyr
        2195                2200                2205

Gly Gly Leu Gly Gly Gln Gly Ala Gly Ala Gly Ala Gly Ala Gly Ala
        2210                2215                2220

Gly Ala Gly Ala Gly Ala Gly Ala Gly Gly Tyr Gly Gly Leu Gly Gly
2225                2230                2235                2240

Gln Gly Gly Tyr Gly Gly Leu Gly Gly Gln Gly Ala Gly Ala Gly Ala
            2245                2250                2255

Gly Ala Gly Ala Gly Ala Gly Ala Gly Ala Gly Ala Gly Gly Tyr Gly

-continued

```
                    2260               2265               2270
    Gly Leu Gly Gly Gln Gly Gly Tyr Gly Gly Leu Gly Gly Gln Gly Ala
            2275               2280               2285
    Gly Ala Gly Ala Gly Ala Gly Ala Gly Ala Gly Ala Gly Ala Gly Ala
            2290               2295               2300

<210> SEQ ID NO 54
<211> LENGTH: 1536
<212> TYPE: PRT
<213> ORGANISM: Artificial Sequence
<220> FEATURE:
<223> OTHER INFORMATION: synthetic spider silk protein

<400> SEQUENCE: 54

Gly Gly Val Gly Gly Ala Gly Gly Val Gly Gly Ala Gly Gly Val Gly
 1               5                  10                  15

Gly Ala Gly Val Gly Val Gly Val Gly Val Gly Val Gly Val Gly Val
            20                  25                  30

Gly Gly Val Gly Gly Ala Gly Gly Val Gly Gly Ala Gly Gly Val Gly
            35                  40                  45

Gly Ala Gly Val Gly Val Gly Val Gly Val Gly Val Gly Val Gly Val
        50                  55                  60

Gly Gly Val Gly Gly Ala Gly Gly Val Gly Gly Ala Gly Gly Val Gly
65                  70                  75                  80

Gly Ala Gly Val Gly Val Gly Val Gly Val Gly Val Gly Val Gly Val
                85                  90                  95

Gly Gly Val Gly Gly Ala Gly Gly Val Gly Gly Ala Gly Gly Val Gly
                100                 105                 110

Gly Ala Gly Val Gly Val Gly Val Gly Val Gly Val Gly Val Gly Val
            115                 120                 125

Gly Gly Val Gly Gly Ala Gly Gly Val Gly Gly Ala Gly Gly Val Gly
        130                 135                 140

Gly Ala Gly Val Gly Val Gly Val Gly Val Gly Val Gly Val Gly Val
145                 150                 155                 160

Gly Gly Val Gly Gly Ala Gly Gly Val Gly Gly Ala Gly Gly Val Gly
                165                 170                 175

Gly Ala Gly Val Gly Val Gly Val Gly Val Gly Val Gly Val Gly Val
                180                 185                 190

Gly Gly Val Gly Gly Ala Gly Gly Val Gly Gly Ala Gly Gly Val Gly
            195                 200                 205

Gly Ala Gly Val Gly Val Gly Val Gly Val Gly Val Gly Val Gly Val
        210                 215                 220

Gly Gly Val Gly Gly Ala Gly Gly Val Gly Gly Ala Gly Gly Val Gly
225                 230                 235                 240

Gly Ala Gly Val Gly Val Gly Val Gly Val Gly Val Gly Val Gly Val
                245                 250                 255

Gly Gly Val Gly Gly Ala Gly Gly Val Gly Gly Ala Gly Gly Val Gly
                260                 265                 270

Gly Ala Gly Val Gly Val Gly Val Gly Val Gly Val Gly Val Gly Val
            275                 280                 285

Gly Gly Val Gly Gly Ala Gly Gly Val Gly Gly Ala Gly Gly Val Gly
        290                 295                 300

Gly Ala Gly Val Gly Val Gly Val Gly Val Gly Val Gly Val Gly Val
305                 310                 315                 320

Gly Gly Val Gly Gly Ala Gly Gly Val Gly Gly Ala Gly Gly Val Gly
```

-continued

```
                325                 330                 335
Gly Ala Gly Val Gly Val Gly Val Gly Val Gly Val Gly Val
            340                 345                 350
Gly Gly Val Gly Gly Ala Gly Gly Val Gly Gly Ala Gly Gly Val Gly
            355                 360                 365
Gly Ala Gly Val Gly Val Gly Val Gly Val Gly Val Gly Val
            370                 375                 380
Gly Gly Val Gly Gly Ala Gly Gly Val Gly Gly Ala Gly Gly Val Gly
385                 390                 395                 400
Gly Ala Gly Val Gly Val Gly Val Gly Val Gly Val Gly Val
            405                 410                 415
Gly Gly Val Gly Gly Ala Gly Gly Val Gly Gly Ala Gly Gly Val Gly
            420                 425                 430
Gly Ala Gly Val Gly Val Gly Val Gly Val Gly Val Gly Val
            435                 440                 445
Gly Gly Val Gly Gly Ala Gly Gly Val Gly Gly Ala Gly Gly Val Gly
            450                 455                 460
Gly Ala Gly Val Gly Val Gly Val Gly Val Gly Val Gly Val
465                 470                 475                 480
Gly Gly Val Gly Gly Ala Gly Gly Val Gly Gly Ala Gly Gly Val Gly
            485                 490                 495
Gly Ala Gly Val Gly Val Gly Val Gly Val Gly Val Gly Val
            500                 505                 510
Gly Gly Val Gly Gly Ala Gly Gly Val Gly Gly Ala Gly Gly Val Gly
            515                 520                 525
Gly Ala Gly Val Gly Val Gly Val Gly Val Gly Val Gly Val
            530                 535                 540
Gly Gly Val Gly Gly Ala Gly Gly Val Gly Gly Ala Gly Gly Val Gly
545                 550                 555                 560
Gly Ala Gly Val Gly Val Gly Val Gly Val Gly Val Gly Val
            565                 570                 575
Gly Gly Val Gly Gly Ala Gly Gly Val Gly Gly Ala Gly Gly Val Gly
            580                 585                 590
Gly Ala Gly Val Gly Val Gly Val Gly Val Gly Val Gly Val
            595                 600                 605
Gly Gly Val Gly Gly Ala Gly Gly Val Gly Gly Ala Gly Gly Val Gly
            610                 615                 620
Gly Ala Gly Val Gly Val Gly Val Gly Val Gly Val Gly Val
625                 630                 635                 640
Gly Gly Val Gly Gly Ala Gly Gly Val Gly Gly Ala Gly Gly Val Gly
            645                 650                 655
Gly Ala Gly Val Gly Val Gly Val Gly Val Gly Val Gly Val
            660                 665                 670
Gly Gly Val Gly Gly Ala Gly Gly Val Gly Gly Ala Gly Gly Val Gly
            675                 680                 685
Gly Ala Gly Val Gly Val Gly Val Gly Val Gly Val Gly Val
            690                 695                 700
Gly Gly Val Gly Gly Ala Gly Gly Val Gly Gly Ala Gly Gly Val Gly
705                 710                 715                 720
Gly Ala Gly Val Gly Val Gly Val Gly Val Gly Val Gly Val
            725                 730                 735
```

-continued

```
Gly Gly Val Gly Gly Ala Gly Gly Val Gly Gly Ala Gly Gly Val Gly
                740                 745                 750
Gly Ala Gly Val Gly Val Gly Val Gly Val Gly Val Gly Val Gly Val
            755                 760                 765
Gly Gly Val Gly Gly Ala Gly Gly Val Gly Gly Ala Gly Gly Val Gly
            770                 775                 780
Gly Ala Gly Val Gly Val Gly Val Gly Val Gly Val Gly Val Gly Val
785                 790                 795                 800
Gly Gly Val Gly Gly Ala Gly Gly Val Gly Gly Ala Gly Gly Val Gly
                805                 810                 815
Gly Ala Gly Val Gly Val Gly Val Gly Val Gly Val Gly Val Gly Val
            820                 825                 830
Gly Gly Val Gly Gly Ala Gly Gly Val Gly Gly Ala Gly Gly Val Gly
            835                 840                 845
Gly Ala Gly Val Gly Val Gly Val Gly Val Gly Val Gly Val Gly Val
            850                 855                 860
Gly Gly Val Gly Gly Ala Gly Gly Val Gly Gly Ala Gly Gly Val Gly
865                 870                 875                 880
Gly Ala Gly Val Gly Val Gly Val Gly Val Gly Val Gly Val Gly Val
                885                 890                 895
Gly Gly Val Gly Gly Ala Gly Gly Val Gly Gly Ala Gly Gly Val Gly
                900                 905                 910
Gly Ala Gly Val Gly Val Gly Val Gly Val Gly Val Gly Val Gly Val
            915                 920                 925
Gly Gly Val Gly Gly Ala Gly Gly Val Gly Gly Ala Gly Gly Val Gly
            930                 935                 940
Gly Ala Gly Val Gly Val Gly Val Gly Val Gly Val Gly Val Gly Val
945                 950                 955                 960
Gly Gly Val Gly Gly Ala Gly Gly Val Gly Gly Ala Gly Gly Val Gly
                965                 970                 975
Gly Ala Gly Val Gly Val Gly Val Gly Val Gly Val Gly Val Gly Val
            980                 985                 990
Gly Gly Val Gly Gly Ala Gly Gly Val Gly Gly Ala Gly Gly Val Gly
            995                 1000                1005
Gly Ala Gly Val Gly Val Gly Val Gly Val Gly Val Gly Val Gly Val
            1010                1015                1020
Gly Gly Val Gly Gly Ala Gly Gly Val Gly Gly Ala Gly Gly Val Gly
1025                1030                1035                1040
Gly Ala Gly Val Gly Val Gly Val Gly Val Gly Val Gly Val Gly Val
                1045                1050                1055
Gly Gly Val Gly Gly Ala Gly Gly Val Gly Gly Ala Gly Gly Val Gly
                1060                1065                1070
Gly Ala Gly Val Gly Val Gly Val Gly Val Gly Val Gly Val Gly Val
            1075                1080                1085
Gly Gly Val Gly Gly Ala Gly Gly Val Gly Gly Ala Gly Gly Val Gly
            1090                1095                1100
Gly Ala Gly Val Gly Val Gly Val Gly Val Gly Val Gly Val Gly Val
1105                1110                1115                1120
Gly Gly Val Gly Gly Ala Gly Gly Val Gly Gly Ala Gly Gly Val Gly
                1125                1130                1135
```

-continued

```
Gly Ala Gly Val Gly Val Gly Val Gly Val Gly Val Gly Val
            1140            1145            1150
Gly Gly Val Gly Gly Ala Gly Gly Val Gly Gly Ala Gly Gly Val Gly
        1155            1160            1165
Gly Ala Gly Val Gly Val Gly Val Gly Val Gly Val Gly Val
            1170            1175            1180
Gly Gly Val Gly Gly Ala Gly Gly Val Gly Gly Ala Gly Gly Val Gly
1185            1190            1195            1200
Gly Ala Gly Val Gly Val Gly Val Gly Val Gly Val Gly Val
            1205            1210            1215
Gly Gly Val Gly Gly Ala Gly Gly Val Gly Gly Ala Gly Gly Val Gly
        1220            1225            1230
Gly Ala Gly Val Gly Val Gly Val Gly Val Gly Val Gly Val
            1235            1240            1245
Gly Gly Val Gly Gly Ala Gly Gly Val Gly Gly Ala Gly Gly Val Gly
        1250            1255            1260
Gly Ala Gly Val Gly Val Gly Val Gly Val Gly Val Gly Val
1265            1270            1275            1280
Gly Gly Val Gly Gly Ala Gly Gly Val Gly Gly Ala Gly Gly Val Gly
        1285            1290            1295
Gly Ala Gly Val Gly Val Gly Val Gly Val Gly Val Gly Val
            1300            1305            1310
Gly Gly Val Gly Gly Ala Gly Gly Val Gly Gly Ala Gly Gly Val Gly
        1315            1320            1325
Gly Ala Gly Val Gly Val Gly Val Gly Val Gly Val Gly Val
            1330            1335            1340
Gly Gly Val Gly Gly Ala Gly Gly Val Gly Gly Ala Gly Gly Val Gly
1345            1350            1355            1360
Gly Ala Gly Val Gly Val Gly Val Gly Val Gly Val Gly Val
            1365            1370            1375
Gly Gly Val Gly Gly Ala Gly Gly Val Gly Gly Ala Gly Gly Val Gly
        1380            1385            1390
Gly Ala Gly Val Gly Val Gly Val Gly Val Gly Val Gly Val
            1395            1400            1405
Gly Gly Val Gly Gly Ala Gly Gly Val Gly Gly Ala Gly Gly Val Gly
        1410            1415            1420
Gly Ala Gly Val Gly Val Gly Val Gly Val Gly Val Gly Val
1425            1430            1435            1440
Gly Gly Val Gly Gly Ala Gly Gly Val Gly Gly Ala Gly Gly Val Gly
        1445            1450            1455
Gly Ala Gly Val Gly Val Gly Val Gly Val Gly Val Gly Val
            1460            1465            1470
Gly Gly Val Gly Gly Ala Gly Gly Val Gly Gly Ala Gly Gly Val Gly
        1475            1480            1485
Gly Ala Gly Val Gly Val Gly Val Gly Val Gly Val Gly Val
            1490            1495            1500
Gly Gly Val Gly Gly Ala Gly Gly Val Gly Gly Ala Gly Gly Val Gly
1505            1510            1515            1520
Gly Ala Gly Val Gly Val Gly Val Gly Val Gly Val Gly Val
            1525            1530            1535
```